(12) United States Patent
Kinoyama et al.

(10) Patent No.: US 8,853,242 B2
(45) Date of Patent: Oct. 7, 2014

(54) NITROGENOUS-RING ACYLGUANIDINE DERIVATIVE

(75) Inventors: Isao Kinoyama, Tokyo (JP); Takehiro Miyazaki, Tokyo (JP); Yohei Koganemaru, Tokyo (JP); Takuya Washio, Tokyo (JP); Wataru Hamaguchi, Tokyo (JP)

(73) Assignee: Astellas Pharma Inc., Chuo-Ku, Tokyo (JP)

(*) Notice: Subject to any disclaimer, the term of this patent is extended or adjusted under 35 U.S.C. 154(b) by 374 days.

(21) Appl. No.: 13/388,872

(22) PCT Filed: Aug. 5, 2010

(86) PCT No.: PCT/JP2010/063240
§ 371 (c)(1),
(2), (4) Date: Feb. 3, 2012

(87) PCT Pub. No.: WO2011/016504
PCT Pub. Date: Feb. 10, 2011

(65) Prior Publication Data
US 2012/0142727 A1    Jun. 7, 2012

(30) Foreign Application Priority Data
Aug. 6, 2009    (JP) ................... 2009-183876

(51) Int. Cl.
| | | |
|---|---|---|
| A61K 31/472 | (2006.01) | |
| A61K 31/47 | (2006.01) | |
| A61K 31/4709 | (2006.01) | |
| A61P 25/00 | (2006.01) | |
| A61P 25/18 | (2006.01) | |
| A61P 25/28 | (2006.01) | |
| C07D 215/48 | (2006.01) | |
| C07D 215/60 | (2006.01) | |
| C07D 217/14 | (2006.01) | |
| C07D 215/54 | (2006.01) | |
| C07D 217/02 | (2006.01) | |
| C07D 217/22 | (2006.01) | |
| C07D 217/16 | (2006.01) | |
| C07D 401/04 | (2006.01) | |

(52) U.S. Cl.
CPC ............ *C07D 215/48* (2013.01); *C07D 215/54* (2013.01); *C07D 215/60* (2013.01); *C07D 217/02* (2013.01); *C07D 217/22* (2013.01); *C07D 217/16* (2013.01); *C07D 217/14* (2013.01); *C07D 401/04* (2013.01)
USPC ............ 514/307; 514/311; 514/312; 514/314; 546/144; 546/153; 546/167; 546/169

(58) Field of Classification Search
None
See application file for complete search history.

(56) References Cited

U.S. PATENT DOCUMENTS

| 6,087,304 A | 7/2000 | Brendel et al. |
| 2009/0062363 A1 | 3/2009 | Kaku et al. |

FOREIGN PATENT DOCUMENTS

| EP | 0 810 206 A1 | 12/1997 |
| EP | 1 923 387 A1 | 5/2008 |
| EP | 1 988 076 A1 | 11/2008 |
| JP | 10-81664 | 3/1998 |
| JP | 4039588 | 11/2007 |
| WO | WO 2005/082871 A2 | 9/2005 |
| WO | WO 2006/135978 A1 | 12/2006 |
| WO | WO 2007/018168 A1 | 2/2007 |
| WO | WO 2007/097197 A1 | 8/2007 |
| WO | WO 2008/096791 A1 | 8/2008 |
| WO | WO 2009/022633 A1 | 2/2009 |
| WO | WO 2009/040290 A1 | 4/2009 |
| WO | WO 2010/090304 A1 | 8/2010 |
| WO | WO 2010/090305 A1 | 8/2010 |

OTHER PUBLICATIONS

English-language International Search Report from the Japanese Patent Office in International Application No. PCT/JP2010/063240 mailed Sep. 14, 2010.

Grailhe, et al., "Increased Exploratory Activity and Altered Response to LSD in Mice Lacking the 5-$HT_{5A}$ Receptor", Neuron, vol. 22, pp. 581-591, (Mar. 1999).

(Continued)

*Primary Examiner* — Janet L Andres
*Assistant Examiner* — Timothy R Rozof
(74) *Attorney, Agent, or Firm* — Finnegan, Henderson, Farabow, Garrett & Dunner LLP

(57) ABSTRACT

[Object] An excellent agent for preventing or treating dementia, schizophrenia, and the like, based on serotonin 5-$HT_{5A}$ receptor modulating action, is provided.

[Means for Solution] It was confirmed that acylguanidine derivatives (the following formula I; any one of $Z^1$, $Z^2$, $Z^3$, $Z^4$ and $Z^5$ is nitrogen atom, and the others are carbon atoms) which have the characteristic structure in which the guanidine is bonded to one ring of the quinoline or isoquinoline via a carbonyl group, and a cyclic group is bonded to the other ring, exhibit potent 5-$HT_{5A}$ receptor modulating actions and excellent pharmacological actions based on the 5-$HT_{5A}$ receptor modulating action, and thus can be excellent agents for preventing or treating dementia, schizophrenia, bipolar disorder, or attention deficit hyperactivity disorder. Thus, the present invention has been completed.

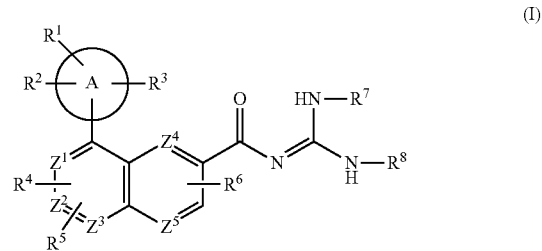

(I)

12 Claims, No Drawings

(56) References Cited

OTHER PUBLICATIONS

Pasqualetti, et al., "Distribution of the $5\text{-}HT_{5A}$ serotonin receptor mRNA in the human brain", Molecular Brain Research 56, pp. 1-8, (1998).

Birkett, et al., "Association analysis of the $5\text{-}HT_{5A}$ gene in depression, psychosis and antipsychotic response", Genetics of Nervous System Diseases, Neuroreport, vol. 11, No. 9, pp. 2017-2020, (Jun. 26, 2000).

Iwata, et al., "Association of a $5\text{-}HT_{5A}$ receptor polymorphism, Pro15Ser, to schizophrenia", Moleluar Psychiatry, pp. 217-219, (2001).

Dubertret, et al., "Family-based association studies between $5\text{-}HT_{5A}$ receptor gene and schizophrenia", Journal of Psychiatric Research 38, pp. 371-376, (2004).

Mendelson, et al., "Enhancement of Sleep by Microinjection of Triazolam into the Medial Preoptic Area", Neuropsychopharmacology, vol. 2, No. 1, pp. 61-66, (1989).

Yamazaki, et al., "FK960 N-(4-Acetyl-1-piperazinyl)-$p$-fluorobenzamide monohydrate Ameliorates the Memory Deficits in Rats through a Novel Mechanism of Action", The Journal of Pharmacology and Experimental Therapeutics, vol. 279, No. 3, pp. 1157-1173, (1996).

Ducottet, et al., "Correlations between behaviours in the elevated plus-maze and sensitivity to unpredictable subchronic mild stress: evidence from inbred strains of mice", Behavioural Brain Research 156, pp. 153-162, (2005).

NITROGENOUS-RING ACYLGUANIDINE DERIVATIVE

CROSS REFERENCE TO RELATED APPLICATIONS

This application is a national phase application based on PCT/JP2010/063240, filed Aug. 5, 2010, which claims the priority of Japanese Patent Application No. 2009-183876, filed Aug. 6, 2009, the content of both of which is incorporated herein by reference.

TECHNICAL FIELD

The present invention relates to pharmaceuticals, particularly to nitrogenous-ring acylguanidine derivatives with 5-$HT_{5A}$ receptor modulating action, useful as an agent for treating or preventing dementia, schizophrenia, and the like.

BACKGROUND ART

In recent years, it has been suggested that the 5-$HT_{5A}$ receptor which is one of the subtypes of serotonin receptors plays an important role in dementia and schizophrenia. For example, it has been reported that new exploratory behaviors are increased in the 5-$HT_{5A}$ receptor knock-out mice, and hyperactivity by LSD is inhibited in the 5-$HT_{5A}$ receptor knock-out mice (Neuron 22, 581-591, 1999). From the results of gene expression analysis, it has been reported that the 5-$HT_{5A}$ receptor is highly expressed in human and rodent brain, and in brain, it is highly expressed in hippocampal CA1 and CA3 pyramidal cells which are related to memory, and frontal lobe (cerebral cortex) which is deeply related to schizophrenia (Molecular Brain Research 56, 1-8, 1998). Furthermore, it has been reported that gene polymorphism of the 5-$HT_{5A}$ receptor relates to schizophrenia (Neuroreport 11, 2017-2020, 2000; Mol. Psychiatr. 6, 217-219, 2001; and J. Psychiatr. Res. 38, 371-376, 2004). Accordingly, it is suggested that regulation of 5-$HT_{5A}$ receptor action leads to the improvement of dementia and schizophrenia and compounds with such function are needed.

Hitherto, several kinds of compounds having affinity for a 5-$HT_{5A}$ receptor have been reported.

For example, it is described that bicyclic acylguanidine derivatives represented by the following general formula bind to the 5-$HT_{5A}$ receptor, and are thus used for treating dementia, schizophrenia, and the like (Patent Document 1).

[Chem. 1]

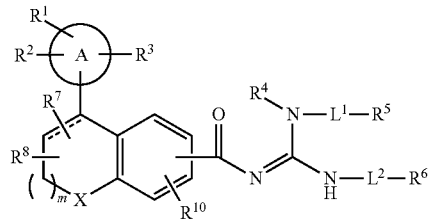

(A represents phenyl or the like, $R^1$, $R^2$, and $R^3$ each represent H, lower alkyl, halogen, or the like, $R^7$ and $R^8$ each represent H, lower alkyl, or the like, X represents O, S, or $CR^{9a}R^{9b}$, $R^{9a}$ and $R^{9b}$ each represent H or the like, the dotted line represents a bond or absence, m represents 0, 1, or 2, $L^1$ and $L^2$ each represent a bond or the like, and $R^4$, $R^5$, and $R^6$ each represent H or the like. For details, refer to the publication.)

In the publication, there is no disclosure on those in which the bicyclic ring group has a N atom containing ring.

In addition, it is reported that compounds having a tricyclic acylguanidine structure (Patent Document 2) and compounds having a structure in which the ring is directly bonded to the guanidine (Patent Document 3) each bind to the 5-$HT_{5A}$ receptor, and are used for treating dementia, schizophrenia, and the like.

Furthermore, it is described that quinoline derivatives represented by the following general formula bind to a 5-$HT_{5A}$ receptor, and are used for treating dementia, schizophrenia, and the like (Patent Document 4).

[Chem. 2]

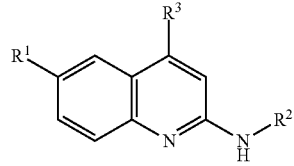

($R^1$ represents —C(O)$NR^cCH_2$—$Ar^1$ or the like, $R^2$ represents —$Ar^2$, —$CHR^d$—$Ar^2$, —$CH_2CH_2O$—$Ar^2$, or the like, $R^3$ represents phenyl or pyridinyl, which may be substituted, $Ar^1$ and $Ar^2$ each represent aryl or heteroaryl, which may be substituted, and $R^c$ and $R^d$ each represent a hydrogen atom or $C_{1-7}$-alkyl. For details on these, refer to the publication.)

In the publication, there is no disclosure on those having acylguanidine as $R^1$.

Hitherto, there is no report for a 5-$HT_{5A}$ receptor modulator which has a structure in which the guanidine is bonded to a bicyclic nitrogen-containing ring via a carbonyl group.

In addition, naphthalene ring derivatives substituted with an acylguanidino group have been reported in Patent Document 5. This document relates to a naphthylacylguanidine derivative, but does not disclose the quinoline derivative of the present invention. Further, the application of the compound of this document is an antiviral agent.

LIST OF THE DOCUMENTS

Patent Documents

Patent Document 1: WO 2009/022633 pamphlet
Patent Document 2: WO 2008/096791 pamphlet
Patent Document 3: WO 2005/082871 pamphlet
Patent Document 4: WO 2009/040290 pamphlet
Patent Document 5: WO 2006/135978 pamphlet

SUMMARY OF THE INVENTION

Problem that the Invention is to Solve

The object of the present invention is to provide excellent agents for treating or preventing dementia, schizophrenia, and the like, based on 5-$HT_{5A}$ receptor modulating action.

Means for Solving the Problem

The present inventors have extensively studied compounds having 5-$HT_{5A}$ receptor modulating action, and as a result, it has been found that acylguanidine derivatives which have the characteristic structure in which the guanidine is bonded to one ring of the quinoline or isoquinoline via a carbonyl group, and a cyclic group is bonded to the other ring, exhibit potent 5-$HT_{5A}$ receptor modulating actions and excellent pharmacological actions based on said 5-$HT_{5A}$ receptor modulating action, and thus can be excellent agents for treating or preventing dementia, schizophrenia, and the like, thereby completing the present invention.

Compound of formula (I) is characterized by the quinoline or isoquinoline structure, good metabolism profile and safety.

That is, the present invention relates to compound of formula (I) or pharmaceutically acceptable salts thereof.

[Chem. 3]

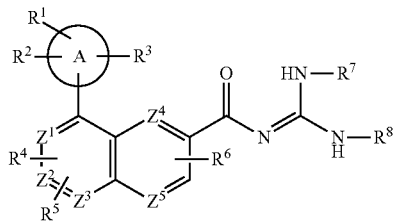

(I)

(wherein the symbols have the following meanings:

[Chem. 4]

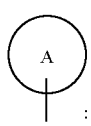

aryl, cycloalkyl, cycloalkenyl or monocyclic nitrogen-containing heterocyclic group, $Z^1, Z^2, Z^3, Z^4$ and $Z^5$: one of any of them is a nitrogen atom, and the others are carbon atoms, in which the nitrogen atom is optionally oxidized to form an N-oxide, $R^1$, $R^2$ and $R^3$: each independently represents H, lower alkyl, halogen, halogeno-lower alkyl, —CN, —$NO_2$, —$OR^a$, —S-lower alkyl, —O-halogeno-lower alkyl, —$CO_2R^a$, —C(O)$NR^bR^c$, —$SO_2$-lower alkyl, or -lower alkylene-$OR^a$, $R^4$, $R^5$ and $R^6$: each independently represents H, lower alkyl, cycloalkyl, halogen, halogeno-lower alkyl, —CN, —$NO_2$, —$OR^a$, —S-lower alkyl, —O-halogeno-lower alkyl, —$CO_2R^a$, —C(O)$NR^bR^c$, —$SO_2$-lower alkyl, or lower alkylene-$OR^a$, $R^a$, $R^b$ and $R^c$: each independently represents H or lower alkyl, and $R^7$ and $R^8$: each independently represents H or lower alkyl.)

Unless otherwise specifically noted, in the present specification, when a symbol in a chemical formula is used in another chemical formula same symbols have the same meanings.

Furthermore, atoms from $Z^1$ to $Z^5$ in formula (I), that are carbon atoms and do not bond to any of $R^4$, $R^5$, and $R^6$ are substituted with H.

Furthermore, the present invention relates to pharmaceutical compositions containing a compound of the above formula (I) or a pharmaceutically acceptable salt thereof, and a pharmaceutically acceptable excipient, and, for example, the above pharmaceutical composition which is a 5-$HT_{5A}$ receptor modulator. In another example, the present invention relates to the above pharmaceutical composition, which is an agent for preventing or treating dementia, schizophrenia, bipolar disorder, or attention deficit hyperactivity disorder; and further as another example, it relates to the above pharmaceutical composition which is an agent for preventing or treating dementia or schizophrenia.

In another embodiment, the present invention relates to 5-$HT_{5A}$ receptor modulators, for example, agents for preventing or treating dementia, schizophrenia, bipolar disorder, or attention deficit hyperactivity disorder; further as another example, it relates to use of compound of the above formula (I) or a pharmaceutically acceptable salt thereof for prevention or treatment of dementia, schizophrenia, bipolar disorder, or attention deficit hyperactivity disorder; further as another example, it relates to use of compound of the above formula (I) or a pharmaceutically acceptable salt thereof for the manufacture of an agent for preventing or treating dementia, schizophrenia, bipolar disorder, or attention deficit hyperactivity disorder or a method for preventing or treating dementia, schizophrenia, bipolar disorder, or attention deficit hyperactivity disorder, or a method for preventing or treating dementia or schizophrenia in which the method includes administering a therapeutically effective amount of compound of the above formula (I) or a pharmaceutically acceptable salt thereof to a mammal. The above said schizophrenia includes positive symptoms, negative symptoms, cognitive impairment, and mood disorders.

Effects of the Invention

Compounds of formula (I) have the advantage of potent 5-$HT_{5A}$ receptor modulating action and excellent pharmacological action based thereon. The pharmaceutical compositions of the present invention are useful for treatment or prevention of 5-$HT_{5A}$ receptor-related diseases, particularly for treatment or prevention of dementia, schizophrenia, bipolar disorder, or attention deficit hyperactivity disorder.

MODE FOR CARRYING OUT THE INVENTION

Hereinafter, the present invention is described in detail.

In the present specification, the "5-$HT_{5A}$ receptor modulator" is a generic term referring to a compound that inhibits activation of the 5-$HT_{5A}$ receptor by antagonizing with an endogenous ligand (5-$HT_{5A}$ antagonist), and a compound that shows function by activation of the 5-$HT_{5A}$ receptor (5-$HT_{5A}$ agonist). Examples of the "5-$HT_{5A}$ receptor modulating action" include a 5-$HT_{5A}$ antagonist.

The "lower alkyl" means a linear or branched alkyl group having 1 to 6 carbon atoms (hereinafter abbreviated as $C_{1-6}$), specifically, methyl, ethyl, n-propyl, isopropyl, n-butyl, isobutyl, sec-butyl, tert-butyl, n-pentyl, n-hexyl group, or the like. In another embodiment, it is $C_{1-4}$ alkyl, and in a still another embodiment, methyl, ethyl, n-propyl, or isopropyl.

The "lower alkylene" is a linear or branched $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene, and the like. In another embodiment, it is $C_{1-4}$ alkylene, in a still another embodiment, methylene or ethylene, and in a further still another embodiment, methylene.

The "cycloalkyl" is a $C_{3-10}$ saturated hydrocarbon ring group, which may have a bridge. Specifically, it is cyclopropyl, cyclobutyl, cyclopentyl, cyclohexyl, cycloheptyl, cyclooctyl, adamantyl group, or the like, in another embodiment, $C_{3-6}$ cycloalkyl group, and in a still another embodiment, cyclopropyl group.

The "cycloalkenyl" is a $C_{5-10}$ cycloalkenyl, in another embodiment, cyclopentenyl, cyclopentadienyl, cyclohexenyl, cycloheptenyl group, or the like, and in a still another embodiment, cyclopentenyl or cyclohexenyl group.

The "halogen" means F, Cl, Br, or I. In a certain embodiment, it is F or Cl.

The "halogeno-lower alkyl" is a $C_{1-6}$ alkyl group substituted with one or more halogen atoms. In a certain embodiment, it is a $C_{1-6}$ alkyl group substituted with 1 to 5 halogen atoms, and in another embodiment, difluoromethyl or trifluoromethyl group.

The "aryl" is a $C_{6-14}$ monocyclic to tricyclic aromatic hydrocarbon ring group, and in a certain embodiment, it is phenyl or naphthyl group, and in another embodiment, a phenyl group.

The "monocyclic nitrogen-containing heterocyclic group" means a 5- to 8-membered monocyclic heterocyclic group that contains one nitrogen atom, and may further contain one or two heteroatoms selected from nitrogen, oxygen, and sulfur. The "monocyclic nitrogen-containing heterocyclic group" is a generic term referring to a "monocyclic nitrogen-containing saturated heterocyclic group" that is a saturated or partially unsaturated ring group and a "monocyclic nitrogen-containing heteroaryl" that is an aromatic ring group. Sulfur or nitrogen which is a ring atom is optionally oxidized to form an oxide or a dioxide. The "monocyclic nitrogen-containing saturated heterocyclic group" is specifically azetidinyl, pyrrolidinyl, piperidyl, piperazinyl, azepanyl, diazepanyl, azocanyl, morpholinyl, thiomorpholinyl, tetrahydropyridinyl group, or the like. In another embodiment, it is pyrrolidinyl, piperidyl, or piperazinyl group, and in a still another embodiment, pyrrolidinyl group. The "monocyclic nitrogen-containing heteroaryl" is specifically pyridyl, pyrimidinyl, thiazolyl, pyrazolyl, oxadiazolyl group, or the like. In another embodiment, it is pyridyl or pyrimidinyl group, and in a still another embodiment, pyridyl group.

The expression "optionally substituted" means unsubstituted or substituted with 1 to 5 substituents. When plural substituents, these may be the same or different each other.

Some embodiments of compound of formula (I) are shown below.

(1) A compound wherein $Z^1$ is nitrogen atom, and $Z^2$, $Z^3$, $Z^4$, and $Z^5$ are carbon atoms.

(2) A compound wherein $Z^3$ is nitrogen atom, and $Z^1$, $Z^2$, $Z^4$, and $Z^5$ are carbon atoms.

(3) A compound wherein

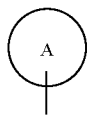

[Chem. 5]

is phenyl group, pyridyl, cyclopropyl, cyclohexenyl, cyclopentenyl, or pyrrolidinyl group, and in another embodiment, phenyl or pyridyl group. (The present ring group is hereinafter referred as ring group A.)

(4) A compound wherein $R^1$, $R^2$, and $R^3$ are each H, lower alkyl, halogen, halogeno-lower alkyl, —CN, or —OR$^a$; in another embodiment, H, lower alkyl, F, Cl, trifluoromethyl, —CN, or —OR$^a$; and in a still another embodiment, H, F, Cl, or —OR$^a$ group.

(5) A compound wherein $R^4$, $R^5$, and $R^6$ are each H, lower alkyl, cyclopropyl, halogen, halogeno-lower alkyl, —CN, or —C(O)NR$^b$R$^c$; in another embodiment, H, lower alkyl, F, Cl, halogeno-lower alkyl, —CN, or —C(O)NR$^b$R$^c$; and still in another embodiment, H, lower alkyl, F, Cl, or halogeno-lower alkyl group.

(6) A compound wherein both $R^7$ and $R^8$ are H.

(7) A compound which combines two or more groups described in the above (1) to (6).

Examples of specific embodiments of (7) above include the following compounds.

(8) A compound as described in the aforesaid (3), wherein both $R^7$ and $R^8$ are H.

(9) A compound as described in the aforesaid (3) or (8), wherein $R^1$, $R^2$, and $R^3$ are as described in the aforesaid (4).

(10) A compound as described in any one of the aforesaid (3), (8), (9), wherein $R^4$, $R^5$, and $R^6$ are as described in the aforesaid (5).

(11) A compound as described in the aforesaid (3), wherein $Z^1$ is a nitrogen atom, and $Z^2$, $Z^3$, $Z^4$, and $Z^5$ are carbon atoms.

(12) A compound as described in the aforesaid (3), wherein $Z^3$ is a nitrogen atom, and $Z^1$, $Z^2$, $Z^4$, and $Z^5$ are carbon atoms.

(13) A compound as described in the aforesaid (11) or (12), wherein both $R^7$ and $R^8$ are H.

(14) A compound as described in any one of the aforesaid (11) to (13), wherein $R^1$, $R^2$, and $R^3$ are as described in the aforesaid (4).

(15) A compound as described in any one of the aforesaid (11) to (14), wherein $R^4$, $R^5$, and $R^6$ are as described in (5) above.

(16) A compound wherein $Z^1$ is a nitrogen atom; $Z^2$, $Z^3$, $Z^4$, and $Z^5$ are carbon atoms; the ring group A is phenyl, pyridyl, cyclopropyl, cyclohexenyl, cyclopentenyl, or pyrrolidinyl group; $R^1$, $R^2$, and $R^3$ are each H, lower alkyl, halogen, halogeno-lower alkyl, —CN, or —OR$^a$; $R^4$, $R^5$, and $R^6$ are each H, lower alkyl, cyclopropyl, halogen, halogeno-lower alkyl, —CN, or —C(O)NR$^b$R$^c$; and $R^7$ and $R^8$ are both H.

(17) A compound wherein $Z^3$ is a nitrogen atom; $Z^1$, $Z^2$, $Z^4$, and $Z^5$ are carbon atoms; the ring group A is phenyl, pyridyl, cyclopropyl, cyclohexenyl, cyclopentenyl, or pyrrolidinyl group; $R^1$, $R^2$, and $R^3$ are each H, lower alkyl, halogen, halogeno-lower alkyl, —CN, or —OR$^a$; $R^4$, $R^5$, and $R^6$ are each H, lower alkyl, cyclopropyl, halogen, halogeno-lower alkyl, —CN, or —C(O)NR$^b$R$^c$; and both $R^7$ and $R^8$ are H.

(18) A compound wherein $Z^1$ is a nitrogen atom; $Z^2$, $Z^3$, $Z^4$, and $Z^5$ are carbon atoms; the ring group A is phenyl or pyridyl group; $R^1$, $R^2$, and $R^3$ are each H, F, Cl, or a OR$^a$ group; $R^4$, $R^5$, and $R^6$ are each H, lower alkyl, F, Cl, or a halogeno-lower alkyl group; and both $R^7$ and $R^8$ are H.

(19) A compound wherein $Z^3$ is a nitrogen atom; $Z^1$, $Z^2$, $Z^4$, and $Z^5$ are carbon atoms; the ring group A is phenyl or pyridyl group; $R^1$, $R^2$, and $R^3$ are each H, F, Cl, or —OR$^a$ group; $R^4$, $R^5$, and $R^6$ are each H, lower alkyl, F, Cl, or a halogeno-lower alkyl group; and both $R^7$ and $R^8$ are H.

(20) A compound or a salt thereof, which is selected from the group consisting of:

N-(diaminomethylene)-2-methyl-4-(2,4,6-trifluorophenyl)quinoline-6-carboxamide, 1-(2-chloro-6-fluorophenyl)-N-(diaminomethylene)-4-fluoroisoquinoline-7-carboxamide, N-(diaminomethylene)-1-(2,6-difluorophenyl)-4-fluoroisoquinoline-7-carboxamide, 1-(2-chloro-4-fluorophenyl)-N-(diaminomethylene)-4-fluoroisoquinoline-7-carboxamide, N-(diaminomethylene)-4-methyl-1-(2,4,6-trifluorophenyl)isoquinoline-7-carboxamide, N-(diaminomethylene)-2,3-dimethyl-4-(2,4,6-trifluorophenyl)quinoline-6-carboxamide, N-(diaminomethylene)-1-(3,5-difluoropyridin-4-yl)-4-fluoroisoquinoline-7-carboxamide, N-(diaminomethylene-4-fluoro-1-(2-fluoro-6-methoxyphenyl)isoquinoline-7-carboxamide, N-(diaminomethylene)-4-fluoro-1-(2-fluorophenyl)isoquinoline-7-carboxamide, 1-(2-chlorophenyl)-N-(diaminomethylene)-4-fluoroisoquinoline-7-carboxamide, 4-chloro-N-(diaminomethylene)-1-(2,6-difluorophenyl)isoquinoline-7-carboxamide, 1-(3-chloro-5-fluoropyridin-4-yl)-N-(diaminomethylene)-4-fluoroisoquinoline-7-carboxamide, N-(diaminomethylene)-1-(2,6-difluorophenyl)-4-methylisoquinoline-7-carboxamide, 1-(3-chloro-5-fluoropyridin-2-yl)-N-(diaminomethylene)-4-fluoroisoquinoline-7-carboxamide, N-(diaminomethylene)-4-(difluoromethyl)-1-(2,6-difluorophenyl)isoquinoline-7-carboxamide, N-(diaminomethylene)-1-(2-fluorophenyl)-4-methylisoquinoline-7-carboxamide, and 4-chloro-N-(diaminomethylene)-1-(2,4-difluorophenyl)isoquinoline-7-carboxamide.

Furthermore, compound of formula (I) may exist as other tautomers, conformational isomers, or optical isomers, depending on the kinds of substituents. In the present specification, compound of formula (I) shall be described in only one form of the isomers, yet the present invention includes such isomers, their isolated forms or their mixtures. For example, among the compounds (I), compounds having lower alkyl as $R^7$ or $R^8$ may exist as isomers having different positions of double bonds and geometrical arrangement in the guanidine moiety. The present invention includes all of these isomers.

Furthermore, pharmaceutically acceptable prodrugs of compound of formula (I) are also included in the present invention. Pharmaceutically acceptable prodrugs refer to compounds which have a group that can be converted into an amino group, OH, $CO_2H$, or the like by solvolysis or under physiological conditions. Examples of groups forming prodrugs include the groups described in "Prog. Med., 5, 2157-2161 (1985), and "Iyakuhin no Kaihatsu (Development of Medicines)" (Hirokawa Publishing company, 1990), vol. 7, *Bunshi Sekkei* (Molecular Design)", 163-198.

Furthermore, compound of formula (I) may form an acid addition salt, or may form a salt with a base depending on the kind of substituents, and the salts are included in the present invention as long as they are pharmaceutically acceptable salts. Specifically, examples of these salts include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, and glutamic acid, salts with inorganic bases such as sodium, potassium, magnesium, calcium, and aluminum, and organic bases such as methylamine, ethylamine, ethanolamine, lysine, and ornithine, and ammonium salts.

In addition, compound of formula (I) and pharmaceutically acceptable salts thereof include hydrates, solvates, and crystal polymorphs. Also, compound of formula (I) and pharmaceutically acceptable salts thereof include the compounds labeled with radioactive or non-radioactive isotopes.

(Production Processes)

Compound of formula (I) and pharmaceutically acceptable salts thereof can be produced by applying known synthetic methods, according to its basic skeleton or kind of substituents. Protection of the functional groups with suitable protecting groups (groups which can be easily converted into the original functional group) may be effective in technical means, depending on the kind of the functional group, in any step from starting materials to intermediates. Examples of functional groups include amino group, hydroxyl group, and carboxyl group, and examples of the protecting group include those described in "Greene's Protective Groups in Organic Synthesis ($4^{th}$ Edition, 2006)", edited by P. G. M. Wuts and T. W. Greene, which can be selected and used depending on the reaction conditions. In this way, the object compound can be obtained by introducing a protecting group during the reaction, and then, by optionally removing it.

In addition, prodrugs of compound of formula (I) can be produced by introducing a specific group during any step from starting materials to intermediates, in a similar way to the aforementioned protecting groups, or by carrying out further reactions using the obtained compound of formula (I). The reaction can be carried out by employing known methods to a skilled person in the art, such as usual esterification, amidation, and dehydration reactions.

Hereinbelow, representative production processes of compound of formula (I) are described. Each production process can be carried out according to the references cited in the description. Further, production processes of the present invention are not limited to the examples as shown below.

(Production Process 1)

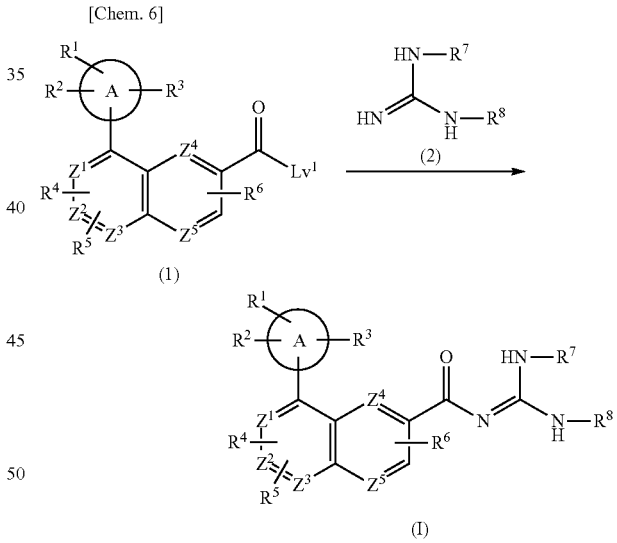

($Lv^1$ Represents —OH or a Leaving Group.)

Compound of formula (I) can be produced by the reaction of a carboxylic acid or a reactive derivative thereof (1) with guanidine (2) or a salt thereof.

The reaction can be carried out by using the carboxylic acid or a reactive derivative thereof (1) and guanidine (2) in equivalent amounts, or guanidine in an excess amount. It can be carried out under cooling to under heating, and preferably at −20° C. to 80° C., in a solvent inert to the reaction, such as aromatic hydrocarbons such as benzene, toluene, xylene, and the like; halogenated hydrocarbons such as dichloromethane, 1,2-dichloroethane, chloroform, and the like; ethers such as diethylether, tetrahydrofuran (THF), dioxane, dimethoxyethane (DME), and the like; N,N-dimethylformamide (DMF), dimethylsulfoxide (DMSO), N-methylpyrrolidone (NMP), ethyl acetate, acetonitrile, water, and the like, or a mixtures thereof.

When a carboxylic acid wherein $Lv^1$ is —OH is used as the carboxilic acid or a reactive derivative thereof (1), it is desirable to carry out the reaction in the presence of a condensing agent. In this case, examples of the condensing agent include N,N'-dicyclohexylcarbodiimide (DCC), 1-[3-(dimethylamino)propyl]-3-ethylcarbodiimide (WSC), 1,1'-carbonyldiimidazole (CDI), 2-(1H-benzotriazol-1-yl)-1,1,3,3-tetramethyluronium hexafluorophosphate (HBTU), diphenylphosphoryl azide (DPPA), and phosphorous oxychloride. In some cases, it is preferable to further use additive agents (e.g., N-hydroxysuccinimide (HONSu), 1-hydroxybenzotriazole (HOBt) and the like). The condensing agent is usually used in an equivalent amount or excess to the carboxylic acid.

When a reactive derivative of the carboxylic acid wherein $Lv^1$ is a leaving group is used as the carboxylic acid or a reactive derivative thereof (1), acid halides (acid chloride, acid bromide, or the like), acid anhydrides (mixed acid anhydrides obtained by the reaction of the carboxylic acid with phenyl chlorocarbonate, p-toluenesulfonic acid, isovaleric acid, or the like; or symmetric acid anhydrides), active esters (esters which can be prepared from phenol, HOBt, HONSu, or the like; optionally substituted with an electron withdrawing group such as a nitro group, a fluorine atom, and the like), lower alkyl esters, and the like can be exemplified. Each of which can be produced from carboxylic acid using reactions obvious to those skilled in the art. Depending on the kind of the reactives, it is sometimes advantageous for quick progress of the reaction to carry out the reaction in presence of a base (organic bases such as triethylamine, diisopropylethylamine (DIPEA), N-methylmorpholine, pyridine, 4-(N,N-dimethylamino)pyridine, and the like, or inorganic bases such as sodium hydrogen carbonate and the like). Pyridine can also serve as a solvent. Further, when a lower alkyl ester is used as the reactive derivative, it is preferable to carry out the reaction under from room temperature to heating under reflux.

(Production Process 2)

[Chem. 7]

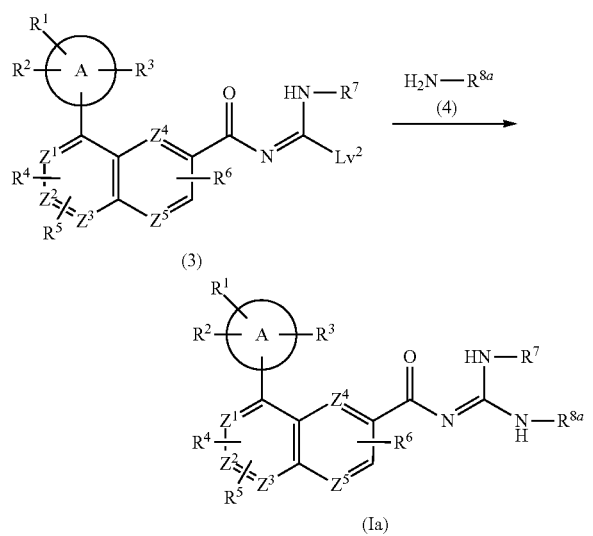

(Ia)

($Lv^2$ represents a leaving group such as pyrazol-1-yl optionally substituted with lower alkyl, or —S-lower alkyl, —O-phenyl, —Br, —Cl, and the like, and $R^{8a}$ represents lower alkyl.)

Compound (Ia) having lower alkyl as $R^8$ among compounds of formula (I) can be produced by reaction of an amidine compound (3) having a leaving group with an amine compound (4).

This reaction can be carried out using compound (3) and compound (4) in equivalent amounts, or in an excess amount of one of them, in which their mixture is stirred under from cooling to heating under reflux, and preferably from 0° C. to 80° C., usually for 0.1 hours to 5 days, in a solvent inert to reaction or without solvent. Examples of solvents used herein are not limited, but include aromatic hydrocarbons, ethers, halogenated hydrocarbons, DMF, DMSO, ethyl acetate, acetonitrile, and a mixture thereof. It is sometimes advantageous for smooth progress of the reaction to carry out the reaction in the presence of organic bases such as triethylamine, N,N-diisopropylethylamine, N-methylmorpholine, and the like, or inorganic bases such as potassium carbonate, sodium carbonate, potassium hydroxide, and the like.

Carboxylic acid or a reactive derivative thereof (1) of the above Production Process 1 can be produced by known methods or any variation thereof. For example, starting compound (1a) can be produced by the reaction route shown below (Production Process of Starting Compound).

(Production Process of Starting Compound)

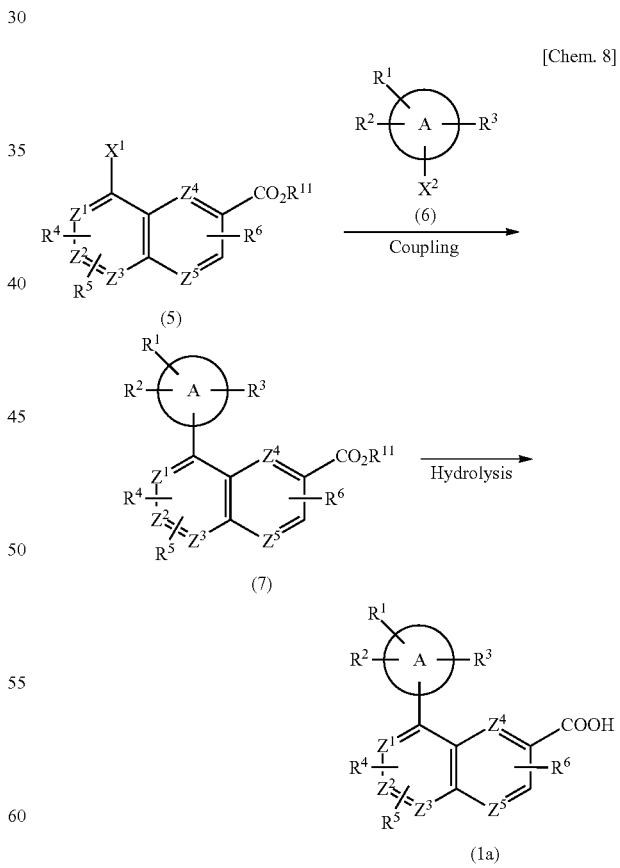

(In the formula, $X^1$ represents halogen, methanesulfonyloxy group, p-toluenesulfonyloxy group, or trifluoromethanesulfonyloxy group, $R^{11}$ represents a protecting group of carboxyl group such as lower alkyl, benzyl, or the like, and $X^2$ represents an active group such as —B(OH)$_2$, —B(OY)OW, and the like. Here, Y and W are the same or different from each other and represent lower alkyl, or Y and W are combined together to form lower alkylene.)

Compound (1a) can be obtained by coupling reaction of compound (5) and compound (6) to first obtain compound (7), followed by its hydrolysis.

Synthesis of compound (7) is carried out by using a mixture of compound (5) and compound (6) in equivalent amounts or in an excess of one of them, and stirring the mixture under from room temperature to heating under reflux, usually for 0.1 hours to 5 days, in a reaction inert solvent in the presence of a base and palladium catalyst. The present reaction is preferably carried out under an inert gas atmosphere. Examples of solvents used herein include, but not particularly limited to, aromatic hydrocarbons, ethers, halogenated hydrocarbons, alcohols such as methanol, ethanol, and the like, DMF, DMSO, and mixed solvents thereof. As bases, inorganic bases such as sodium carbonate, potassium carbonate, sodium hydroxide, and the like are preferred. Examples of the palladium catalyst include tetrakis(triphenylphosphine)palladium, dichlorobis(triphenylphosphine)palladium, palladium-1,1'-bis(diphenylphosphino)ferrocene chloride, tris(dibenzylideneacetone)dipalladium, and the like. As palladium ligands, tert-butylphosphine, cyclohexylphosphine, 2-dicyclohexylphosphinobiphenyl derivative, or the like can be used.

The coupling reaction can be carried out with reference to the following documents.

[Documents]

A. de Meijere and F. Diederich, "Metal-Catalyzed Cross-Coupling Reactions", 2nd edition, VCH Publishers Inc., 2004

The Chemical Society of Japan, "Courses in Experimental Chemistry (5$^{th}$ edition)" Vol. 13 (2005) (Maruzen)

Subsequently, compound (7) can be subjected to hydrolysis reaction to obtain compound (1a). The hydrolysis reaction can be carried out with reference to "Greene's Protective Groups in Organic Synthesis (4$^{th}$ edition, 2006)" shown above.

(Other Production Processes)

In addition, compounds (5) and (6) described above in (Production Process of Starting Compound) can be produced by known methods or any variation thereof, and for example, they can be produced by the methods described in Preparation Examples below.

Compound of formula (I) prepared in accordance with the aforementioned methods is isolated and purified as a free compound, as a pharmaceutically acceptable salt, hydrate, solvate, or crystalline polymorph thereof. Pharmaceutically acceptable salts of compound of formula (I) can be prepared using salt preparation methods well-known to those skilled in the art.

Isolation and purification are carried out by applying common chemical operations such as extraction, fractional crystallization and fractional chromatography.

A variety of isomers can be produced by selecting their corresponding starting compounds or by separation of isomers using their physicochemical properties differences. For example, optical isomers are obtained by general optical resolution methods of racemic compounds (for example, fractional crystallization of diastereomeric salts obtained from optically active bases or acids; or chiral column chromatography), and also can be prepared from suitable optical active starting compounds.

EXAMPLES

Hereinafter, production processes of compound of formula (I) are described as Examples. In addition, production processes of compounds used as starting compounds are described as Preparation Examples. Production processes of compound of formula (I) are not limited to the production processes of the following specific Examples, but the compounds can be prepared by combining these production processes or known production processes.

Preparation Example 1

A mixture of 4-(2,4,6-trifluorophenyl)quinoline-6-carboxylic acid (118 mg), WSC hydrochloride (112 mg), HOBt (37 mg), and DMF (4 mL) was stirred at room temperature for 5 minutes, and then 3,5-dimethyl-1H-pyrazole-1-carboximidamide nitrate (94 mg) and DIPEA (76 mg) were added thereto, followed by stirring for an additional 24 hours. The reaction mixture was diluted with water, and the precipitate was collected by filtration to obtain N-[1-amino(3,5-dimethyl-1H-pyrazol-1-yl)methylene]-4-(2,4,6-trifluorophenyl)quinoline-6-carboxamide (140 mg).

Preparation Example 2

A mixture of methyl 1-(2,4,6-trifluorophenyl)isoquinoline-7-carboxylate (228 mg), a 1M aqueous sodium hydroxide solution (4 mL), THF (3 mL), and ethanol (3 mL) was stirred at room temperature for 24 hours. The reaction mixture was neutralized with 1M hydrochloric acid, and the precipitate was collected by filtration to obtain 1-(2,4,6-trifluorophenyl)isoquinoline-7-carboxylic acid hydrochloride (200 mg).

Preparation Example 3

2-Carbamoyl-4-(2,4,6-trifluorophenyl)quinoline-6-carboxylic acid was obtained by the same reaction as in Preparation Example 2 by using methyl 2-cyano-4-(2,4,6-trifluorophenyl)quinoline-6-carboxylate as the starting material.

Preparation Example 4

Under argon gas atmosphere, a mixture of methyl 1-{[(trifluoromethyl)sulfonyl]oxy}isoquinoline-7-carboxylate (250 mg), 2,4,6-trifluorophenylboric acid (184 mg), tetrakis(triphenylphosphine)palladium (22 mg), triethylamine (189 mg), and 1,4-dioxane (15 mL) was heated under stirring in an oil bath at 95° C. for 18 hours. The reaction mixture was returned to room temperature, diluted with water, and then extracted with ethyl acetate. The organic layer was concentrated under reduced pressure, and the resulting residue was purified under silica gel column chromatography (hexane/ethyl acetate) to obtain methyl 1-(2,4,6-trifluorophenyl)isoquinoline-7-carboxylate (228 mg).

Preparation Example 5

Under argon gas atmosphere, a mixture of methyl 4-bromo-3-chloroquinoline-6-carboxylate (130 mg), 2,4-difluorophenylboric acid (137 mg), a 1,1'-bis(diphenylphosphino)ferrocene palladium (H) dichloride/dichloromethane complex (177 mg), cesium fluoride (197 mg), 1,4-dioxane (8 mL), and water (2 mL) was heated under stirring in an oil bath at 100° C. for one day. The reaction mixture was returned to room temperature, and water was added, and extracted with ethyl acetate. The organic layer was concentrated under reduced pressure, and the resulting residue was purified under silica gel column chromatography (hexane/ethyl acetate) to obtain methyl 3-chloro-4-(2,4-difluorophenyl)quinoline-6-carboxylate (100 mg).

Preparation Example 6

Under argon gas atmosphere, a mixture of methyl 4-bromo-1-(2,4,6-trifluorophenyl)isoquinoline-7-carboxylate (292 mg), 2,4,6-trivinylboroxin-pyridine complex (89 mg), palladium acetate (19 mg), tricyclohexylphosphine (45 mg), tripotassium phosphate (280 mg), toluene (7 mL), and water (0.5 mL) was heated under stirring in an oil bath at 100° C. for 12 hours. The reaction mixture was returned to room temperature, diluted with water and ethyl acetate, and then the insoluble materials were separated by filtration. The filtrate was extracted with ethyl acetate, and the organic layer was concentrated under reduced pressure. The resulting residue was purified under silica gel column chromatography (hexane/ethyl acetate) to obtain methyl 1-(2,4,6-trifluorophenyl)-4-vinylisoquinoline-7-carboxylate (180 mg).

Preparation Example 7

Under argon gas atmosphere, a mixture of methyl 4-bromo-1-(2,4,6-trifluorophenyl)isoquinoline-7-carboxylate (160 mg), trimethylboroxin (117 mg), tetrakis(triphenylphosphine)palladium (23 mg), 2M aqueous sodium carbonate solution (1 mL), and 1,4-dioxane (5 mL) was heated under stirring in an oil bath at 100° C. for 4 hours. The reaction mixture was returned to room temperature and diluted with ethyl acetate, and then the insoluble materials were separated by filtration through Celite. The filtrate was extracted with ethyl acetate. The organic layer was concentrated under reduced pressure, and the resulting residue was purified under silica gel column chromatography (hexane/ethyl acetate) to obtain 4-methyl-1-(2,4,6-trifluorophenyl)isoquinoline-7-carboxylic acid (95 mg).

Preparation Example 8

Under argon gas atmosphere, a mixture of ethyl 5-bromoquinoline-3-carboxylate (113 mg), 2,4,6-trifluorophenylboric acid (106 mg), bis(tri-t-butylphosphine)palladium (41 mg), cesium fluoride (123 mg), silver oxide (112 mg), and DMF (2 mL) was heated under stirring in an oil bath at 100° C. for 15 hours. The reaction liquid was returned to room temperature, diluted with water, and then extracted with ethyl acetate. The organic layer was concentrated under reduced pressure, and the resulting residue was purified under silica gel column chromatography (hexane/ethyl acetate) to obtain ethyl 5-(2,4,6-trifluorophenyl)quinoline-3-carboxylate (60 mg).

Preparation Example 9

Under argon gas atmosphere, n-butyllithium (1.6 M THF solution, 0.7 mL) was added dropwise to a mixture of 3,5-difluoropyridine (123 mg) and THF (3 mL) at −78° C., followed by stirring at the same temperature for one hour. Then, zinc chloride (146 mg) was added, and stirred for an additional hour. Methyl 4-chloro-1-{[(trifluoromethyl)sulfonyl]oxy}isoquinoline-7-carboxylate (330 mg) and tetrakis(triphenylphosphine)palladium (206 mg) were added thereto, followed by heating under stirring in an oil bath at 60° C. for 3 hours. The reaction mixture was concentrated under reduced pressure and purified under silica gel column chromatography (hexane/ethyl acetate) to obtain methyl 4-chloro-1-(3,5-difluoropyridin-4-yl)isoquinoline-7-carboxylate (62 mg).

Preparation Example 10

Under argon gas atmosphere, n-butyllithium (1.6 M THF solution, 1.3 mL) was added dropwise to a mixture of 3,5-difluoropyridine (238 mg) and THF (4 mL) at −78° C., followed by stirring at the same temperature for one hour. Then, zinc chloride (0.5 M THF solution, 3.8 mL) was slowly added stirried at the same temperature for 30 minutes and further for an additional hour at room temperature. Tris(dibenzylideneacetone)dipalladium (73 mg), 2-dicyclohexylphosphino-2',6'-diisopropoxybiphenyl (148 mg), and ethyl 2,3-dimethyl-4-{[(trifluoromethyl)sulfonyl]oxy}quinoline-6-carboxylate (300 mg), were added to the reaction mixture and heated under stirring in an oil bath at 70° C. for 15 hours. The reaction mixture was returned to room temperature, and the insoluble materials were separated by filtration. Then, the precipitate was concentrated under reduced pressure, and the resulting residue was purified under silica gel column chromatography (hexane/ethyl acetate) to obtain ethyl 4-(3,5-difluoropyridin-4-yl)-2,3-dimethylquinoline-6-carboxylate (51 mg).

Preparation Example 11

Trifluoromethanesulfonic anhydride (2.1 g) was added to a mixture of methyl 1-hydroxyisoquinoline-7-carboxylate (1.3 g), pyridine (587 mg), and dichloromethane (40 mL), followed by stirring at room temperature for 18 hours. The reaction mixture was diluted with water, extracted with chloroform, and the organic layer was concentrated under reduced pressure. The resulting residue was purified under silica gel column chromatography (chloroform/methanol) to obtain methyl 1-{[(trifluoromethyl)sulfonyl]oxy}isoquinoline-7-carboxylate (1.9 g).

Preparation Example 12

Boron tribromide (1M dichloromethane solution, 2.5 mL) was added to a mixture of methyl 4-fluoro-1-(2-fluoro-6-methoxyphenyl)isoquinoline-7-carboxylate (270 mg) and dichloromethane (3 mL) under ice-cooling, and stirred at room temperature for 16 hours. The reaction mixture was diluted with water, and the precipitate was collected by filtration to obtain 4-fluoro-1-(2-fluoro-6-hydroxyphenyl)isoquinoline-7-carboxylic acid (240 mg).

Preparation Example 13 m-Chloroperbenzoic acid (425 mg) was added to a mixture of methyl 4-(2,4,6-trifluorophenyl)quinoline-6-carboxylate (710 mg) and dichloromethane (20 mL), followed by stirring at room temperature for 3 days. The reaction mixture was diluted with aqueous sodium thiosulfate solution, and extracted with chloroform. The organic layer was washed with water, dried, and concentrated under reduced pressure to obtain methyl 4-(2,4,6-trifluorophenyl)quinoline-6-carboxylate 1-oxide (680 mg).

Preparation Example 14

A mixture of methyl 3,4-dichloroquinoline-6-carboxylate (100 mg), pyrrolidine (33 mg), and NMP (2 mL) was heated under stirring at 180° C. for 10 minutes under microwave irradiation. The reaction mixture was diluted with water, and extracted with ethyl acetate. The organic layer was concentrated under reduced pressure, and the resulting residue was purified under silica gel column chromatography (hexane/ethyl acetate) to obtain methyl 3-chloro-4-(pyrrolidin-1-yl)quinoline-6-carboxylate (40 mg).

Preparation Example 15

Sodium borohydride (17 mg) was added to a mixture of methyl 4-formyl-1-(2,4,6-trifluorophenyl)isoquinoline-7-carboxylate (150 mg) and methanol (10 mL) under ice-cooling, followed by stirring at room temperature for 10 minutes. The reaction mixture was diluted with water, and extracted with ethyl acetate. The organic layer was washed with water, dried, and then concentrated under reduced pressure to obtain methyl 4-(hydroxymethyl)-1-(2,4,6-trifluorophenyl)isoquinoline-7-carboxylate (140 mg).

Preparation Example 16

Osmium tetraoxide (2.5% isobutanol solution, 0.05 mL), sodium periodate (280 mg), and water (4 mL) were added to a mixture of methyl 1-(2,4,6-trifluorophenyl)-4-vinylisoquinoline-7-carboxylate (180 mg) and THF (4 mL), followed by stirring at room temperature for 12 hours. The reaction mixture was diluted with an aqueous sodium sulfite solution, and extracted with ethyl acetate. The organic layer was concentrated under reduced pressure and purified by silica gel column chromatography (hexane/ethyl acetate) to obtain methyl 4-formyl-1-(2,4,6-trifluorophenyl)isoquinoline-7-carboxylate (153 mg).

Preparation Example 17

Under hydrogen gas atmosphere at 1 atm, a mixture of methyl 1-(2,6-difluorophenyl)-4-(prop-1-en-2-yl)isoquinoline-7-carboxylate (85 mg), 10% palladium-active carbon (20 mg), and methanol was stirred at room temperature for 4 days. The insoluble materials were separated by filtration, and then the filtrate was concentrated under reduced pressure. The resulting residue was purified under silica gel column chromatography (chloroform) to obtain methyl 1-(2,6-difluorophenyl)-4-isopropyl isoquinoline-7-carboxylate (72 mg).

Preparation Example 18

A mixture of methyl 4-bromo-1-(2,4,6-trifluorophenyl)isoquinoline-7-carboxylate (66 mg), zinc cyanide (content 60%, 21 mg), tris(dibenzylideneacetone)dipalladium (0) (14 mg), 1,1'-bis(diphenylphosphino)ferrocene (17 mg), and N-methyl-2-pyrrolidone (3 mL) was heated under stirring in an oil bath at 150° C. for 3 hours. The reaction mixture was returned to room temperature, diluted with water and ethyl acetate, and then the insoluble materials were separated by filtration. The filtrate was subjected to liquid separation, and the organic layer was concentrated under reduced pressure. Then, the resulting residue was purified under silica gel column chromatography (hexane/ethyl acetate) to obtain methyl 4-cyano-1-(2,4,6-trifluorophenyl)isoquinoline-7-carboxylate (44 mg).

Preparation Example 19

A mixture of methyl-1-oxide 4-(2,4,6-trifluorophenyl)quinoline-6-carboxylate (540 mg), trimethylsilyl cyanide (530 mg), triethylamine (607 mg), dichloromethane (10 mL), and acetonitrile (20 mL) was heated under reflux for one day. The reaction mixture was returned to room temperature, diluted with saturated aqueous sodium bicarbonate, and extracted with ethyl acetate. The organic layer was concentrated under reduced pressure, and the resulting residue was purified under silica gel column chromatography (hexane/ethyl acetate) to obtain methyl 2-cyano-4-(2,4,6-trifluorophenyl)quinoline-6-carboxylate (460 mg).

Preparation Example 20

A mixture of methyl 1-hydroxy-3-methylisoquinoline-7-carboxylate (120 mg), Selectfluor (registered trademark) (215 mg), acetonitrile (2 mL), and methanol (2 mL) was stirred at room temperature for 3 days. The reaction mixture was concentrated under reduced pressure, and the resulting residue was diluted with water. Then, the precipitate was collected by filtration to obtain methyl 4-fluoro-1-hydroxy-3-methylisoquinoline-7-carboxylate (55 mg).

Preparation Example 21

DEOXO-FLUOR (registered trademark) (240 mg) was added dropwise to a mixture of methyl 1-(2,6-difluorophenyl)-4-formylisoquinoline-7-carboxylate (96 mg) and dichloromethane (5 mL) at 0° C., and stirred at room temperature for one hour. The reaction mixture was diluted with saturated aqueous sodium bicarbonate, and extracted with chloroform. The organic layer was concentrated under reduced pressure and purified by silica gel column chromatography (hexane/ethyl acetate) to obtain methyl 4-(difluoromethyl)-1-(2,6-difluorophenyl)isoquinoline-7-carboxylate (80 mg).

Preparation Example 22

A mixture of methyl 4-hydroxyquinoline-6-carboxylate (2.07 g), N-chlorosuccinimide (1.36 g), and acetic acid (56 mL) was stirred at room temperature for one day. The reaction mixture was diluted with water, and then, the precipitate was collected by filtration to obtain methyl 3-chloro-4-hydroxyquinoline-6-carboxylate (2.13 g).

Preparation Example 23

Methyl 4-chloro-1-hydroxyisoquinoline-7-carboxylate was prepared by the same reaction as in Preparation Example 22 using methyl 1-hydroxyisoquinoline-7-carboxylate as the starting material.

Preparation Example 24

A mixture of ethyl 3-chloro-4-hydroxy-2-methylquinoline-6-carboxylate (629 mg) and phosphoryl chloride (2 mL) was stirred in an oil bath at 100° C. for 18 hours. The reaction mixture was concentrated under reduced pressure, and the resulting residue was diluted with water, and extracted with ethyl acetate. The organic layer was concentrated under reduced pressure, and the resulting residue was purified under silica gel column chromatography (hexane/ethyl acetate) to obtain ethyl 3,4-dichloro-2-methylquinoline-6-carboxylate (454 mg).

Preparation Example 25

A mixture of methyl 4-(2,4,6-trifluorophenyl)quinoline-6-carboxylate 1-oxide (1.3 g) and phosphoryl chloride (10 mL)

was heated under stirring in an oil bath at 100° C. for 2 hours. The reaction mixture was concentrated under reduced pressure, and the resulting residue was diluted with water, and then extracted with ethyl acetate. The organic layer was concentrated under reduced pressure, and the resulting residue was purified under silica gel column chromatography (hexane/ethyl acetate) to obtain methyl 2-chloro-4-(2,4,6-trifluorophenyl)quinoline-6-carboxylate (370 mg).

Preparation Example 26

A mixture of bromine (940 mg) and acetic acid (10 mL) was added dropwise to a mixture of methyl 1-hydroxyisoquinoline-7-carboxylate (1.2 g) and acetic acid (50 mL) and stirred at room temperature for 30 minutes. The reaction mixture was diluted with water, and the precipitate was collected by filtration to obtain methyl 4-bromo-1-hydroxyisoquinoline-7-carboxylate (1.4 g).

Preparation Example 27

A mixture of methyl 3-chloro-4-hydroxyquinoline-6-carboxylate (600 mg) and phosphoryl bromide (868 mg) was heated under stirring in an oil bath at 130° C. for 6 hours. Ice-water was added, followed by neutralization with saturated aqueous sodium bicarbonate and extraction with ethyl acetate. The organic layer was washed with water, dried, and concentrated under reduced pressure to obtain methyl 4-bromo-3-chloroquinoline-6-carboxylate (426 mg).

Preparation Example 28

To a mixture of methyl 1-hydroxyisoquinoline-7-carboxylate (1.0 g) and pyridine (40 mL) was added iodine (1.2 g), and stirred at room temperature for 16 hours. The reaction mixture was diluted with saturated aqueous sodium bicarbonate and a 5% aqueous sodium thiosulfate solution. Then, the precipitate was collected by filtration to obtain methyl 1-hydroxy-4-iodoisoquinoline-7-carboxylate (1.1 g).

Preparation Example 29

To a mixture of methyl 4-oxo-1,4-dihydroquinoline-6-carboxylate (1.1 g) and acetic acid (30 mL) was added N-iodosuccinimide (1.1 g), followed by stirring at room temperature for one day. The reaction mixture was diluted with water, and the precipitate was collected by filtration to obtain methyl 3-iodo-4-oxo-1,4-dihydroquinoline-6-carboxylate (1.8 g).

Preparation Example 30

Methyl 2,2-difluoro-2-(fluorosulfonyl)acetate (1.7 g) and copper(I) iodide (174 mg) were added to a mixture of methyl 3-iodo-4-oxo-1,4-dihydroquinoline-6-carboxylate (1.0 g) and DMF (20 mL), followed by heating under stirring in an oil bath at 100° C. for 5 hours. The reaction mixture was returned to room temperature, concentrated under reduced pressure, and then the resulting residue was purified under silica gel column chromatography (chloroform/methanol) to obtain methyl 4-oxo-3-(trifluoromethyl)-1,4-dihydroquinoline-6-carboxylate (228 mg).

Preparation Example 31

A mixture of methyl 3-methyl-1-oxo-1H-isochromene-7-carboxylate (1.0 g), 29% aqueous ammonia solution (30 mL) and THF (30 mL) was stirred at room temperature for 8 hours. The reaction mixture was neutralized with hydrochloric acid, and the precipitate was collected by filtration to obtain methyl 1-hydroxy-3-methylisoquinoline-7-carboxylate (390 mg).

Preparation Example 32

Concentrated sulfuric acid (3 mL) was added to a mixture of sodium 3-methyl-1-oxo-1H-isochromene-7-carboxylate (1.69 g) and methanol (50 mL), and heated under stirring in an oil bath at 60° C. for 2 days. The reaction mixture was returned to room temperature, diluted with water, and extracted with ethyl acetate. The organic layer was washed with water, dried, and concentrated under reduced pressure to obtain methyl 3-methyl-1-oxo-1H-isochromene-7-carboxylate (1.0 g).

Preparation Example 33

Under oxygen atmosphere, a mixture of 4-allyl isophthalic acid (500 mg), bis(acetonitrile)dichloropalladium (629 mg), sodium carbonate (514 mg), and THF (30 mL) was stirred at room temperature for 4 hours. The insoluble material of the reaction mixture was separated by filtration, and the filtrate was concentrated under reduced pressure. A mixture of the resulting residue and DMF (5 mL) was diluted with 1M hydrochloric acid, and the precipitate was collected by filtration to obtain 3-methyl-1-oxo-1H-isochromene-7-carboxylic acid (112 mg).

Preparation Example 34

Under argon gas atmosphere, a mixture of dimethyl 4-bromoisophthalate (5.0 g), allyl tributyl tin (6.7 g), tetrakis(triphenylphosphine)palladium (1.1 g), and toluene (100 mL) was heated under reflux for 20 hours. The reaction mixture was returned to room temperature, diluted with water, and extracted with ethyl acetate. The organic layer was concentrated under reduced pressure, and the resulting residue was purified under silica gel column chromatography (hexane/ethyl acetate) to obtain dimethyl 4-allyl isophthalic acid (3.1 g).

Preparation Example 35

A mixture of 4-{[(2,2-dimethyl-4,6-dioxo-1,3-dioxan-5-ylidene)methyl]amino}-3-methylbenzoic acid (10.1 g) and diphenyl ether (101 mL) was heated under stirring in an oil bath at 280° C. for 2 hours. The reaction mixture was returned to room temperature, diluted with petroleum ether and the precipitate was collected by filtration to obtain 4-hydroxy-8-methylquinoline-6-carboxylic acid (6.7 g).

Preparation Example 36

A mixture of 4-amino-3-methylbenzoic acid (7.3 g), Meldrum's acid (7.3 g), methyl orthoformate (5.6 g) and methanol (30 mL) was heated under stirring in an oil bath at 60° C. for 5 hours. The reaction mixture was returned to room temperature, diluted with ethyl acetate and the precipitate was collected by filtration to obtain 4-{[(2,2-dimethyl-4,6-dioxo-1,3-dioxan-5-ylidene)methyl]amino}-3-methylbenzoic acid (10.1 g).

Preparation Example 37

A mixture of phosphorus pentoxide (37 g) and phosphoric acid (46 g) was heated under stirring in an oil bath at 140° C., and methyl 4-amino-3-methylbenzoate (3.0 g) and ethyl acetoacetate (2.8 g) were added thereto, followed by heating under stirring for an additional 2 hours. The reaction mixture was cooled to 60° C., poured into water, and neutralized with a 29% aqueous ammonia solution, and the precipitate was collected by filtration to obtain methyl 2,8-dimethyl-4-oxo-1,4-dihydroquinoline-6-carboxylate (1.8 g).

Preparation Example 38

A mixed liquid of 7-bromo-4-fluoroisoquinolin-1-ol hydrochloride (3.0 g), palladium (II) acetate (484 mg), 1,1'-bis(diphenylphosphino)ferrocene (1.2 g), triethylamine (4.4 g), NMP (60 mL), and methanol (60 mL) was stirred at room temperature for 15 minutes while carbon monoxide gas was passed therethrough. The reaction was further heated under stirring in an oil bath at 80° C. for 16 hours under a carbon monoxide gas atmosphere at 1 atm. The reaction mixture was returned to room temperature, the insoluble materials were separated by filtration, and then the precipitate was concentrated under reduced pressure. The resulting residue was diluted with water, and then the precipitate was collected by filtration to obtain methyl 4-fluoro-1-hydroxyisoquinoline-7-carboxylate (2.3 g).

Preparation Example 39

A mixture of 2-bromo-1-chloro-3,5-difluorobenzene (800 mg), bis(pinacolato)diborone (1.1 g), bis(triphenylphosphine)palladium chloride (123 mg), triphenylphosphine (92 mg), potassium acetate (1.0 g), and 1,4-dioxane (24 mL) was heated under stirring in an oil bath at 100° C. for 18 hours. The reaction mixture was returned to room temperature, the insoluble materials were separated by filtration, and the filtrate was concentrated under reduced pressure. The resulting residue was purified under silica gel column chromatography (hexane/ethyl acetate) to obtain 2-(2-chloro-4,6-difluorophenyl)-4,4,5,5-tetramethyl-1,3,2-dioxaborolane (242 mg).

Preparation Example 521

Under argon gas atmosphere, a mixture of methyl 4-bromo-1-(2,4,6-trifluorophenyl)isoquinoline-7-carboxylate (150 mg), ethylboronic acid (84 mg), tetrakis(triphenylphosphine)palladium (44 mg), tripotassium phosphate (241 mg), toluene (5 mL), and water (0.3 mL) was heated under stirring in an oil bath at 100° C. for one day. The reaction mixture was returned to room temperature, and diluted with water and ethyl acetate, and then the insoluble matter was separated by filtration. The filtrate was extracted with ethyl acetate, and the organic layer was concentrated under reduced pressure. The resulting residue was purified under silica gel column chromatography (hexane/ethyl acetate) to obtain methyl 4-ethyl-1-(2,4,6-trifluorophenyl)isoquinoline-7-carboxylate (71 mg).

Preparation Example 522

A mixture of methyl 4-chloro-1-(3-chloro-2-hydroxyphenyl)isoquinoline-7-carboxylate (150 mg), potassium carbonate (119 mg), iodomethane (245 mg), and DMF (3 mL) was stirred at room temperature for one day. The reaction mixture was diluted with water, and extracted with ethyl acetate. The organic layer was washed with saturated brine, dried, and concentrated under reduced pressure. The resulting residue was purified under silica gel column chromatography (hexane/ethyl acetate) to obtain methyl 4-chloro-1-(3-chloro-2-methoxyphenyl)isoquinoline-7-carboxylate (130 mg).

Preparation Example 523

Tetrabutylammonium fluoride (1M THF solution, 0.35 mL) was added to a mixture of methyl 1-[3,5-difluoro-4-(trimethylsilyl)pyridin-2-yl]-4-fluoroisoquinoline-7-carboxylate and THF (1.8 mL), and stirred at room temperature overnight. The reaction mixture was diluted with water, and extracted with ethyl acetate. The organic layer was washed with saturated brine, dried, and concentrated under reduced pressure. The resulting residue was purified under silica gel column chromatography (hexane/ethyl acetate) to obtain methyl 1-(3,5-difluoropyridin-2-yl)-4-fluoroisoquinoline-7-carboxylate (55 mg).

The compounds of Preparation Examples shown in Tables below were prepared using the respective corresponding starting materials in the same manner as the methods of Preparation Examples above. In addition, the structural formulae, the physicochemical data, and the production methods for the compounds of Preparation Examples are shown in Tables below.

Example 1

A mixture of 1-(2,4,6-trifluorophenyl)isoquinoline-7-carboxylic acid hydrochloride (200 mg), CDI (143 mg) and DMF (6 mL) was heated under stirring in an oil bath at 60° C. for 30 minutes. Then, the reaction mixture was returned to room temperature, and guanidine carbonate (265 mg) was added thereto, followed by stirring at room temperature for additional 20 hours. The reaction mixture was diluted with saturated aqueous sodium bicarbonate, extracted with ethyl acetate, and the organic layer was washed with water, dried, and concentrated under reduced pressure. The resulting residue was purified under NH silica gel column chromatography (chloroform/methanol=100:0-20:1), and formed into its salt with 4M hydrogen chloride/ethyl acetate solution to obtain N-(diaminomethylene)-1-(2,4,6-trifluorophenyl)isoquinoline-7-carboxamide dihydrochloride (232 mg).

Example 2

A mixture of guanidine hydrochloride (374 mg), sodium methoxide (212 mg), and methanol (10 mL) was stirred at room temperature for one hour. The reaction mixture was concentrated under reduced pressure, and a mixture of methyl 4-(hydroxymethyl)-1-(2,4,6-trifluorophenyl)isoquinoline-7-carboxylate (136 mg) and NMP (10 mL) was added thereto, followed by heating and stirring in an oil bath at 120° C. for 5 hours. The reaction mixture was returned to room temperature, diluted with water, and extracted with ethyl acetate. The organic layer was concentrated under reduced pressure, and the resulting residue was purified under NH silica gel column chromatography (chloroform/methanol=100:0-90:10). Then, ethanol and fumaric acid were added thereto, and the precipitate was collected by filtration to obtain N-(diaminomethylene)-4-(hydroxymethyl)-1-(2,4,6-trifluorophenyl)isoquinoline-7-carboxamide fumarate (46 mg).

Example 3

A mixture of N-[1-amino(3,5-dimethyl-1H-pyrazol-1-yl)methylene]-4-(2,4,6-trifluorophenyl)quinoline-6-carboxamide (73 mg) and methylamine (40% methanol solution, 32 mg) was stirred at room temperature for 20 hours. The reaction mixture was diluted with saturated aqueous sodium bicarbonate, and extracted with ethyl acetate. The organic layer was concentrated under reduced pressure, and the resulting residue was purified under silica gel column chromatography (chloroform/methanol=20:1), and formed into its salt with 4M hydrogen chloride/1,4-dioxane solution to obtain N-[1-amino(methylamino)methylene]-4-(2,4,6-trifluorophenyl)quinoline-6-carboxamide dihydrochloride.

The compounds of Examples 4 to 223 and 225 to 251 were prepared using the corresponding starting materials in the same manner as Example 1, and the compound of Example 224 was prepared using the corresponding starting materials in the same manner as Example 2. The structural formulae and the physicochemical data of the compounds of Examples are shown in Tables below.

The following abbreviations are used in the tables below.

PEx: Preparation Example number, Ex: Example number, Str: structural formula, Dat: physicochemical data (ESI+: ESI-MS[M+H]$^+$ or ESI-MS[M]$^+$; FAB+: FAB-MS[M+H]$^+$ or FAB-MS[M]$^+$; EI+: EI[M]$^+$; A/E+: APCI/ESI-MS[M+H]$^+$ or APCI/ESI-MS[M]$^+$ (APCI/ESI means simultaneous measurement of APCI and ESI); A/E−: APCI/ESI-MS[M−H]$^-$ (APCI/ESI means simultaneous measurement of APCI and ESI); NMR: δ (ppm) of peaks by $^1$HNMR in CDCl$_3$ or DMSO-d$_6$); Sal: salt (Blank or no description represents the free form, and the numeral present before the acidic ingredient represents a molar ratio. For example, when 2HCl is described shows that the compound is dihydrochloride); Me: methyl, Et: ethyl, iPr: isopropyl, cPr: cyclopropyl, tBu: tert-butyl, Tf: trifluoromethanesulfonyl, Fum: fumaric acid, Syn: production process (the numeral shows that the compound was produced using the corresponding starting material in the same manner as in the compound having the number as its Preparation Example number), ND: Not Determined.

TABLE 1

| PEx | Str |
|---|---|
| 1 | 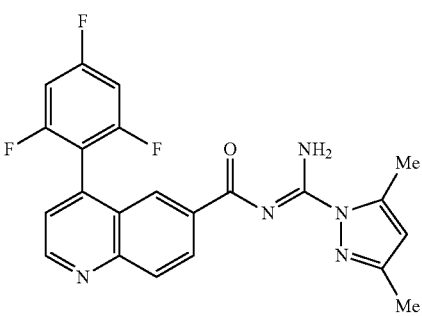 [SMILES: Cc1cc(C)n(/C(N)=N/C(=O)c2ccc3nccc(-c4c(F)cc(F)cc4F)c3c2)n1] |
| 2 | 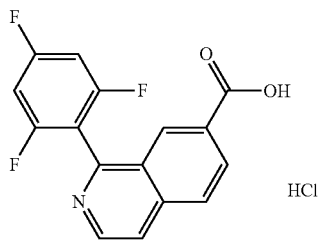 [SMILES: O=C(O)c1ccc2ccnc(-c3c(F)cc(F)cc3F)c2c1 ; Cl] |

TABLE 1-continued

| PEx | Str |
|---|---|
| 3 | 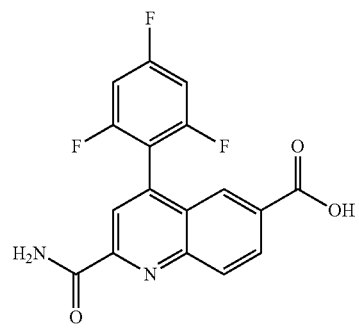 [SMILES: NC(=O)c1cc(-c2c(F)cc(F)cc2F)c2cc(C(=O)O)ccc2n1] |
| 4 | 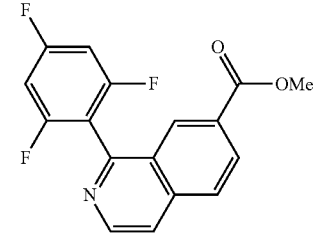 [SMILES: COC(=O)c1ccc2ccnc(-c3c(F)cc(F)cc3F)c2c1] |
| 5 | 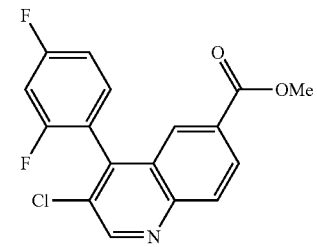 [SMILES: COC(=O)c1ccc2ncc(Cl)c(-c3ccc(F)cc3F)c2c1] |
| 6 | 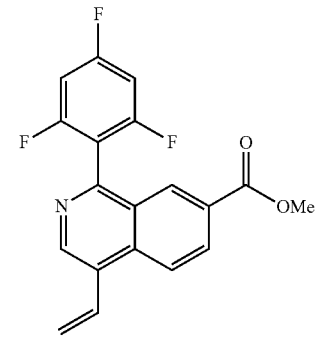 [SMILES: C=Cc1cnc(-c2c(F)cc(F)cc2F)c2cc(C(=O)OC)ccc12] |
| 7 | 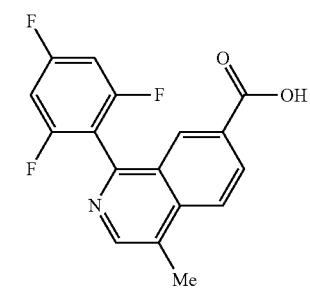 |

TABLE 1-continued

| PEx | Str |
|---|---|
| 8 | ethyl 5-(2,4,6-trifluorophenyl)quinoline-3-carboxylate |
| 9 | methyl 8-(3,5-difluoropyridin-4-yl)-5-chloro-1,6-naphthyridine-3-carboxylate |
| 10 | ethyl 4-(3,5-difluoropyridin-4-yl)-2,3-dimethylquinoline-6-carboxylate |
| 11 | methyl 1-(trifluoromethylsulfonyloxy)isoquinoline-7-carboxylate |
| 12 | 1-(2-fluoro-6-hydroxyphenyl)-4-fluoroisoquinoline-7-carboxylic acid |
| 13 | methyl 4-(2,4,6-trifluorophenyl)quinoline-7-carboxylate N-oxide |

TABLE 2

| PEx | Str |
|---|---|
| 14 | methyl 3-chloro-4-(pyrrolidin-1-yl)quinoline-6-carboxylate |
| 15 | methyl 1-(2,4,6-trifluorophenyl)-4-(hydroxymethyl)isoquinoline-7-carboxylate |
| 16 | methyl 1-(2,4,6-trifluorophenyl)-4-formylisoquinoline-7-carboxylate |
| 17 | methyl 1-(2,6-difluorophenyl)-4-isopropylisoquinoline-7-carboxylate |
| 18 | methyl 1-(2,4,6-trifluorophenyl)-4-cyanoisoquinoline-7-carboxylate |

TABLE 2-continued

| PEx | Str |
|---|---|
| 19 | 2-cyano-4-(2,4,6-trifluorophenyl)quinoline-6-carboxylic acid methyl ester |
| 20 | methyl 4-fluoro-1-hydroxy-3-methylisoquinoline-7-carboxylate |
| 21 | methyl 4-(difluoromethyl)-1-(2,6-difluorophenyl)isoquinoline-7-carboxylate |
| 22 | methyl 3-chloro-4-hydroxyquinoline-6-carboxylate |
| 23 | methyl 4-chloro-1-hydroxyisoquinoline-7-carboxylate |
| 24 | ethyl 3,4-dichloro-2-methylquinoline-6-carboxylate |
| 25 | methyl 2-chloro-4-(2,4,6-trifluorophenyl)quinoline-6-carboxylate |

TABLE 2-continued

| PEx | Str |
|---|---|
| 26 | methyl 4-bromo-1-hydroxyisoquinoline-7-carboxylate |
| 27 | methyl 4-bromo-3-chloroquinoline-6-carboxylate |

TABLE 3

| PEx | Str |
|---|---|
| 28 | methyl 1-hydroxy-4-iodoisoquinoline-7-carboxylate |
| 29 | methyl 3-iodo-4-oxo-1H-quinoline-6-carboxylate |
| 30 | methyl 4-oxo-3-(trifluoromethyl)-1H-quinoline-6-carboxylate |
| 31 | methyl 1-hydroxy-3-methylisoquinoline-7-carboxylate |
| 32 | methyl 3-methyl-1-oxo-1H-isochromene-7-carboxylate |
| 33 | 3-methyl-1-oxo-1H-isochromene-7-carboxylic acid |

TABLE 3-continued

| PEx | Str |
|---|---|
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) HCl |
| 44 | (structure) HCl |

TABLE 4

| PEx | Str |
|---|---|
| 45 | (structure) |
| 46 | (structure) |
| 47 | (structure) |

TABLE 4-continued

| PEx | Str |
|---|---|
| 48 | (structure) |
| 49 | (structure) |
| 50 | (structure) |
| 51 | (structure) |
| 52 | (structure) |
| 53 | (structure) |

TABLE 4-continued

| PEx | Str |
|---|---|
| 54 | (structure) |
| 55 | (structure) |
| 56 | (structure) |
| 57 | (structure) |
| 58 | (structure) |

TABLE 5

| PEx | Str |
|---|---|
| 59 | (structure) |

TABLE 5-continued

| PEx | Str |
|---|---|
| 60 | 2,4-dichlorophenyl-quinoline-7-carboxylic acid |
| 61 | 2,3-dichlorophenyl-quinoline-7-carboxylic acid |
| 62 | 2-chloro-6-fluorophenyl-quinoline-7-carboxylic acid |
| 63 | 2-cyanophenyl-quinoline-7-carboxylic acid |
| 64 | 4-chloro-2,6-difluorophenyl-quinoline-7-carboxylic acid methyl ester |
| 65 | 4-chloro-2,6-difluorophenyl-quinoline-7-carboxylic acid |
| 66 | 2-chloro-4,6-difluorophenyl-quinoline-7-carboxylic acid methyl ester |
| 67 | 4-chloro-2-fluorophenyl-quinoline-7-carboxylic acid methyl ester |
| 68 | 2-chloro-4-fluorophenyl-quinoline-7-carboxylic acid methyl ester |
| 69 | 2-chloro-4,6-difluorophenyl-quinoline-7-carboxylic acid |
| 70 | 4-chloro-2-fluorophenyl-quinoline-7-carboxylic acid |
| 71 | 2-chloro-4-fluorophenyl-quinoline-7-carboxylic acid |

TABLE 5-continued

| PEx | Str |
|---|---|
| 72 | 4-hydroxy-3-methylquinoline-6-carboxylic acid methyl ester |

TABLE 6

| PEx | Str |
|---|---|
| 73 | 4-(trifluoromethylsulfonyloxy)-3-methylquinoline-6-carboxylic acid methyl ester |
| 74 | 3-methyl-4-phenylquinoline-6-carboxylic acid methyl ester |
| 75 | 4-(2,4,6-trifluorophenyl)-3-methylquinoline-6-carboxylic acid methyl ester |
| 76 | 4-(2,5-dichlorophenyl)quinoline-6-carboxylic acid methyl ester |
| 77 | 4-(2,6-dichlorophenyl)quinoline-6-carboxylic acid methyl ester |
| 78 | 3-methyl-4-phenylquinoline-6-carboxylic acid |

TABLE 6-continued

| PEx | Str |
|---|---|
| 79 | 4-(2,4,6-trifluorophenyl)-3-methylquinoline-6-carboxylic acid |
| 80 | 4-(2,5-dichlorophenyl)quinoline-6-carboxylic acid |
| 81 | 4-(2,6-dichlorophenyl)quinoline-6-carboxylic acid |
| 82 | 1-(2-chloro-6-fluorophenyl)isoquinoline-7-carboxylic acid methyl ester |
| 83 | 1-(2,6-dichlorophenyl)isoquinoline-7-carboxylic acid methyl ester |
| 84 | 1-(4-chloro-2-fluorophenyl)isoquinoline-7-carboxylic acid methyl ester |

TABLE 6-continued

| PEx | Str |
|---|---|
| 85 | 4-(5-chloro-2,4-difluorophenyl)quinoline-7-carboxylic acid methyl ester |
| 86 | 4-(3-chloro-2-fluorophenyl)quinoline-7-carboxylic acid methyl ester |

TABLE 7

| PEx | Str |
|---|---|
| 87 | 4-(5-chloro-2-fluorophenyl)quinoline-6-carboxylic acid methyl ester |
| 88 | 4-(5-chloro-2,4-difluorophenyl)quinoline-6-carboxylic acid |
| 89 | 4-(3-chloro-2-fluorophenyl)quinoline-6-carboxylic acid |
| 90 | 4-(5-chloro-2-fluorophenyl)quinoline-6-carboxylic acid |

TABLE 7-continued

| PEx | Str |
|---|---|
| 91 | 1-(2-chloro-6-fluorophenyl)isoquinoline-7-carboxylic acid |
| 92 | 1-(2,6-dichlorophenyl)isoquinoline-7-carboxylic acid |
| 93 | 1-(4-chloro-2-fluorophenyl)isoquinoline-7-carboxylic acid |
| 94 | 1-(2,3-dichlorophenyl)isoquinoline-7-carboxylic acid methyl ester |
| 95 | 1-(2,4-dichlorophenyl)isoquinoline-7-carboxylic acid methyl ester |
| 96 | 1-(2-cyanophenyl)isoquinoline-7-carboxylic acid methyl ester |
| 97 | 4-(2-chloro-4,6-difluorophenyl)-3-methylquinoline-6-carboxylic acid methyl ester |

TABLE 7-continued
| PEx | Str |
|---|---|
| 98 | 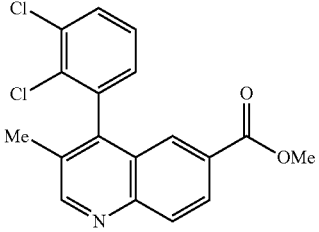 |
| 99 | 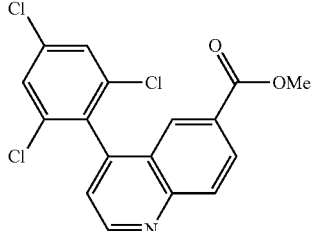 [SMILES: COC(=O)c1ccc2ccnc(-c3ccc(Cl)cc3F)c2c1] |
| 100 | 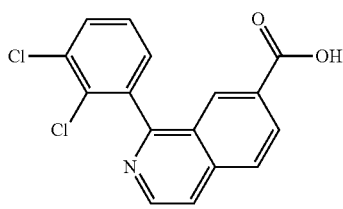 [SMILES: O=C(O)c1ccc2ccnc(-c3cccc(Cl)c3Cl)c2c1] |
TABLE 8
| PEx | Str |
|---|---|
| 101 | 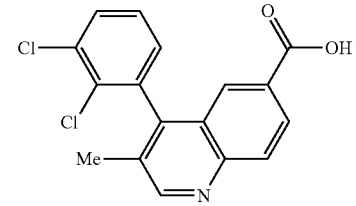 |
| 102 | 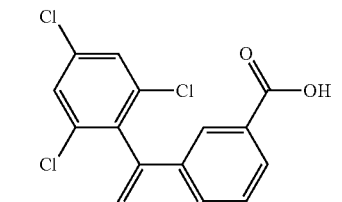 |
| 103 | 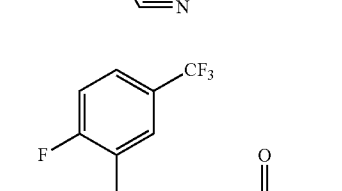 |
TABLE 8-continued
| PEx | Str |
|---|---|
| 104 | 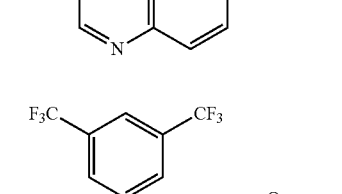 |
| 105 | 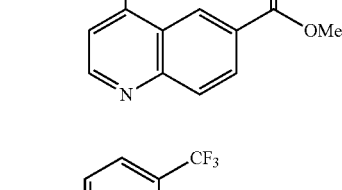 |
| 106 | 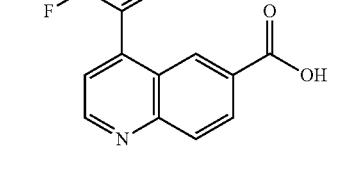 |
| 107 | 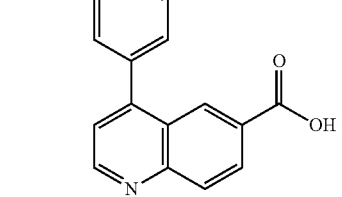 |
| 108 | 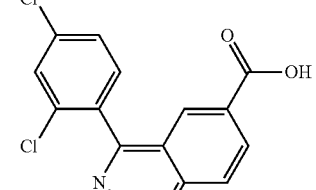 |
| 109 | 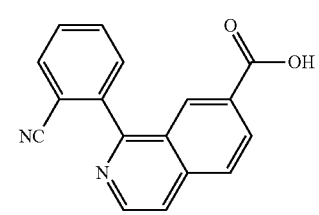 [SMILES: N#Cc1ccccc1-c1nccc2ccc(C(=O)O)cc12] |

TABLE 8-continued

| PEx | Str |
|---|---|
| 110 | 4-chloro-2-cyanophenyl isoquinoline methyl carboxylate |
| 111 | 2-fluoro-3-(trifluoromethyl)phenyl quinoline methyl carboxylate |
| 112 | 2-fluoro-3-(trifluoromethyl)phenyl quinoline carboxylic acid |
| 113 | 4-chloro-2-cyanophenyl isoquinoline carboxylic acid |
| 114 | 2,4-difluorophenyl 3-methylquinoline methyl carboxylate |

TABLE 9

| PEx | Str |
|---|---|
| 115 | 2,6-difluorophenyl 3-methylquinoline methyl carboxylate |
| 116 | 4-cyanophenyl quinoline methyl carboxylate |
| 117 | 2-fluoro-4-(trifluoromethyl)phenyl quinoline methyl carboxylate |
| 118 | 2,4-difluorophenyl 3-methylquinoline carboxylic acid |
| 119 | 2,6-difluorophenyl 3-methylquinoline carboxylic acid |
| 120 | 4-cyanophenyl quinoline carboxylic acid |
| 121 | 2-fluoro-4-(trifluoromethyl)phenyl quinoline carboxylic acid |

TABLE 9-continued

| PEx | Str |
|---|---|
| 122 | methyl 4-(2-methoxyphenyl)quinoline-6-carboxylate |
| 123 | methyl 4-(4-cyano-2-methoxyphenyl)quinoline-6-carboxylate |
| 124 | 4-(2-methoxyphenyl)quinoline-6-carboxylic acid |
| 125 | 4-(4-cyano-2-methoxyphenyl)quinoline-6-carboxylic acid |
| 126 | methyl 4-(4-fluoro-3-(trifluoromethyl)phenyl)quinoline-6-carboxylate |
| 127 | methyl 4-(3-fluoro-4-(trifluoromethyl)phenyl)quinoline-6-carboxylate |

TABLE 9-continued

| PEx | Str |
|---|---|
| 128 | 3-chloro-4-(((2,2-dimethyl-4,6-dioxo-1,3-dioxan-5-ylidene)methyl)amino)benzoic acid |

TABLE 10

| PEx | Str |
|---|---|
| 129 | 4-(4-fluoro-3-(trifluoromethyl)phenyl)quinoline-6-carboxylic acid |
| 130 | 4-(3-fluoro-4-(trifluoromethyl)phenyl)quinoline-6-carboxylic acid |
| 131 | methyl 4-hydroxy-8-methylquinoline-6-carboxylate |
| 132 | 8-chloro-4-hydroxyquinoline-6-carboxylic acid |
| 133 | methyl 8-chloro-4-hydroxyquinoline-6-carboxylate |

TABLE 10-continued
| PEx | Str |
|---|---|
| 134 | 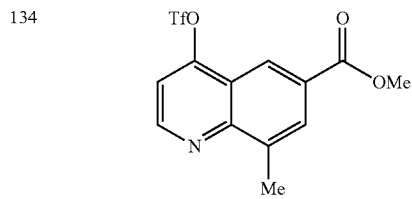 |
| 135 | 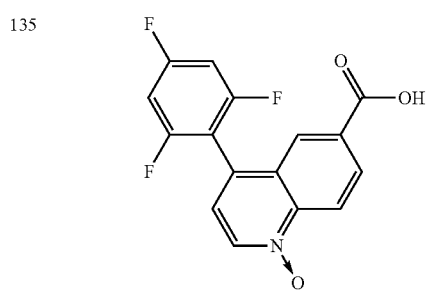 |
| 136 | 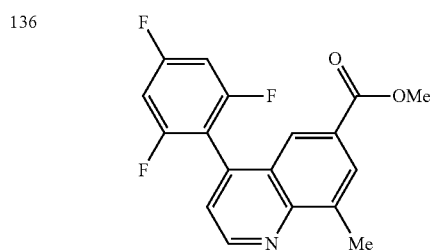 |
| 137 | 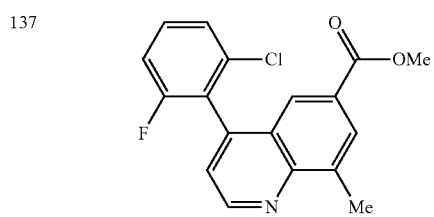 |
| 138 | 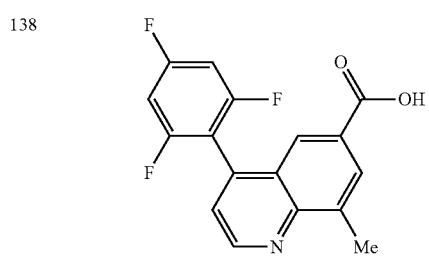 |
| 139 | 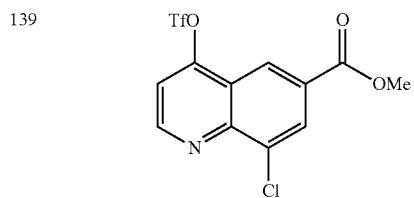 |
TABLE 10-continued
| PEx | Str |
|---|---|
| 140 | 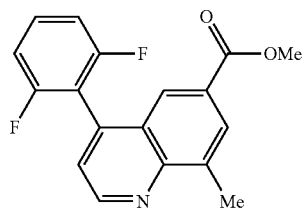 [SMILES: COC(=O)c1cc(C)c2nccc(-c3c(F)cccc3F)c2c1] |
| 141 | 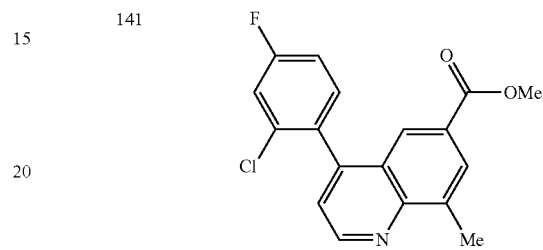 |
| 142 | 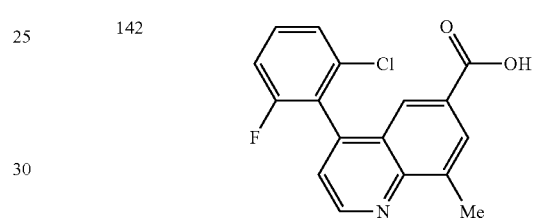 |
TABLE 11
| PEx | Str |
|---|---|
| 143 | 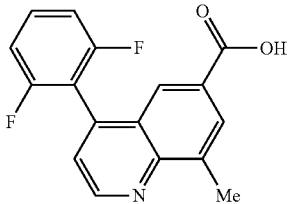 [SMILES: Cc1cc(C(=O)O)cc2c(-c3c(F)cccc3F)ccnc12] |
| 144 | 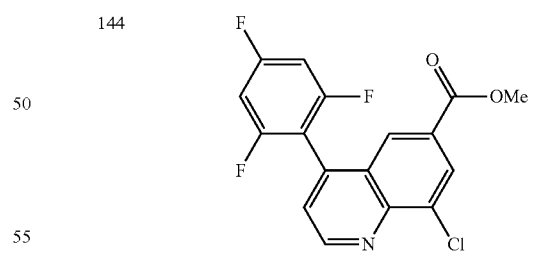 |
| 145 | 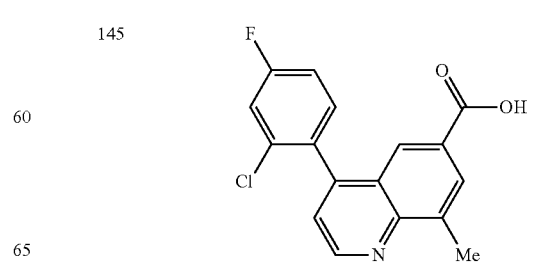 |

TABLE 11-continued
| PEx | Str |
|---|---|
| 146 | 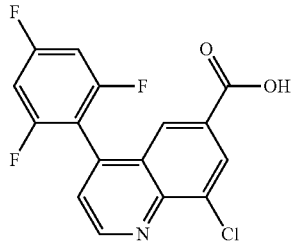 |
| 147 | 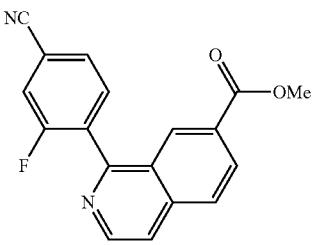 [SMILES: COC(=O)c1ccc2ccnc(-c3ccc(C#N)cc3F)c2c1] |
| 148 | 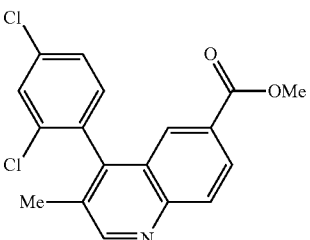 |
| 149 | 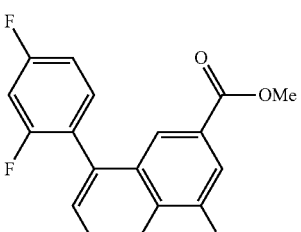 |
| 150 | 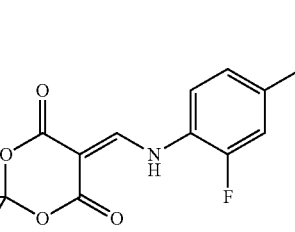 |
| 151 | 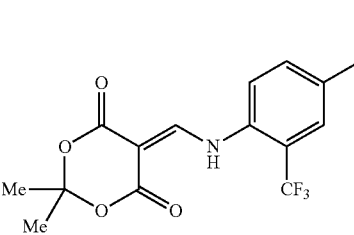 |
| 152 | 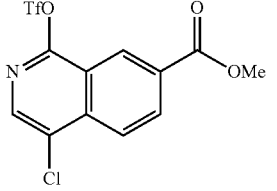 [SMILES: COC(=O)c1ccc2c(Cl)cnc(OS(=O)(=O)C(F)(F)F)c2c1] |
| 153 | 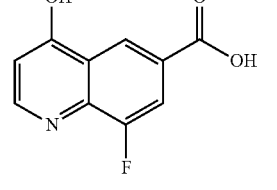 |
| 154 | 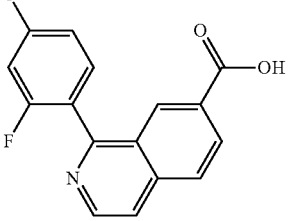 |
| 155 | 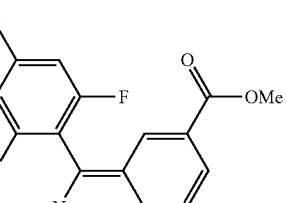 |
| 156 | 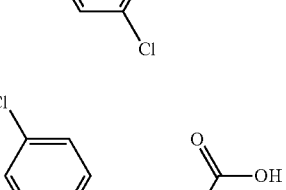 |
TABLE 12
| PEx | Str |
|---|---|
| 157 | 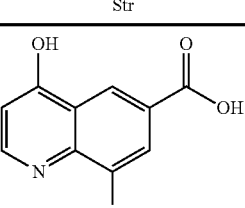 |

TABLE 12-continued
| PEx | Str |
|---|---|
| 158 | 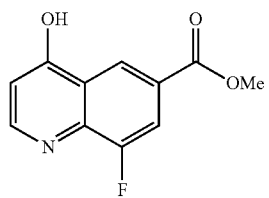 [SMILES: COC(=O)c1cc(F)c2nccc(O)c2c1] |
| 159 | 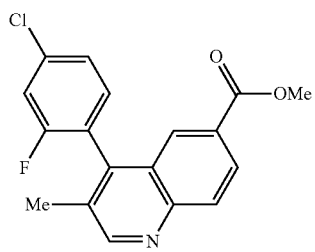 [SMILES: COC(=O)c1ccc2ncc(C)c(-c3ccc(Cl)cc3F)c2c1] |
| 160 | 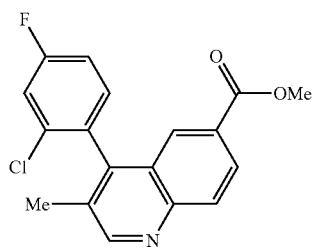 [SMILES: COC(=O)c1ccc2ncc(C)c(-c3ccc(F)cc3Cl)c2c1] |
| 161 | 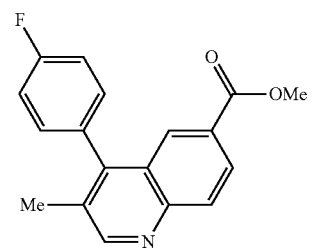 [SMILES: COC(=O)c1ccc2ncc(C)c(-c3ccc(F)cc3)c2c1] |
| 162 | 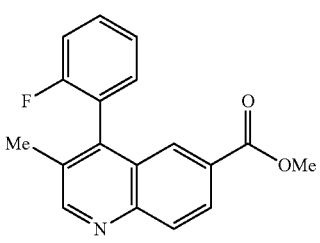 [SMILES: COC(=O)c1ccc2ncc(C)c(-c3ccccc3F)c2c1] |
| 163 | 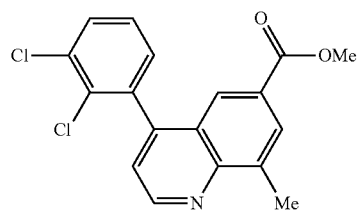 [SMILES: COC(=O)c1cc(C)c2nccc(-c3cccc(Cl)c3Cl)c2c1] |
TABLE 12-continued
| PEx | Str |
|---|---|
| 164 | 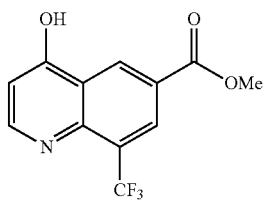 [SMILES: COC(=O)c1cc(C(F)(F)F)c2nccc(O)c2c1] |
| 165 | 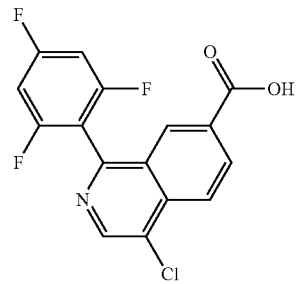 [SMILES: O=C(O)c1ccc2c(Cl)cnc(-c3c(F)cc(F)cc3F)c2c1] |
| 166 | 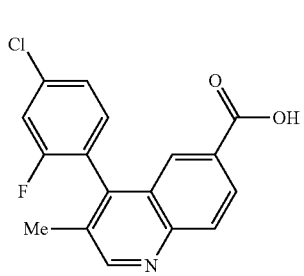 |
| 167 | 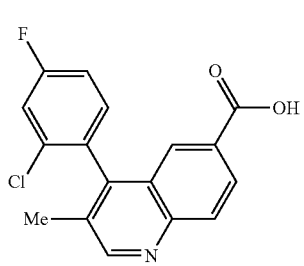 |
| 168 | 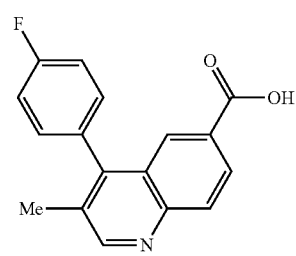 [SMILES: Cc1cnc2ccc(C(=O)O)cc2c1-c1ccc(F)cc1] |
| 169 | 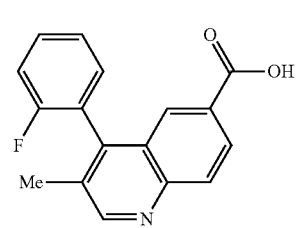 [SMILES: Cc1cnc2ccc(C(=O)O)cc2c1-c1ccccc1F] |

TABLE 12-continued
| PEx | Str |
|---|---|
| 170 | 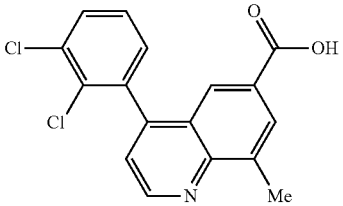 [SMILES: Cc1cc(C(=O)O)cc2c(-c3cccc(Cl)c3Cl)ccnc12] |
TABLE 13
| PEx | Str |
|---|---|
| 171 | 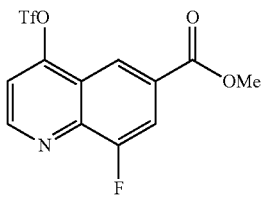 [SMILES: COC(=O)c1cc(F)c2nccc(OS(=O)(=O)C(F)(F)F)c2c1] |
| 172 | 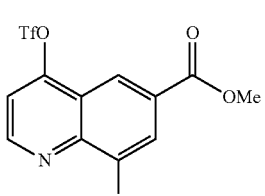 |
| 173 | |
| 174 | |
| 175 | |
TABLE 13-continued
| PEx | Str |
|---|---|
| 176 | 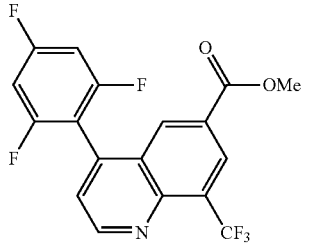 |
| 177 | 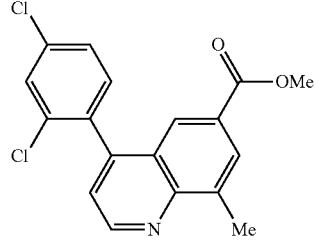 [SMILES: COC(=O)c1cc(C)c2nccc(-c3ccc(Cl)cc3Cl)c2c1] |
| 178 | 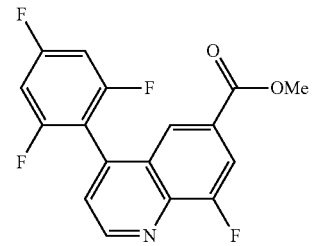 [SMILES: COC(=O)c1cc(F)c2nccc(-c3c(F)cc(F)cc3F)c2c1] |
| 179 | |
| 180 | |
| 181 | |

TABLE 13-continued

| PEx | Str |
|---|---|
| 182 | 4-(2,6-dichlorophenyl)-8-methylquinoline-6-carboxylic acid |
| 183 | methyl 4-(2-chloro-3-fluorophenyl)-8-methylquinoline-6-carboxylate |
| 184 | methyl 4-(2-chloro-3-fluorophenyl)quinoline-6-carboxylate |

TABLE 14

| PEx | Str |
|---|---|
| 185 | 4-(2-chloro-3-fluorophenyl)-8-methylquinoline-6-carboxylic acid |
| 186 | methyl 4-(2,6-difluoro-4-methoxyphenyl)-8-methylquinoline-6-carboxylate |
| 187 | methyl 4-(2,6-difluoro-4-methoxyphenyl)quinoline-6-carboxylate |

TABLE 14-continued

| PEx | Str |
|---|---|
| 188 | 4-(2-chloro-3-fluorophenyl)quinoline-6-carboxylic acid |
| 189 | 4-(2,6-difluoro-4-methoxyphenyl)-8-methylquinoline-7-carboxylic acid |
| 190 | 4-(2,6-difluoro-4-methoxyphenyl)quinoline-6-carboxylic acid |
| 191 | 5-(2,3,5-trifluorophenyl)quinoline-3-carboxylic acid |
| 192 | methyl 4-(2-chloro-5-fluorophenyl)-8-methylquinoline-6-carboxylate |
| 193 | methyl 4-(2-chloro-5-fluorophenyl)quinoline-6-carboxylate |

TABLE 14-continued

| PEx | Str |
|---|---|
| 194 | 4-(2-chloro-5-fluorophenyl)-8-methylquinoline-6-carboxylic acid |
| 195 | methyl 4-(cyclohex-1-en-1-yl)quinoline-6-carboxylate |
| 196 | 4-(2-chloro-5-fluorophenyl)quinoline-6-carboxylic acid |
| 197 | 4-(cyclohex-1-en-1-yl)quinoline-6-carboxylic acid |
| 198 | methyl 4-(2-chloro-3-fluorophenyl)-3-methylquinoline-6-carboxylate |

TABLE 15

| PEx | Str |
|---|---|
| 199 | 4-(2-chloro-3-fluorophenyl)-3-methylquinoline-6-carboxylic acid |

TABLE 15-continued

| PEx | Str |
|---|---|
| 200 | methyl 4-bromo-1-(trifluoromethylsulfonyloxy)isoquinoline-7-carboxylate |
| 201 | methyl 4-bromo-1-(2,4,6-trifluorophenyl)isoquinoline-7-carboxylate |
| 202 | methyl 4-(2-chloro-4,6-difluorophenyl)-8-methylquinoline-6-carboxylate |
| 203 | methyl 4-(cyclohex-1-en-1-yl)-3-methylquinoline-6-carboxylate |
| 204 | 4-cyano-1-(2,4,6-trifluorophenyl)isoquinoline-7-carboxylic acid |
| 205 | 4-(2-chloro-4,6-difluorophenyl)-8-methylquinoline-6-carboxylic acid |

TABLE 15-continued

| PEx | Str |
| --- | --- |
| 206 | 4-(cyclohex-1-en-1-yl)-3-methylquinoline-6-carboxylic acid |
| 207 | methyl 4-(4-chloro-2-fluorophenyl)-8-methylquinoline-6-carboxylate |
| 208 | methyl 4-(2-fluoro-4-methylphenyl)-8-methylquinoline-6-carboxylate |
| 209 | 4-(4-chloro-2-fluorophenyl)-8-methylquinoline-6-carboxylic acid |
| 210 | methyl 3-chloro-4-(2-fluorophenyl)quinoline-6-carboxylate |
| 211 | 4-(2-fluoro-4-methylphenyl)-8-methylquinoline-6-carboxylic acid |

TABLE 15-continued

| PEx | Str |
| --- | --- |
| 212 | methyl 4-(2-chloro-4-methoxyphenyl)-8-methylquinoline-6-carboxylate |

TABLE 16

| PEx | Str |
| --- | --- |
| 213 | 3-chloro-4-(2-fluorophenyl)quinoline-6-carboxylic acid |
| 214 | methyl 4-cyclopropyl-8-methylquinoline-6-carboxylate |
| 215 | 4-(2-chloro-4-methoxyphenyl)-8-methylquinoline-6-carboxylic acid |
| 216 | 4-cyclopropyl-8-methylquinoline-6-carboxylic acid |
| 217 | 3-chloro-4-(2,4-difluorophenyl)quinoline-6-carboxylic acid |

TABLE 16-continued

| PEx | Str |
|---|---|
| 218 | 4-(4-fluorophenyl)-3-chloroquinoline-6-carboxylic acid methyl ester |
| 219 | 4-phenyl-3-chloroquinoline-6-carboxylic acid methyl ester |
| 220 | 4-(4-fluorophenyl)-3-chloroquinoline-6-carboxylic acid |
| 221 | 4-phenyl-3-chloroquinoline-6-carboxylic acid |
| 222 | 1-(2,4,6-trifluorophenyl)-4-methylisoquinoline-7-carboxylic acid methyl ester |
| 223 | 1-(2,4-difluorophenyl)-4-fluoroisoquinoline-7-carboxylic acid methyl ester |
| 224 | 4-(cyclopentenyl)-8-methylquinoline-6-carboxylic acid methyl ester |
| 225 | 1-(2,4,6-trifluorophenyl)-4-fluoroisoquinoline-8-carboxylic acid |

TABLE 17

| PEx | Str |
|---|---|
| 226 | 1-(2,4-difluorophenyl)-4-fluoroisoquinoline-7-carboxylic acid |
| 227 | 3-chloro-4-cyclopropylquinoline-6-carboxylic acid methyl ester |
| 228 | 3-chloro-4-cyclopropylquinoline-6-carboxylic acid |
| 229 | 4-(4-chloro-2-methoxyphenyl)-8-methylquinoline-6-carboxylic acid methyl ester |

TABLE 17-continued
| PEx | Str |
|---|---|
| 230 | 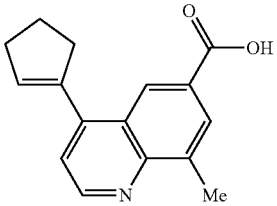 [SMILES: Cc1cc(C(=O)O)cc2c(C3=CCCC3)ccnc12] |
| 231 | 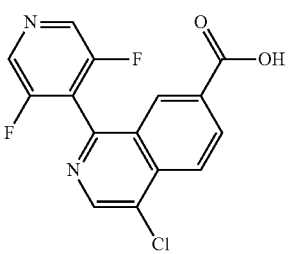 [SMILES: O=C(O)c1ccc2c(Cl)cnc(-c3c(F)cncc3F)c2c1] |
| 232 | 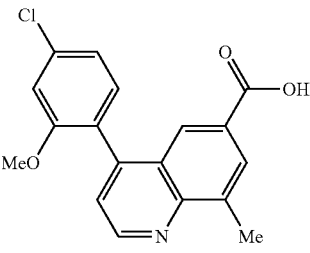 [SMILES: COc1cc(Cl)ccc1-c1ccnc2c(C)cc(C(=O)O)cc12] |
| 233 | 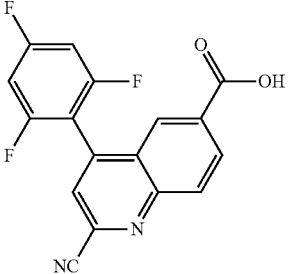 [SMILES: N#Cc1cc(-c2c(F)cc(F)cc2F)c2cc(C(=O)O)ccc2n1] |
| 234 | 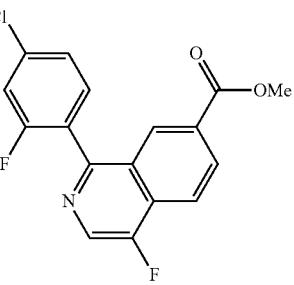 |
| 235 | 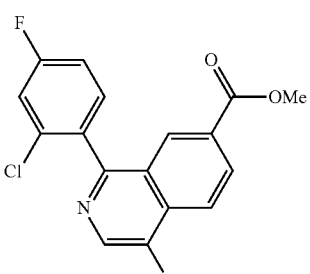 |
TABLE 17-continued
| PEx | Str |
|---|---|
| 236 | 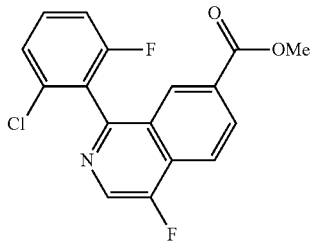 [SMILES: COC(=O)c1ccc2c(F)cnc(-c3c(F)cccc3Cl)c2c1] |
| 237 | 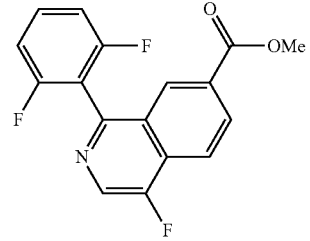 [SMILES: COC(=O)c1ccc2c(F)cnc(-c3c(F)cccc3F)c2c1] |
| 238 | 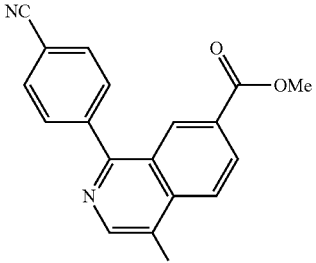 |
TABLE 18
| PEx | Str |
|---|---|
| 239 | 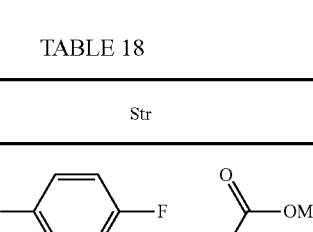 |
| 240 | 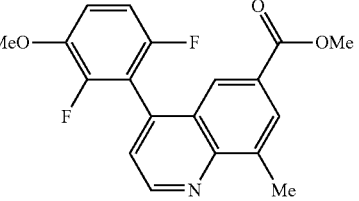 |

TABLE 18-continued

| PEx | Str |
|---|---|
| 241 | (4-chloro-2-fluorophenyl)-4-fluoroisoquinoline-7-carboxylic acid |
| 242 | 1-(2-chloro-6-fluorophenyl)-4-fluoroisoquinoline-7-carboxylic acid |
| 243 | 1-(2,6-difluorophenyl)-4-fluoroisoquinoline-7-carboxylic acid |
| 244 | 1-(4-cyanophenyl)-4-fluoroisoquinoline-7-carboxylic acid |
| 245 | ethyl 4-(2,4-difluorophenyl)-2-methylquinoline-6-carboxylate |
| 246 | ethyl 4-(2-fluorophenyl)-2-methylquinoline-6-carboxylate |
| 247 | 4-(2,6-difluorophenyl)-2-methylquinoline-6-carboxylic acid |
| 248 | 4-(2,6-difluoro-3-methoxyphenyl)-8-methylquinoline-6-carboxylic acid |
| 249 | methyl 2,8-dimethyl-4-(trifluoromethylsulfonyloxy)quinoline-6-carboxylate |
| 250 | 4-(2-fluorophenyl)-2-methylquinoline-6-carboxylic acid |
| 251 | 4-(2,4-difluorophenyl)-2-methylquinoline-6-carboxylic acid |

TABLE 19

| PEx | Str |
|---|---|
| 252 | 4-(2,4,6-trifluorophenyl)-2,8-dimethylquinoline-6-carboxylic acid methyl ester |
| 253 | 4-(2,6-difluorophenyl)-2,8-dimethylquinoline-6-carboxylic acid methyl ester |
| 254 | 4-(2,4-difluorophenyl)-2,8-dimethylquinoline-6-carboxylic acid methyl ester |
| 255 | 4-(2,4,6-trifluorophenyl)-2,8-dimethylquinoline-6-carboxylic acid |
| 256 | 4-(2,6-difluorophenyl)-2,8-dimethylquinoline-6-carboxylic acid |
| 257 | 4-bromo-3-trifluoromethylquinoline-6-carboxylic acid methyl ester |
| 258 | 4-(2,4-difluorophenyl)-2,8-dimethylquinoline-6-carboxylic acid |
| 259 | 3-chloro-4-hydroxy-2-methylquinoline-6-carboxylic acid ethyl ester |
| 260 | 4-(2,4-difluorophenyl)-3-trifluoromethylquinoline-7-carboxylic acid methyl ester |
| 261 | 2-ethyl-4-trifluoromethanesulfonyloxyquinoline-6-carboxylic acid ethyl ester |
| 262 | 4-(2,4-difluorophenyl)-3-trifluoromethylquinoline-6-carboxylic acid |
| 263 | 4-(2,4,6-trifluorophenyl)-2-ethylquinoline-6-carboxylic acid ethyl ester |

TABLE 19-continued
| PEx | Str |
|---|---|
| 264 | 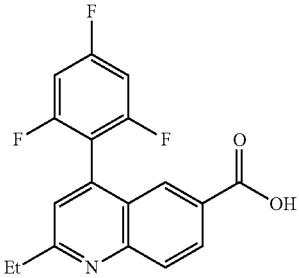 [SMILES: CCc1cc(-c2c(F)cc(F)cc2F)c2cc(C(=O)O)ccc2n1] |
TABLE 20
| PEx | Str |
|---|---|
| 265 | 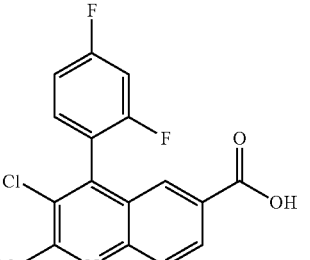 |
| 266 | 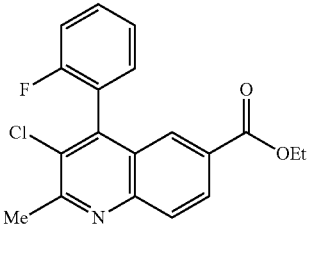 [SMILES: CCOC(=O)c1ccc2nc(C)c(Cl)c(-c3ccccc3F)c2c1] |
| 267 | 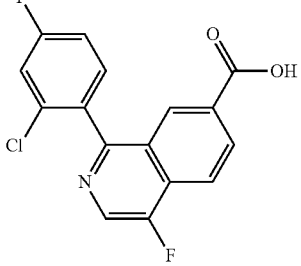 |
| 268 | 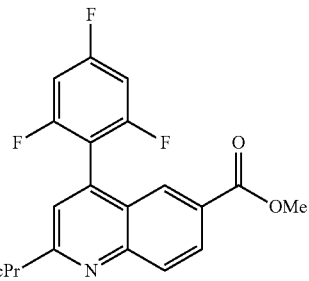 |
TABLE 20-continued
| PEx | Str |
|---|---|
| 269 | 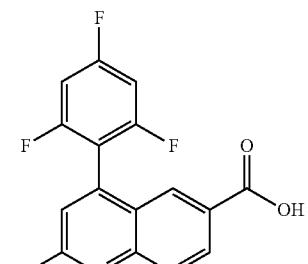 |
| 270 | 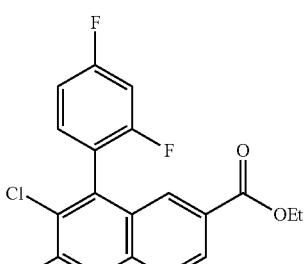 |
| 271 | 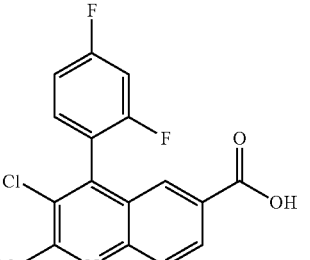 |
| 272 | 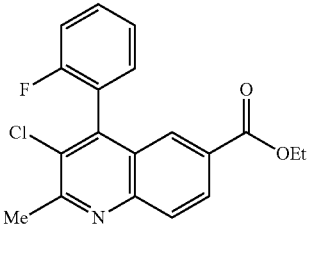 [SMILES: CCOC(=O)c1ccc2nc(C)c(Cl)c(-c3ccccc3F)c2c1] |
| 273 | 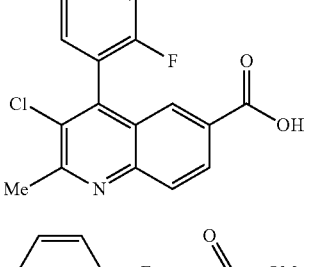 |
| 274 | 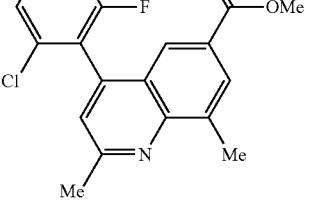 |
| 275 | 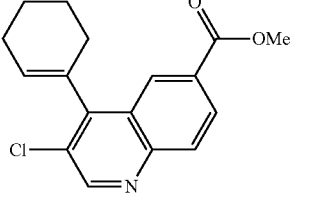 |

TABLE 20-continued
| PEx | Str |
|---|---|
| 276 | 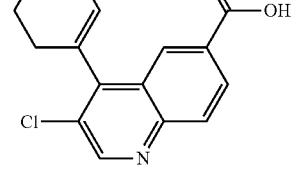 |
| 277 | 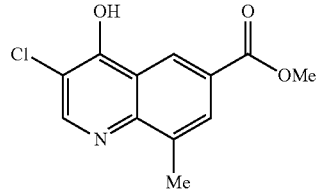 [SMILES: COC(=O)c1cc(C)c2ncc(Cl)c(O)c2c1] |
TABLE 21
| PEx | Str |
|---|---|
| 278 | 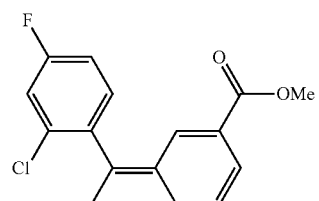 |
| 279 | 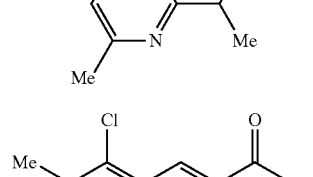 |
| 280 | 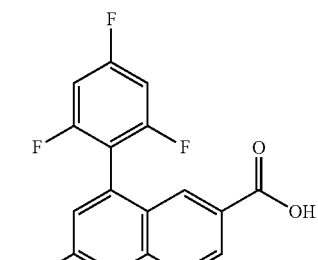 |
| 281 | 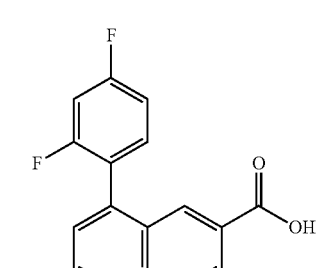 |
TABLE 21-continued
| PEx | Str |
|---|---|
| 282 | |
| 283 | |
| 284 | |
| 285 | |
| 286 | |

TABLE 21-continued

| PEx | Str |
|---|---|
| 287 | (2-chloro-6-fluorophenyl)-2,8-dimethylquinoline-6-carboxylic acid |
| 288 | methyl 3,4-dichloro-8-methylquinoline-6-carboxylate |
| 289 | methyl 3-chloro-4-(4-methoxyphenyl)quinoline-6-carboxylate |
| 290 | methyl 3-chloro-4-(2-chlorophenyl)quinoline-6-carboxylate |

TABLE 22

| PEx | Str |
|---|---|
| 291 | methyl 3-chloro-4-(4-cyanophenyl)quinoline-6-carboxylate |
| 292 | methyl 3-chloro-4-(4-cyano-2-methoxyphenyl)quinoline-6-carboxylate |
| 293 | 3-chloro-4-(4-methoxyphenyl)quinoline-7-carboxylic acid |
| 294 | 3-chloro-4-(2-chlorophenyl)quinoline-7-carboxylic acid |
| 295 | methyl 3-chloro-4-(2,4-difluorophenyl)-8-methylquinoline-6-carboxylate |
| 296 | methyl 3-chloro-4-(2-fluorophenyl)-8-methylquinoline-6-carboxylate |
| 297 | ethyl 4-(2-fluorophenyl)-2,3-dimethylquinoline-6-carboxylate |
| 298 | methyl 3-chloro-4-cyclopropyl-8-methylquinoline-6-carboxylate |

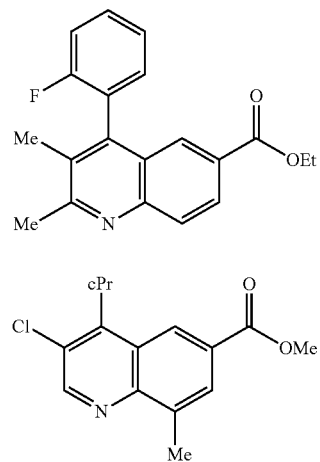

TABLE 22-continued

| PEx | Str |
|---|---|
| 299 | 3-chloro-4-(4-cyano-2-methoxyphenyl)quinoline-7-carboxylic acid |
| 300 | 3-chloro-4-(4-chloro-2-methoxyphenyl)quinoline-7-carboxylic acid |
| 301 | 3-chloro-4-(2,4-difluorophenyl)-8-methylquinoline-6-carboxylic acid |
| 302 | 3-chloro-4-(4-cyanophenyl)quinoline-6-carboxylic acid |
| 303 | 3-chloro-4-(2-fluorophenyl)-8-methylquinoline-6-carboxylic acid |
| 304 | 4-allylbenzene-1,3-dicarboxylic acid |

TABLE 23

| PEx | Str |
|---|---|
| 305 | 4-(2-fluorophenyl)-2,3-dimethylquinoline-6-carboxylic acid |
| 306 | methyl 3-chloro-4-(3-fluoropyridin-4-yl)quinoline-6-carboxylate |
| 307 | methyl 3-chloro-4-(2-methoxypyridin-3-yl)quinoline-6-carboxylate |
| 308 | 3-chloro-4-cyclopropyl-8-methylquinoline-6-carboxylic acid |
| 309 | 3-chloro-4-(3-fluoropyridin-4-yl)quinoline-7-carboxylic acid |
| 310 | 3-chloro-4-(2-methoxypyridin-3-yl)quinoline-7-carboxylic acid |
| 311 | methyl 3-chloro-4-(cyclopent-1-en-1-yl)quinoline-6-carboxylate |

TABLE 23-continued

| PEx | Str |
|---|---|
| 312 | 4-(cyclopenten-1-yl)-3-chloroquinoline-6-carboxylic acid |
| 313 | methyl 1-(trifluoromethylsulfonyloxy)-3-methylisoquinoline-7-carboxylate |
| 314 | methyl 1-(2,4,6-trifluorophenyl)-3-methylisoquinoline-7-carboxylate |
| 315 | methyl 1-(trifluoromethylsulfonyloxy)-3-methyl-4-fluoroisoquinoline-7-carboxylate |
| 316 | methyl 1-(2,4,6-trifluorophenyl)-3-methyl-4-fluoroisoquinoline-7-carboxylate |
| 317 | 1-(2,4,6-trifluorophenyl)-3-methylisoquinoline-7-carboxylic acid |
| 318 | 1-(2,4,6-trifluorophenyl)-3-methyl-4-fluoroisoquinoline-7-carboxylic acid |

TABLE 24

| PEx | Str |
|---|---|
| 319 | 4-(2,4-difluorophenyl)-2,3-dimethylquinoline-6-carboxylic acid |
| 320 | methyl 1-(2,6-difluorophenyl)-3-methylisoquinoline-7-carboxylate |
| 321 | methyl 4-(2-fluoro-4-methylphenyl)-3-chloroquinoline-6-carboxylate |
| 322 | methyl 4-(4-fluoro-2-methylphenyl)-3-chloroquinoline-6-carboxylate |

TABLE 24-continued
| PEx | Str |
|---|---|
| 323 | 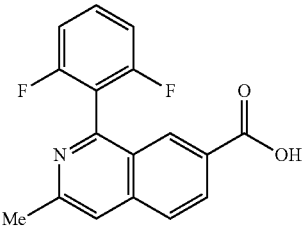 |
| 324 | 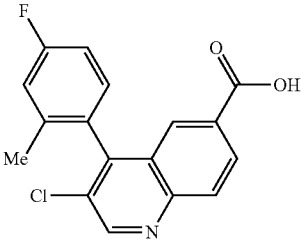 [SMILES: Cc1cc(F)ccc1-c1c(Cl)cnc2ccc(C(=O)O)cc12] |
| 325 | 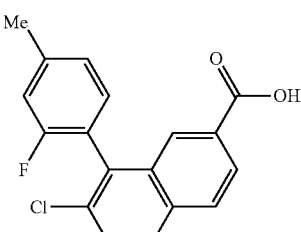 |
| 326 | 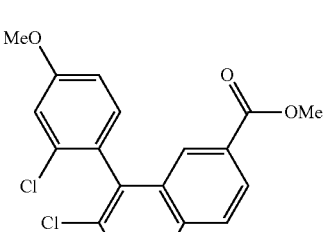 |
| 327 | 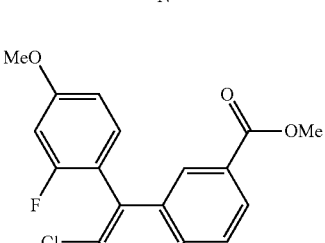 |
| 328 | 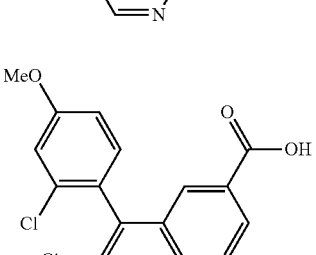 |
| 329 | 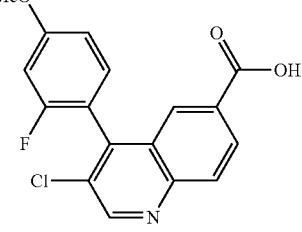 |
| 330 | 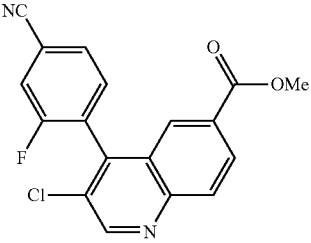 [SMILES: COC(=O)c1ccc2ncc(Cl)c(-c3ccc(C#N)cc3F)c2c1] |
TABLE 25
| PEx | Str |
|---|---|
| 331 | 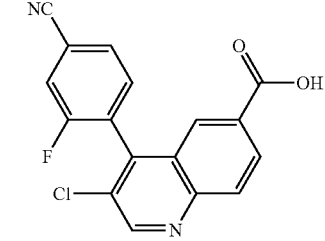 [SMILES: N#Cc1ccc(-c2c(Cl)cnc3ccc(C(=O)O)cc23)c(F)c1] |
| 332 | 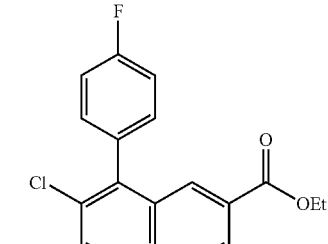 |
| 333 | 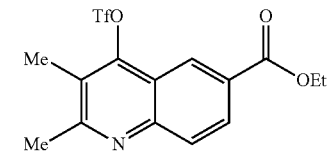 [SMILES: CCOC(=O)c1ccc2nc(C)c(C)c(OS(=O)(=O)C(F)(F)F)c2c1] |

TABLE 25-continued
| PEx | Str |
|---|---|
| 334 | 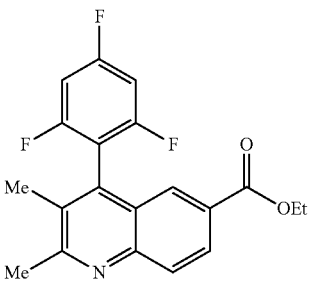 [SMILES: CCOC(=O)c1ccc2nc(C)c(C)c(-c3c(F)cc(F)cc3F)c2c1] |
| 335 | 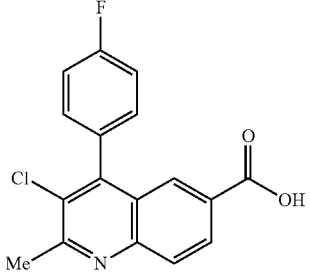 [SMILES: Cc1nc2ccc(C(=O)O)cc2c(-c2ccc(F)cc2)c1Cl] |
| 336 | 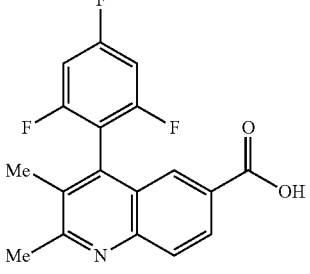 |
| 337 | 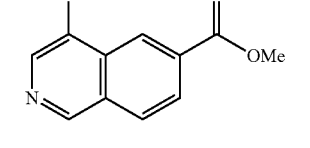 |
| 338 | 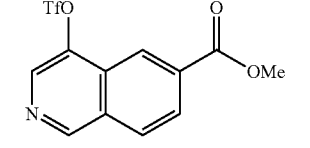 [SMILES: COC(=O)c1ccc2cncc(OS(=O)(=O)C(F)(F)F)c2c1] |
| 339 | 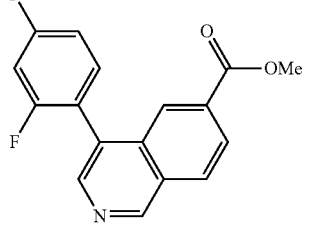 |
TABLE 25-continued
| PEx | Str |
|---|---|
| 340 | 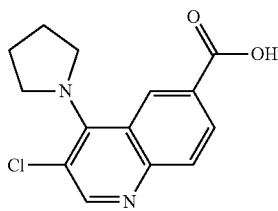 [SMILES: O=C(O)c1ccc2ncc(Cl)c(N3CCCC3)c2c1] |
| 341 | 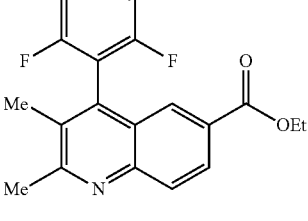 |
| 342 | 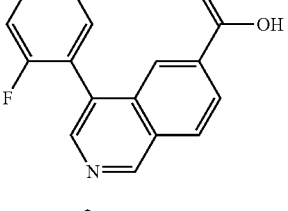 |
| 343 | 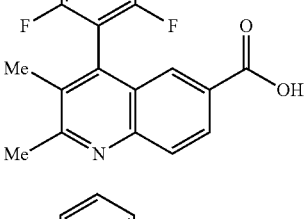 |
| 344 | 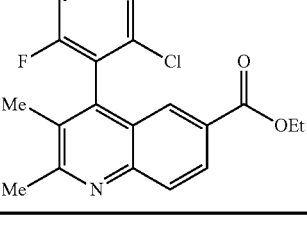 |
TABLE 26
| PEx | Str |
|---|---|
| 345 | 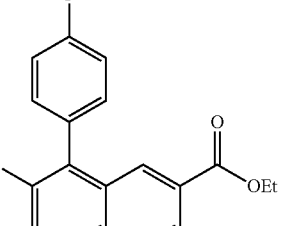 |

TABLE 26-continued

| PEx | Str |
|---|---|
| 346 | 4-(4-cyano-2-methoxyphenyl)-2,3-dimethylquinoline-6-carboxylic acid ethyl ester |
| 347 | 4-(4-methoxy-2,6-difluorophenyl)-2,3-dimethylquinoline-6-carboxylic acid ethyl ester |
| 348 | 4-(4-fluorophenyl)-2,3-dimethylquinoline-6-carboxylic acid |
| 349 | 3-fluoro-2-methyl-4-oxo-1,4-dihydroquinoline-6-carboxylic acid ethyl ester |
| 350 | 4-(4-cyano-2-methoxypyridin-3-yl)-2,3-dimethylquinoline-6-carboxylic acid |
| 351 | 4-(4-methoxy-2,6-difluorophenyl)-2,3-dimethylquinoline-6-carboxylic acid |
| 352 | 4-(2-chlorophenyl)-2,3-dimethylquinoline-6-carboxylic acid ethyl ester |
| 353 | 4-bromo-1-(2,6-difluorophenyl)isoquinoline-7-carboxylic acid methyl ester |
| 354 | 1-(3,5-difluoropyridin-4-yl)-4-fluoroisoquinoline-7-carboxylic acid methyl ester |
| 355 | 4-fluoro-1-(trifluoromethylsulfonyloxy)isoquinoline-7-carboxylic acid methyl ester |
| 356 | 4-cyclopropyl-1-(2,6-difluorophenyl)isoquinoline-6-carboxylic acid methyl ester |

TABLE 26-continued
| PEx | Str |
|---|---|
| 357 | 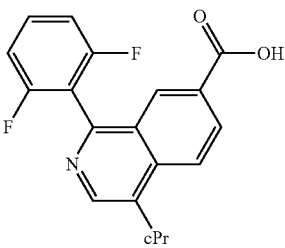 |
TABLE 27
| PEx | Str |
|---|---|
| 358 | |
| 359 | |
| 360 | |
| 361 | |
| 362 | |
| 363 | |
| 364 | |
| 365 | |
| 366 | |
| 367 | 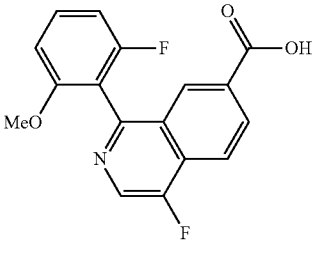 |

TABLE 27-continued

| PEx | Str |
|---|---|
| 368 | (structure: 1-(2-fluorophenyl)-4-fluoroisoquinoline-7-carboxylic acid) |
| 369 | (structure: 1-(2-chlorophenyl)-4-fluoroisoquinoline-7-carboxylic acid) |
| 370 | (structure: ethyl 4-(trifluoromethylsulfonyloxy)-3-fluoro-2-methylquinoline-6-carboxylate) |

TABLE 28

| PEx | Str |
|---|---|
| 371 | (structure: 1-(2,6-difluorophenyl)-4-isopropylisoquinoline-7-carboxylic acid) |
| 372 | (structure: ethyl 4-(2,6-difluorophenyl)-3-fluoro-2-methylquinoline-6-carboxylate) |
| 373 | (structure: 4-(2-chloro-4-fluorophenyl)-2,3-dimethylquinoline-6-carboxylic acid) |

TABLE 28-continued

| PEx | Str |
|---|---|
| 374 | (structure: 4-(2-chloro-4,6-difluorophenyl)-2-methylquinoline-6-carboxylic acid) |
| 375 | (structure: 4-(3-chloropyridin-4-yl)-2,3-dimethylquinoline-6-carboxylic acid) |
| 376 | (structure: 4-(2,6-difluorophenyl)-3-fluoro-2-methylquinoline-6-carboxylic acid) |
| 377 | (structure: methyl 1-(3-chloropyridin-4-yl)-4-fluoroisoquinoline-7-carboxylate) |
| 378 | (structure: ethyl 4-(2,6-difluoro-4-chlorophenyl)-2-methylquinoline-6-carboxylate) |
| 379 | (structure: 4-(3-chloro-5-fluoropyridin-4-yl)-2-methylquinoline-6-carboxylic acid) |

TABLE 28-continued
| PEx | Str |
|---|---|
| 380 | 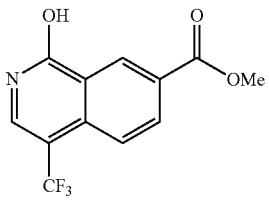 [SMILES: COC(=O)c1ccc2c(C(F)(F)F)cnc(O)c2c1] |
| 381 | 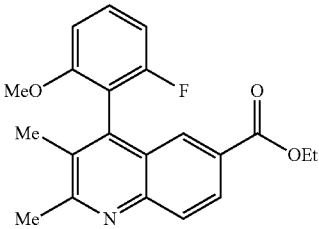 [SMILES: CCOC(=O)c1ccc2nc(C)c(C)c(-c3c(F)cccc3OC)c2c1] |
| 382 | 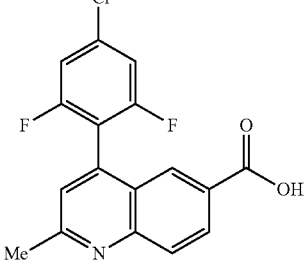 |
TABLE 29
| PEx | Str |
|---|---|
| 383 | 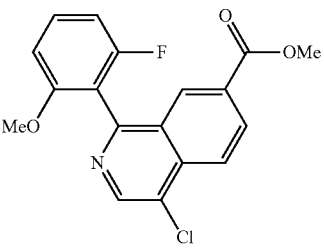 [SMILES: COC(=O)c1ccc2c(Cl)cnc(-c3c(F)cccc3OC)c2c1] |
| 384 | 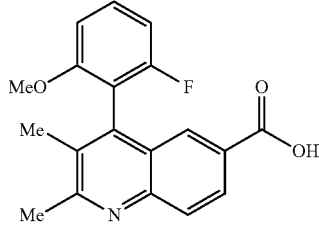 [SMILES: COc1cccc(F)c1-c1c(C)c(C)nc2ccc(C(=O)O)cc12] |
| 385 | 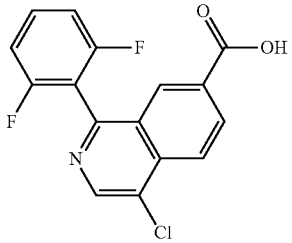 [SMILES: O=C(O)c1ccc2c(Cl)cnc(-c3c(F)cccc3F)c2c1] |
TABLE 29-continued
| PEx | Str |
|---|---|
| 386 | 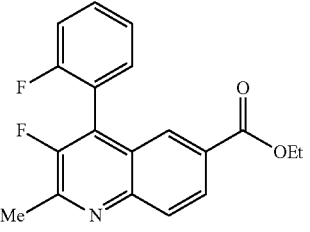 |
| 387 | 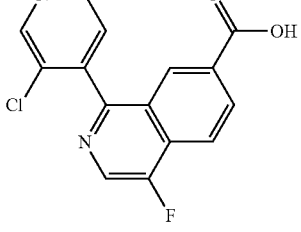 |
| 388 | 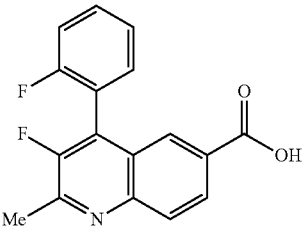 |
| 389 | 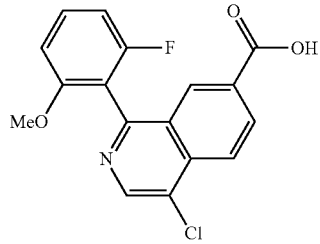 [SMILES: COc1cccc(F)c1-c1ncc(Cl)c2ccc(C(=O)O)cc12] |
| 390 | 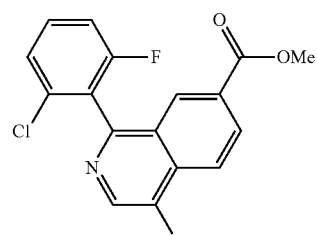 |
| 391 | 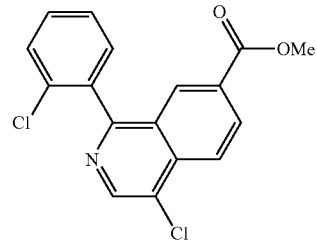 |

TABLE 29-continued
| PEx | Str |
|---|---|
| 392 | 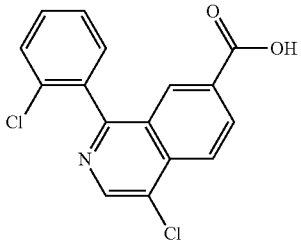 [SMILES: O=C(O)c1ccc2c(Cl)cnc(-c3ccccc3Cl)c2c1] |
| 393 | 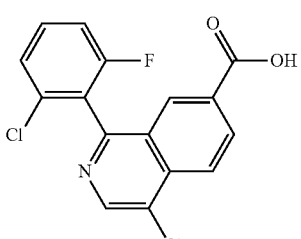 |
| 394 | 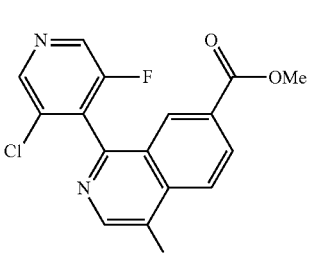 |
| 395 | 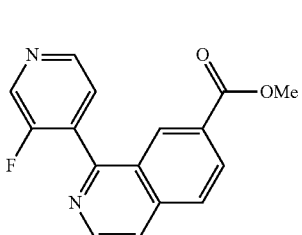 |
TABLE 30
| PEx | Str |
|---|---|
| 396 | 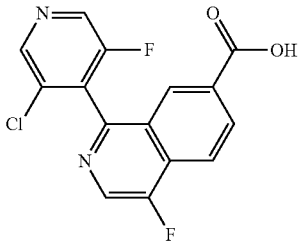 |
| 397 | 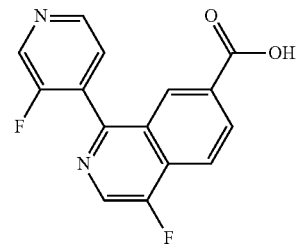 [SMILES: O=C(O)c1ccc2c(F)cnc(-c3ccncc3F)c2c1] |
| 398 | 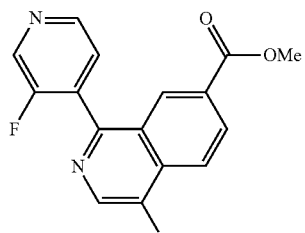 |
| 399 | 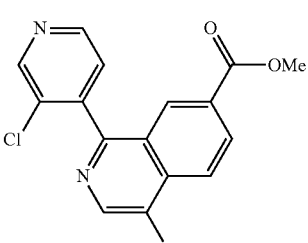 |
| 400 | 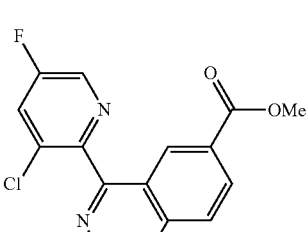 |
| 401 | 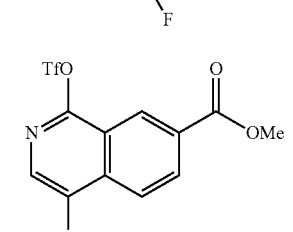 |
| 402 | 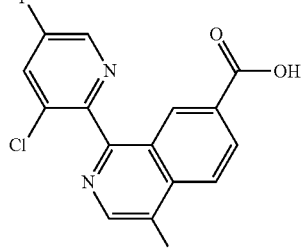 |

TABLE 30-continued

| PEx | Str |
|---|---|
| 403 | 3,4-dichloro-pyridin-3-yl substituted isoquinoline-7-carboxylic acid |
| 404 | 1-(2-fluorophenyl)-4-chloroisoquinoline-7-carboxylic acid methyl ester |
| 405 | 1-(4-fluoro-2-methoxyphenyl)-4-chloroisoquinoline-7-carboxylic acid methyl ester |
| 406 | 1-(4-cyano-2-methoxyphenyl)-4-chloroisoquinoline-7-carboxylic acid methyl ester |
| 407 | 1-(3-fluoropyridin-4-yl)-4-chloroisoquinoline-7-carboxylic acid |

TABLE 31

| PEx | Str |
|---|---|
| 408 | 1-(4-fluoro-2-methoxyphenyl)-4-chloroisoquinoline-7-carboxylic acid |
| 409 | 1-(2-chloro-4-methoxyphenyl)-4-chloroisoquinoline-7-carboxylic acid methyl ester |
| 410 | 1-(2,6-difluorophenyl)-4-ethylisoquinoline-7-carboxylic acid methyl ester |
| 411 | 1-(2,6-difluorophenyl)-4-methylisoquinoline-7-carboxylic acid methyl ester |
| 412 | 1-(2-fluorophenyl)-4-chloroisoquinoline-7-carboxylic acid |
| 413 | 1-(2,6-difluorophenyl)-4-methylisoquinoline-7-carboxylic acid |

TABLE 31-continued
| PEx | Str |
|---|---|
| 414 | 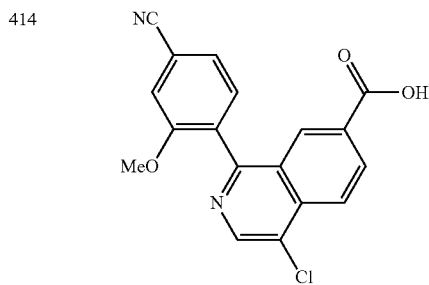 |
| 415 | 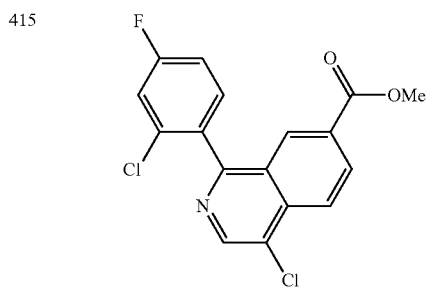 |
| 416 | 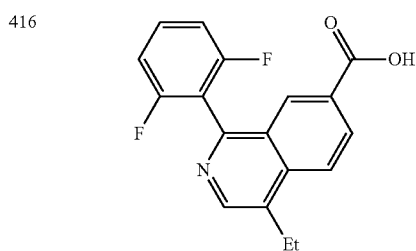 |
| 417 | 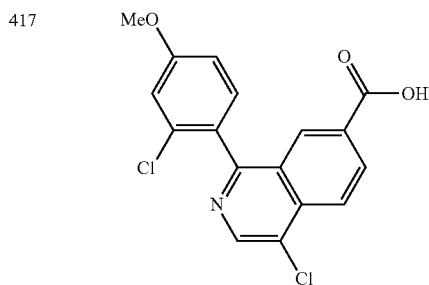 |
| 418 | 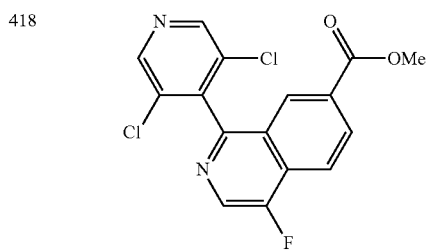 |
TABLE 31-continued
| PEx | Str |
|---|---|
| 419 | 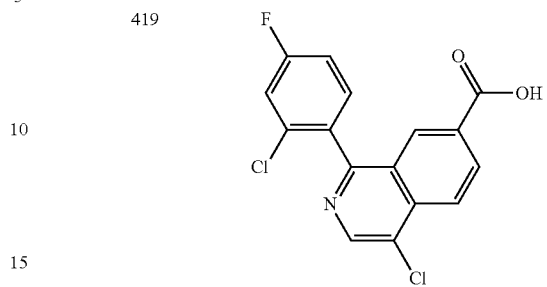 |
TABLE 32
| PEx | Str |
|---|---|
| 420 | 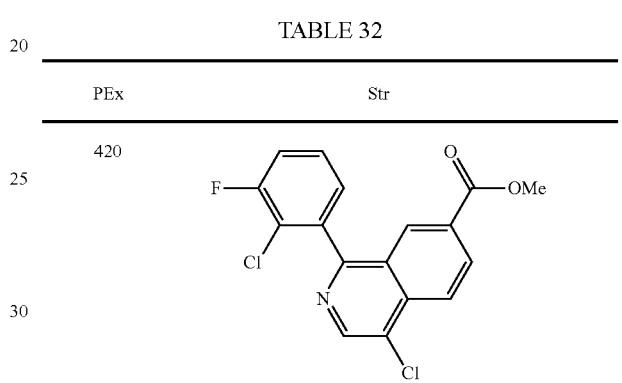 |
| 421 | 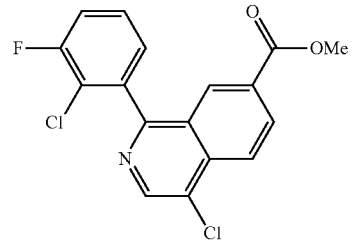 [SMILES: COC(=O)c1ccc2c(Cl)cnc(-c3cccc(F)c3Cl)c2c1] |
| 422 | 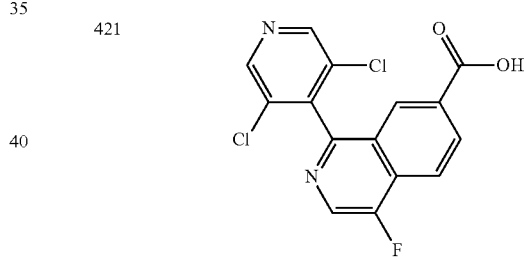 |
| 423 | 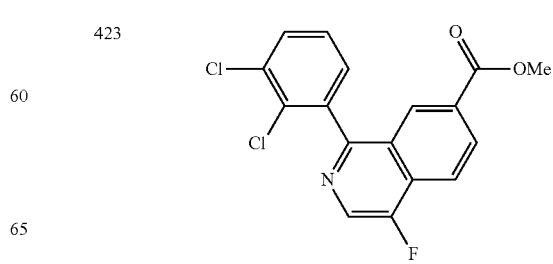 |

TABLE 32-continued

| PEx | Str |
|---|---|
| 424 | methyl 1-(2,6-dichlorophenyl)-4-fluoroisoquinoline-7-carboxylate |
| 425 | methyl 1-(2,4-dichlorophenyl)-4-fluoroisoquinoline-7-carboxylate |
| 426 | 1-(2,6-difluorophenyl)isoquinoline-7-carboxylic acid |
| 427 | 1-(2,3-dichlorophenyl)-4-fluoroisoquinoline-7-carboxylic acid |
| 428 | 1-(2,6-dichlorophenyl)-4-fluoroisoquinoline-7-carboxylic acid |
| 429 | 1-(2,4-dichlorophenyl)-4-fluoroisoquinoline-7-carboxylic acid |
| 430 | methyl 1-(4-chloro-2-methoxyphenyl)-4-chloroisoquinoline-7-carboxylate |
| 431 | methyl 1-(2,3-dichlorophenyl)-4-chloroisoquinoline-7-carboxylate |
| 432 | methyl 1-(2,3-difluorophenyl)-4-chloroisoquinoline-7-carboxylate |

TABLE 33

| PEx | Str |
|---|---|
| 433 | methyl 1-(4-fluoro-2-methylphenyl)-4-chloroisoquinoline-7-carboxylate |
| 434 | ethyl 4-(2-chlorophenyl)-3-chloro-2-methylquinoline-6-carboxylate |

TABLE 33-continued
| PEx | Str |
|---|---|
| 435 | 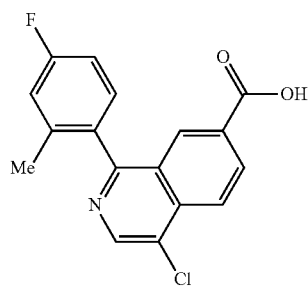 [SMILES: Cc1cc(F)ccc1-c1ncc(Cl)c2ccc(C(=O)O)cc12] |
| 436 | 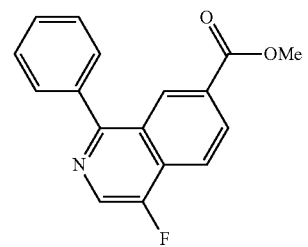 [SMILES: COC(=O)c1ccc2c(F)cnc(-c3ccccc3)c2c1] |
| 437 | 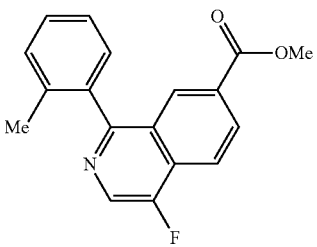 [SMILES: COC(=O)c1ccc2c(F)cnc(-c3ccccc3C)c2c1] |
| 438 | 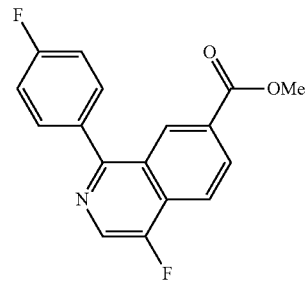 [SMILES: COC(=O)c1ccc2c(F)cnc(-c3ccc(F)cc3)c2c1] |
| 439 | 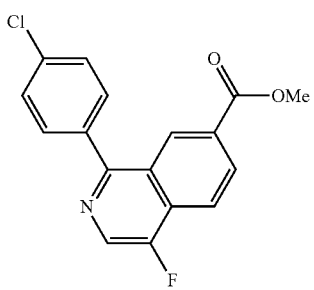 [SMILES: COC(=O)c1ccc2c(F)cnc(-c3ccc(Cl)cc3)c2c1] |
| 440 | 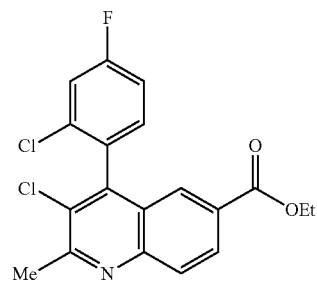 |
| 441 | 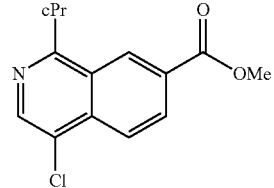 |
| 442 | 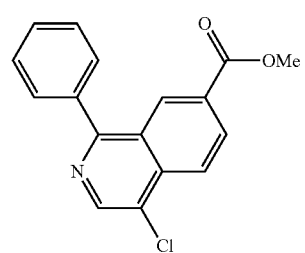 [SMILES: COC(=O)c1ccc2c(Cl)cnc(-c3ccccc3)c2c1] |
| 443 | 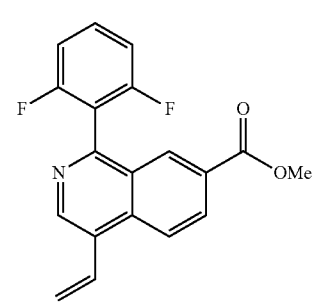 [SMILES: C=Cc1cnc(-c2c(F)cccc2F)c2cc(C(=O)OC)ccc12] |
| 444 | 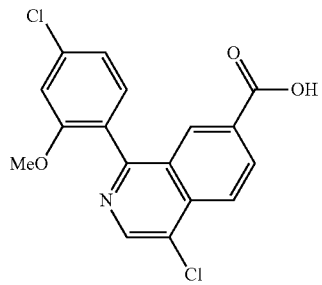 [SMILES: COc1cc(Cl)ccc1-c1ncc(Cl)c2ccc(C(=O)O)cc12] |

TABLE 34
| PEx | Str |
|---|---|
| 445 | 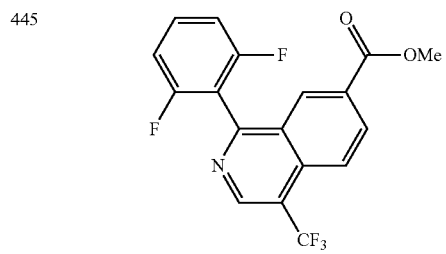 |
| 446 | 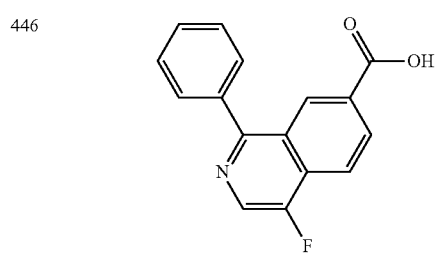 |
| 447 | 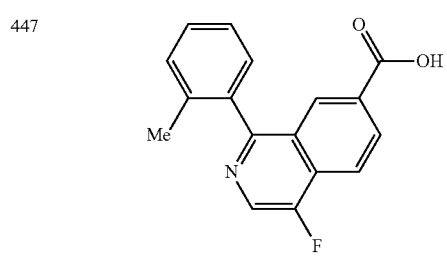 |
| 448 | 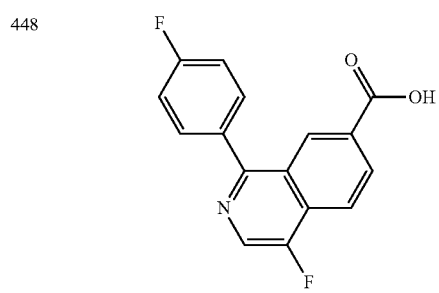 |
| 449 | 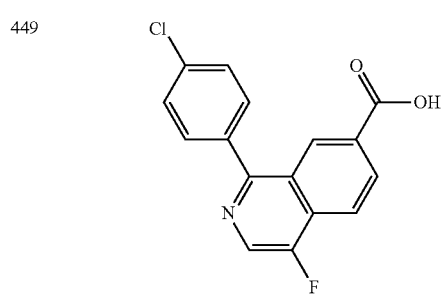 |
TABLE 34-continued
| PEx | Str |
|---|---|
| 450 | 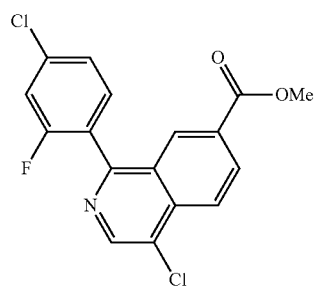 [SMILES: COC(=O)c1ccc2c(Cl)cnc(-c3ccc(Cl)cc3F)c2c1] |
| 451 | 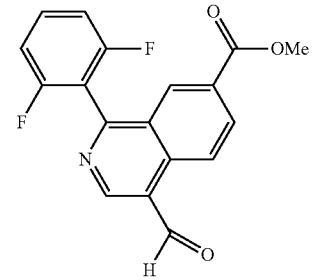 |
| 452 | 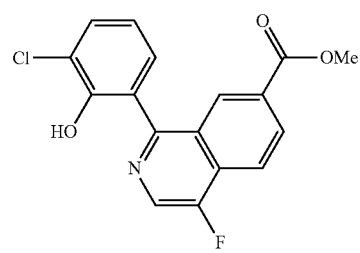 |
| 453 | 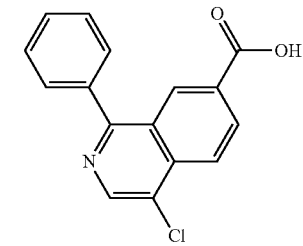 [SMILES: O=C(O)c1ccc2c(Cl)cnc(-c3ccccc3)c2c1] |
| 454 | 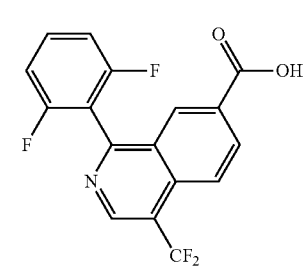 |

TABLE 34-continued

| PEx | Str |
|---|---|
| 455 | 4-chloro-1-(4-chloro-2-fluorophenyl)isoquinoline-7-carboxylic acid |
| 456 | 1-(4-chloro-2-hydroxyphenyl)-4-fluoroisoquinoline-7-carboxylic acid |

TABLE 35

| PEx | Str |
|---|---|
| 457 | 1-(2,6-difluorophenyl)-4-(trifluoromethyl)isoquinoline-7-carboxylic acid |
| 458 | 4-(2-chlorophenyl)-3-chloro-2-methylquinoline-6-carboxylic acid |
| 459 | methyl 4-bromo-1-(2-fluorophenyl)isoquinoline-7-carboxylate |

TABLE 35-continued

| PEx | Str |
|---|---|
| 460 | methyl 4-bromo-1-(2-chlorophenyl)isoquinoline-7-carboxylate |
| 461 | methyl 1-(2-chloro-3-fluorophenyl)-4-fluoroisoquinoline-7-carboxylate |
| 462 | 4-chloro-1-cyclopropylisoquinoline-7-carboxylic acid |
| 463 | methyl 1-(3-chloro-2-fluorophenyl)-4-fluoroisoquinoline-7-carboxylate |
| 464 | methyl 1-(2-chlorophenyl)-4-methylisoquinoline-7-carboxylate |
| 465 | 4-chloro-1-(2,3-dichlorophenyl)isoquinoline-7-carboxylic acid |

TABLE 35-continued
| PEx | Str |
|---|---|
| 466 | 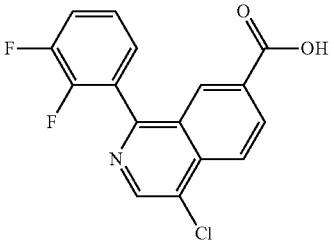 [SMILES: O=C(O)c1ccc2c(Cl)cnc(-c3cccc(F)c3F)c2c1] |
| 467 | 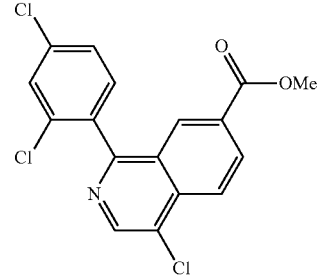 [SMILES: COC(=O)c1ccc2c(Cl)cnc(-c3ccc(Cl)cc3Cl)c2c1] |
| 468 | 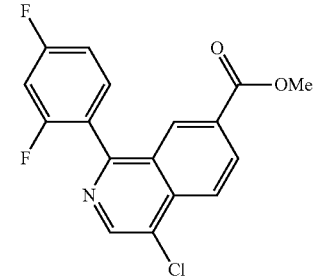 [SMILES: COC(=O)c1ccc2c(Cl)cnc(-c3ccc(F)cc3F)c2c1] |
| 469 | 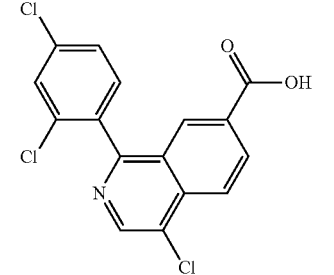 [SMILES: O=C(O)c1ccc2c(Cl)cnc(-c3ccc(Cl)cc3Cl)c2c1] |
TABLE 36
| PEx | Str |
|---|---|
| 470 | 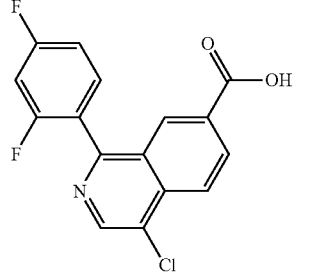 [SMILES: O=C(O)c1ccc2c(Cl)cnc(-c3ccc(F)cc3F)c2c1] |
| 471 | 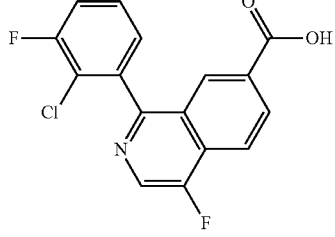 |
| 472 | 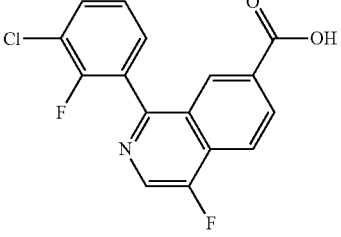 |
| 473 | 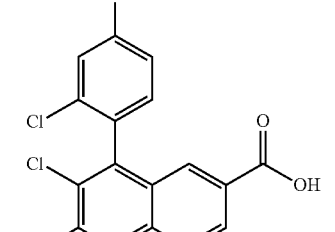 |
| 474 | 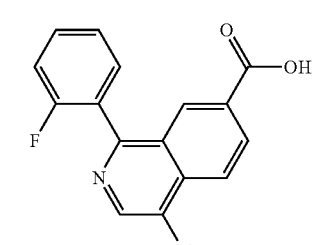 |
| 475 | 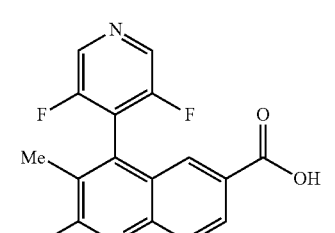 |
| 476 | 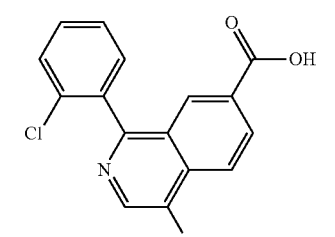 |

TABLE 36-continued

| PEx | Str |
|---|---|
| 477 | (structure) |
| 478 | (structure) |
| 479 | (structure) |
| 480 | (structure) |
| 481 | (structure) |

TABLE 37

| PEx | Str |
|---|---|
| 482 | (structure) |
| 483 | (structure) |
| 484 | (structure) |
| 485 | (structure) |
| 486 | (structure) |

TABLE 37-continued

| PEx | Str |
|---|---|
| 487 | (structure) |
| 488 | (structure) |
| 489 | (structure) |
| 490 | (structure) |
| 491 | (structure) |
| 492 | (structure) |
| 493 | (structure) |

TABLE 38

| PEx | Str |
|---|---|
| 494 | (structure) |
| 495 | (structure) |
| 496 | (structure) |
| 497 | (structure) |

TABLE 38-continued
| PEx | Str |
|---|---|
| 498 | 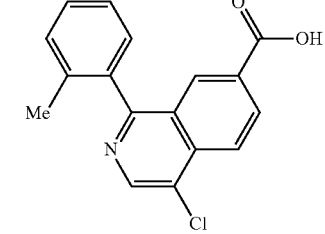 |
| 499 | |
| 500 | |
| 501 | |
| 502 | |
| 503 | |
TABLE 38-continued
| PEx | Str |
|---|---|
| 504 | 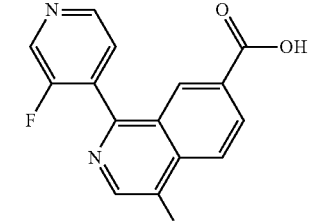 |
| 505 | |
TABLE 39
| PEx | Str |
|---|---|
| 506 | 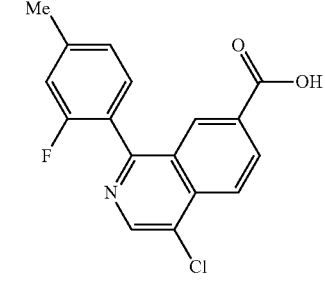 [SMILES: Cc1ccc(-c2ncc(Cl)c3ccc(C(=O)O)cc23)c(F)c1] |
| 507 | |
| 508 | |

TABLE 39-continued

| PEx | Str |
|---|---|
| 509 | (chemical structure) |
| 510 | (chemical structure) |
| 511 | (chemical structure) |
| 512 | (chemical structure) |
| 513 | (chemical structure) |
| 514 | (chemical structure) |
| 515 | (chemical structure) |
| 516 | (chemical structure) |
| 517 | (chemical structure) |

TABLE 40

| PEx | Str |
|---|---|
| 518 | (chemical structure) |
| 519 | (chemical structure) |

TABLE 40-continued

| PEx | Str |
|---|---|
| 520 | 1-(2-fluorophenyl)-4-ethylisoquinoline-7-carboxylic acid |

TABLE 41

| PEx | Syn | Dat |
|---|---|---|
| 1 | 1 | A/E+: 424 |
| 2 | 2 | ESI+: 304 |
| 3 | 3 | ESI+: 361 |
| 4 | 4 | ESI+: 318 |
| 5 | 5 | ESI+: 334 |
| 6 | 6 | A/E+: 344 |
| 7 | 7 | ESI+: 318 |
| 8 | 8 | A/E+: 332 |
| 9 | 9 | A/E+: 335 |
| 10 | 10 | A/E+: 343 |
| 11 | 11 | A/E+: 336 |
| 12 | 12 | ESI+: 302 |
| 13 | 13 | ESI+: 334 |
| 14 | 14 | A/E+: 291, 293 |
| 15 | 15 | ESI+: 348 |
| 16 | 16 | ESI+: 346 |
| 17 | 17 | ESI+: 342 |
| 18 | 18 | A/E+: 342 |
| 19 | 19 | ESI+: 343 |
| 20 | 20 | A/E+: 236 |
| 21 | 21 | ESI+: 350 |
| 22 | 22 | A/E+: 238 |
| 23 | 23 | ESI+: 237 |
| 24 | 24 | A/E+: 284, 286 |
| 25 | 25 | A/E+: 352 |
| 26 | 26 | FAB+: 282, 284 |
| 27 | 27 | ESI+: 300, 302 |
| 28 | 28 | ESI+: 329 |
| 29 | 29 | A/E+: 330 |
| 30 | 30 | A/E+: 272 |
| 31 | 31 | A/E+: 218 |
| 32 | 32 | A/E+: 219 |
| 33 | 33 | A/E+: 205 |
| 34 | 34 | A/E+: 235 |
| 35 | 35 | ESI+: 204 |
| 36 | 36 | A/E−: 304 |
| 37 | 37 | A/E+: 232 |
| 38 | 38 | A/E+: 222 |
| 39 | 39 | EI+: 274 |
| 40 | 11 | A/E+: 336 |
| 41 | 4 | EI+: 263 |
| 42 | 4 | EI+: 317 |
| 43 | 2 | ESI+: 250 |
| 44 | 2 | ESI+: 304 |
| 45 | 4 | EI+: 263 |
| 46 | 4 | EI+: 317 |
| 47 | 2 | ESI+: 250 |
| 48 | 2 | ESI+: 304 |
| 49 | 11 | ESI+: 364 |
| 50 | 4 | ESI+: 346 |
| 51 | 2 | ESI+: 318 |
| 52 | 4 | ESI+: 264 |
| 53 | 2 | ESI+: 250 |
| 54 | 4 | A/E+: 344 |
| 55 | 2 | ESI+: 316 |
| 56 | 4 | ESI+: 332 |
| 57 | 4 | ESI+: 332 |
| 58 | 4 | ESI+: 316 |
| 59 | 4 | ESI+: 289 |
| 60 | 2 | ESI+: 318 |
| 61 | 2 | ESI+: 318 |
| 62 | 2 | ESI+: 302 |
| 63 | 2 | ESI+: 275 |
| 64 | 4 | EI+: 334 |
| 65 | 2 | EI+: 320 |
| 66 | 4 | EI+: 333 |
| 67 | 4 | ESI+: 316 |
| 68 | 4 | ESI+: 316 |
| 69 | 2 | ESI+: 320 |
| 70 | 2 | ESI+: 302 |
| 71 | 2 | ESI+: 302 |
| 72 | 38 | A/E+: 218 |
| 73 | 11 | A/E+: 350 |
| 74 | 4 | EI+: 277 |
| 75 | 4 | EI+: 331 |
| 76 | 4 | ESI+: 332 |
| 77 | 4 | ESI+: 332 |
| 78 | 2 | ESI+: 264 |
| 79 | 2 | ESI+: 318 |
| 80 | 2 | ESI+: 318 |
| 81 | 2 | ESI+: 318 |
| 82 | 4 | ESI+: 316 |
| 83 | 4 | ESI+: 332 |
| 84 | 4 | ESI+: 316 |
| 85 | 4 | EI+: 333 |
| 86 | 4 | EI+: 315 |
| 87 | 4 | EI+: 315 |
| 88 | 2 | ESI+: 320 |
| 89 | 2 | ESI+: 302 |
| 90 | 2 | ESI+: 302 |
| 91 | 2 | A/E+: 302 |
| 92 | 2 | A/E+: 318 |
| 93 | 2 | A/E+: 302 |
| 94 | 4 | ESI+: 332 |
| 95 | 4 | ESI+: 332 |
| 96 | 4 | ESI+: 289 |
| 97 | 4 | A/E+: 348 |
| 98 | 4 | A/E+: 346 |
| 99 | 4 | A/E+: 366 |
| 100 | 2 | A/E+: 318 |
| 101 | 2 | A/E+: 318 |
| 102 | 2 | A/E+: 275 |
| 103 | 2 | ESI+: 334 |
| 104 | 2 | ESI+: 332 |
| 105 | 2 | ESI+: 352 |
| 106 | 4 | ESI+: 350 |
| 107 | 4 | ESI+: 400 |
| 108 | 2 | ESI+: 336 |
| 109 | 2 | ESI+: 386 |
| 110 | 4 | ESI+: 323 |
| 111 | 4 | ESI+: 350 |

TABLE 42

| PEx | Syn | Dat |
|---|---|---|
| 112 | 2 | ESI+: 336 |
| 113 | 2 | A/E−: 307 |
| 114 | 4 | A/E+: 314 |
| 115 | 4 | A/E+: 314 |
| 116 | 4 | ESI+: 289 |
| 117 | 4 | ESI+: 350 |
| 118 | 2 | ESI+: 300 |
| 119 | 2 | ESI+: 300 |
| 120 | 2 | ESI+: 275 |
| 121 | 2 | ESI+: 336 |
| 122 | 4 | ESI+: 294 |
| 123 | 4 | ESI+: 319 |
| 124 | 2 | ESI+: 280 |
| 125 | 2 | ESI+: 305 |
| 126 | 4 | EI+: 349 |
| 127 | 4 | EI+: 349 |
| 128 | 36 | ND |
| 129 | 2 | ESI+: 336 |

TABLE 42-continued

| PEx | Syn | Dat |
| --- | --- | --- |
| 130 | 2 | ESI+: 336 |
| 131 | 32 | A/E+: 218 |
| 132 | 35 | ND |
| 133 | 32 | A/E+: 238 |
| 134 | 11 | FAB+: 350 |
| 135 | 2 | ESI+: 320 |
| 136 | 4 | ESI+: 332 |
| 137 | 4 | A/E+: 330 |
| 138 | 2 | A/E+: 318 |
| 139 | 11 | ND |
| 140 | 4 | A/E+: 314 |
| 141 | 4 | A/E+: 330 |
| 142 | 2 | A/E+: 316 |
| 143 | 2 | A/E+: 300 |
| 144 | 4 | A/E+: 352 |
| 145 | 2 | A/E+: 316 |
| 146 | 2 | A/E+: 338 |
| 147 | 4 | ESI+: 307 |
| 148 | 4 | A/E+: 346 |
| 149 | 4 | A/E+: 314 |
| 150 | 36 | A/E−: 308 |
| 151 | 36 | A/E−: 358 |
| 152 | 11 | ESI+: 369 |
| 153 | 35 | ND |
| 154 | 2 | A/E+: 293 |
| 155 | 4 | ESI+: 352 |
| 156 | 2 | FAB+: 332 |
| 157 | 35 | A/E+: 258 |
| 158 | 32 | A/E+: 222 |
| 159 | 4 | A/E+: 330 |
| 160 | 4 | A/E+: 330 |
| 161 | 4 | A/E+: 296 |
| 162 | 4 | A/E+: 296 |
| 163 | 4 | A/E+: 346 |
| 164 | 32 | A/E+: 272 |
| 165 | 2 | ESI+: 337 |
| 166 | 2 | ESI+: 316 |
| 167 | 2 | ESI+: 316 |
| 168 | 2 | ESI+: 282 |
| 169 | 2 | ESI+: 282 |
| 170 | 2 | A/E+: 332 |
| 171 | 11 | ESI+: 354 |
| 172 | 11 | FAB+: 404 |
| 173 | 4 | A/E+: 346, 348 |
| 174 | 4 | A/E+: 336 |
| 175 | 9 | A/E+: 301 |
| 176 | 4 | ND |
| 177 | 2 | A/E+: 332, 334 |
| 178 | 2 | A/E+: 322 |
| 179 | 2 | A/E+: 372 |
| 180 | 2 | ESI+: 287 |
| 181 | 4 | A/E+: 346, 348 |
| 182 | 2 | A/E+: 332 |
| 183 | 4 | A/E+: 330 |
| 184 | 4 | A/E+: 316, 318 |
| 185 | 2 | A/E+: 316 |
| 186 | 4 | A/E+: 344 |
| 187 | 4 | ESI+: 330 |
| 188 | 2 | ESI+: 302 |
| 189 | 2 | ESI+: 330 |
| 190 | 2 | ESI+: 316 |
| 191 | 2 | A/E+: 304 |
| 192 | 4 | A/E+: 330 |
| 193 | 4 | A/E+: 316 |
| 194 | 2 | ND |
| 195 | 4 | ND |
| 196 | 2 | A/E+: 302 |
| 197 | 2 | A/E+: 254 |
| 198 | 4 | A/E+: 330 |
| 199 | 2 | A/E+: 316 |
| 200 | 11 | ESI+: 415, 417 |
| 201 | 4 | A/E+: 396, 398 |
| 202 | 4 | A/E+: 348 |
| 203 | 4 | A/E+: 282 |
| 204 | 2 | A/E+: 327 |
| 205 | 2 | A/E+: 334 |
| 206 | 2 | A/E+: 268 |
| 207 | 4 | A/E+: 330 |
| 208 | 4 | ND |
| 209 | 2 | A/E−: 314 |
| 210 | 5 | A/E+: 316 |
| 211 | 2 | A/E+: 296 |
| 212 | 4 | A/E+: 342 |
| 213 | 2 | A/E+: 302 |
| 214 | 4 | A/E+: 242 |
| 215 | 2 | A/E+: 328 |
| 216 | 2 | A/E+: 228 |
| 217 | 2 | A/E+: 320 |
| 218 | 5 | A/E+: 316 |
| 219 | 5 | A/E+: 298 |
| 220 | 2 | A/E+: 302 |
| 221 | 2 | A/E+: 284 |
| 222 | 4 | A/E+: 336 |

TABLE 43

| PEx | Syn | Dat |
| --- | --- | --- |
| 223 | 4 | A/E+: 318 |
| 224 | 4 | A/E+: 268 |
| 225 | 2 | ESI+: 322 |
| 226 | 2 | ESI+: 304 |
| 227 | 5 | A/E+: 262 |
| 228 | 2 | A/E+: 248 |
| 229 | 4 | A/E+: 342 |
| 230 | 2 | A/E+: 254 |
| 231 | 2 | A/E+: 321 |
| 232 | 2 | ESI+: 328 |
| 233 | 19 | A/E+: 329 |
| 234 | 4 | A/E+: 334 |
| 235 | 4 | ESI+: 334 |
| 236 | 4 | A/E+: 334 |
| 237 | 4 | A/E+: 318 |
| 238 | 4 | A/E+: 307 |
| 239 | 4 | A/E+: 344 |
| 240 | 4 | A/E+: 328 |
| 241 | 2 | ESI+: 320 |
| 242 | 2 | ESI+: 320 |
| 243 | 2 | ESI+: 304 |
| 244 | 2 | ESI+: 293 |
| 245 | 4 | A/E+: 328 |
| 246 | 4 | A/E+: 310 |
| 247 | 2 | A/E+: 300 |
| 248 | 2 | ESI+: 330 |
| 249 | 11 | ESI+: 364 |
| 250 | 2 | A/E+: 282 |
| 251 | 2 | A/E+: 300 |
| 252 | 4 | A/E+: 346 |
| 253 | 4 | A/E+: 328 |
| 254 | 4 | A/E+: 328 |
| 255 | 2 | ESI+: 332 |
| 256 | 2 | A/E+: 314 |
| 257 | 27 | A/E+: 334, 336 |
| 258 | 2 | A/E+: 314 |
| 259 | 22 | A/E+: 266 |
| 260 | 4 | A/E+: 368 |
| 261 | 11 | ESI+: 378 |
| 262 | 2 | A/E+: 354 |
| 263 | 4 | A/E+: 360 |
| 264 | 2 | A/E+: 332 |
| 265 | 2 | ESI+: 320 |
| 266 | 6 | A/E+: 358 |
| 267 | 2 | A/E+: 344 |
| 268 | 5 | A/E+: 362, 364 |
| 269 | 2 | ESI+: 334 |
| 270 | 5 | A/E+: 344 |
| 271 | 2 | A/E+: 316 |
| 272 | 4 | ND |
| 273 | 5 | A/E+: 302, 304 |
| 274 | 11 | A/E+: 404 |
| 275 | 37 | A/E+: 246 |
| 276 | 4 | ESI+: 386 |
| 277 | 4 | ESI+: 368 |

TABLE 43-continued

| PEx | Syn | Dat |
|---|---|---|
| 278 | 2 | A/E+: 288 |
| 279 | 22 | A/E+: 252 |
| 280 | 4 | A/E+: 344 |
| 281 | 24 | A/E+: 264, 266 |
| 282 | 2 | ESI+: 372 |
| 283 | 2 | ESI+: 354 |
| 284 | 5 | A/E+: 362, 364 |
| 285 | 5 | A/E+: 342 |
| 286 | 2 | A/E+: 330 |
| 287 | 2 | A/E+: 330 |
| 288 | 24 | A/E+: 270, 272 |
| 289 | 5 | A/E+: 328 |
| 290 | 5 | A/E+: 332, 334 |
| 291 | 5 | A/E+: 323, 325 |
| 292 | 5 | A/E+: 353, 355 |
| 293 | 2 | A/E+: 314, 316 |
| 294 | 2 | A/E+: 318, 320 |
| 295 | 5 | A/E+: 348, 350 |
| 296 | 5 | A/E+: 330, 332 |
| 297 | 5 | A/E+: 324 |
| 298 | 5 | A/E+: 276 |
| 299 | 2 | A/E+: 339, 341 |
| 300 | 2 | A/E−: 346, 348 |
| 301 | 2 | A/E+: 334, 336 |
| 302 | 2 | A/E+: 309 |
| 303 | 2 | A/E+: 316, 318 |
| 304 | 2 | A/E+: 207 |
| 305 | 2 | A/E+: 296 |
| 306 | 5 | A/E+: 317, 319 |
| 307 | 5 | A/E+: 329, 331 |
| 308 | 2 | A/E+: 262, 264 |
| 309 | 2 | A/E+: 303, 305 |
| 310 | 2 | A/E+: 315, 317 |
| 311 | 5 | A/E+: 288, 290 |
| 312 | 2 | A/E+: 274 |
| 313 | 11 | A/E+: 350 |
| 314 | 4 | A/E+: 332 |
| 315 | 11 | A/E+: 368 |
| 316 | 4 | A/E+: 350 |
| 317 | 2 | ESI+: 318 |
| 318 | 2 | ESI+: 336 |
| 319 | 2 | A/E+: 314 |
| 320 | 4 | A/E+: 314 |
| 321 | 5 | A/E+: 330, 332 |
| 322 | 5 | A/E+: 330, 332 |
| 323 | 2 | ESI+: 300 |
| 324 | 2 | A/E+: 316, 318 |
| 325 | 2 | A/E+: 316, 318 |
| 326 | 5 | A/E+: 362, 364 |
| 327 | 5 | A/E+: 346, 348 |
| 328 | 2 | A/E+: 348, 350 |
| 329 | 2 | ND |
| 330 | 5 | A/E+: 341 |
| 331 | 2 | A/E+: 327, 329 |
| 332 | 5 | A/E+: 344, 346 |
| 333 | 11 | FAB+: 378 |

TABLE 44

| PEx | Syn | Dat |
|---|---|---|
| 334 | 4 | A/E+: 360 |
| 335 | 2 | A/E+: 316, 318 |
| 336 | 2 | A/E+: 332 |
| 337 | 38 | A/E+: 204 |
| 338 | 11 | A/E+: 336 |
| 339 | 4 | A/E+: 300 |
| 340 | 2 | A/E+: 277, 279 |
| 341 | 4 | A/E+: 342 |
| 342 | 2 | ESI+: 286 |
| 343 | 2 | A/E+: 314 |
| 344 | 4 | A/E+: 358 |
| 345 | 4 | ESI+: 324 |
| 346 | 4 | A/E+: 361 |
| 347 | 4 | A/E+: 372 |

TABLE 44-continued

| PEx | Syn | Dat |
|---|---|---|
| 348 | 2 | ESI+: 296 |
| 349 | 37 | A/E+: 250 |
| 350 | 2 | A/E+: 333 |
| 351 | 2 | A/E+: 344 |
| 352 | 4 | A/E+: 340 |
| 353 | 4 | ESI+: 380 |
| 354 | 9 | A/E+: 319 |
| 355 | 11 | A/E+: 354 |
| 356 | 6 | ESI+: 340 |
| 357 | 2 | ESI+: 326 |
| 358 | 6 | ESI+: 340 |
| 359 | 2 | ESI+: 305 |
| 360 | 2 | A/E+: 330, 332 |
| 361 | 2 | A/E−: 310, 312 |
| 362 | 4 | A/E+: 358 |
| 363 | 4 | A/E+: 341, 343 |
| 364 | 4 | ESI+: 330 |
| 365 | 4 | ESI+: 300 |
| 366 | 4 | ESI+: 316 |
| 367 | 2 | ESI+: 316 |
| 368 | 2 | ESI+: 286 |
| 369 | 2 | ESI+: 302 |
| 370 | 11 | ESI+: 382 |
| 371 | 2 | ESI+: 328 |
| 372 | 4 | A/E+: 346 |
| 373 | 2 | A/E+: 330 |
| 374 | 4 | A/E+: 363, 364 |
| 375 | 2 | A/E+: 313 |
| 376 | 2 | A/E+: 318 |
| 377 | 4 | A/E+: 317 |
| 378 | 4 | A/E+: 362 |
| 379 | 2 | ND |
| 380 | 30 | A/E−: 270 |
| 381 | 4 | A/E+: 354 |
| 382 | 2 | A/E+: 334, 336 |
| 383 | 4 | A/E+: 328 |
| 384 | 2 | ESI+: 303 |
| 385 | 2 | A/E+: 300 |
| 386 | 4 | A/E+: 346 |
| 387 | 2 | A/E+: 326 |
| 388 | 2 | A/E+: 320 |
| 389 | 2 | A/E+: 332, 334 |
| 390 | 4 | A/E+: 350, 352 |
| 391 | 4 | A/E+: 332, 334 |
| 392 | 2 | A/E+: 318 |
| 393 | 2 | A/E+: 336, 338 |
| 394 | 9 | A/E+: 335 |
| 395 | 4 | ESI+: 301 |
| 396 | 2 | ESI+: 321 |
| 397 | 2 | ESI+: 287 |
| 398 | 4 | A/E+: 317 |
| 399 | 4 | A/E+: 333, 335 |
| 400 | 9 | A/E+: 335 |
| 401 | 11 | ESI+: 404 |
| 402 | 2 | ESI+: 321 |
| 403 | 2 | A/E+: 319, 321 |
| 404 | 4 | A/E+: 316, 318 |
| 405 | 4 | A/E+: 346 |
| 406 | 4 | A/E+: 353, 355 |
| 407 | 2 | A/E+: 303 |
| 408 | 2 | A/E+: 332, 334 |
| 409 | 4 | A/E+: 362, 364 |
| 410 | 17 | A/E+: 328 |
| 411 | 6 | ESI+: 314 |
| 412 | 2 | A/E+: 302, 304 |
| 413 | 2 | A/E+: 300 |
| 414 | 2 | A/E+: 339, 341 |
| 415 | 4 | ESI+: 350 |
| 416 | 2 | ESI+: 314 |
| 417 | 2 | A/E+: 348, 350 |
| 418 | 9 | A/E+: 351 |
| 419 | 2 | ESI+: 336 |
| 420 | 4 | A/E+: 350, 352 |
| 421 | 2 | ESI+: 337 |
| 422 | 4 | ESI+: 300 |
| 423 | 4 | ESI+: 350 |
| 424 | 4 | ESI+: 350 |
| 425 | 4 | ESI+: 350 |

TABLE 44-continued

| PEx | Syn | Dat |
|---|---|---|
| 426 | 2 | ESI+: 286 |
| 427 | 2 | ESI+: 336 |
| 428 | 2 | ESI+: 336 |
| 429 | 2 | ESI+: 336 |
| 430 | 4 | A/E+: 362, 364 |
| 431 | 4 | A/E+: 366, 368 |
| 432 | 4 | A/E+: 334, 336 |
| 433 | 4 | A/E+: 330, 332 |
| 434 | 5 | A/E+: 360, 362 |
| 435 | 2 | A/E+: 316, 318 |
| 436 | 4 | ESI+: 282 |
| 437 | 4 | ESI+: 296 |
| 438 | 4 | ESI+: 300 |
| 439 | 4 | ESI+: 316 |
| 440 | 5 | A/E+: 379, 380 |
| 441 | 4 | A/E+: 262, 264 |
| 442 | 4 | A/E+: 298, 300 |
| 443 | 6 | ESI+: 326 |
| 444 | 2 | A/E+: 348, 350 |

TABLE 45

| PEx | Syn | Dat |
|---|---|---|
| 445 | 4 | A/E+: 368 |
| 446 | 2 | ESI+: 268 |
| 447 | 2 | ESI+: 282 |
| 448 | 2 | ESI+: 286 |
| 449 | 2 | ESI+: 302 |
| 450 | 4 | A/E+: 350, 352 |
| 451 | 16 | ESI+: 328 |
| 452 | 4 | ESI+: 332 |
| 453 | 2 | A/E+: 284, 286 |
| 454 | 2 | ESI+: 336 |
| 455 | 2 | A/E+: 336, 338 |
| 456 | 2 | ESI+: 318 |
| 457 | 2 | A/E+: 354 |
| 458 | 2 | A/E+: 332, 334 |
| 459 | 4 | ESI+: 360, 362 |
| 460 | 4 | ESI+: 376, 378, 380 |
| 461 | 4 | ESI+: 334 |
| 462 | 2 | A/E+: 248, 250 |
| 463 | 4 | ESI+: 334 |
| 464 | 6 | A/E+: 312, 314 |
| 465 | 2 | ESI+: 352, 354, 356 |
| 466 | 2 | ESI+: 320, 322 |
| 467 | 4 | ESI+: 366, 368, 370 |
| 468 | 4 | ESI+: 334, 336 |
| 469 | 2 | A/E+: 351, 353 |
| 470 | 2 | A/E+: 320, 322 |
| 471 | 2 | ESI+: 320 |
| 472 | 2 | ESI+: 320 |
| 473 | 2 | A/E+: 350, 352 |
| 474 | 2 | ESI+: 282 |
| 475 | 2 | A/E+: 315 |
| 476 | 2 | ND |
| 477 | 15 | ESI+: 330 |
| 478 | 2 | A/E+: 316 |
| 479 | 4 | ESI+: 394, 396, 398 |
| 480 | 6 | ESI+: 330, 332 |
| 481 | 4 | A/E+: 352, 354 |
| 482 | 4 | A/E+: 334, 336 |
| 483 | 14 | A/E+: 371 |
| 484 | 4 | ESI+: 361, 363 |
| 485 | 6 | A/E+: 315 |
| 486 | 2 | ESI+: 338, 340 |
| 487 | 2 | A/E+: 320, 322 |
| 488 | 4 | A/E+: 350, 352 |
| 489 | 4 | ESI+: 330 |
| 490 | 4 | ESI+: 346 |
| 491 | 4 | ESI+: 346 |
| 492 | 4 | ESI+: 318 |
| 493 | 2 | ESI+: 336, 338 |
| 494 | 2 | ESI+: 316, 318 |
| 495 | 4 | ESI+: 312, 314 |

TABLE 45-continued

| PEx | Syn | Dat |
|---|---|---|
| 496 | 4 | ESI+: 330 |
| 497 | 2 | ND |
| 498 | 2 | ESI+: 316 |
| 499 | 2 | ESI+: 332 |
| 500 | 2 | ESI+: 332 |
| 501 | 2 | ESI+: 304 |
| 502 | 6 | ESI+: 297 |
| 503 | 4 | ESI+: 326 |
| 504 | 2 | ESI+: 298 |
| 505 | 2 | ESI+: 283 |
| 506 | 2 | ESI+: 316, 318 |
| 507 | 2 | ESI+: 312, 315 |
| 508 | 12 | ESI+: 302 |
| 509 | 12 | ESI+: 318 |
| 510 | 6 | ESI+: 308 |
| 511 | 9 | ESI+: 379, 381 |
| 512 | 17 | ESI+: 310 |
| 513 | 16 | ESI+: 310 |
| 514 | 21 | ESI+: 332 |
| 515 | 6 | ESI+: 327 |
| 516 | 2 | ESI+: 318 |
| 517 | 16 | ESI+: 329 |
| 518 | 21 | ESI+: 351 |
| 519 | 2 | ESI+: 337 |
| 520 | 2 | ESI+: 296 |

TABLE 46

| PEx | Dat (NMR) |
|---|---|
| 128 | DMSO-d$_6$: 1.70 (6H, s), 7.94-7.96 (1H, m), 8.04-8.06 (2H, m), 8.84-8.87 (1H, m), 11.65-11.68 (1H, brs) |
| 139 | CDCl$_3$: 4.04 (3H, s), 7.60 (1H, d, J = 6 Hz), 8.57 (1H, s), 8.74 (1H, s), 9.20 (1H, d, J = 6 Hz) |
| 208 | CDCl$_3$: 1.54 (6H, s), 3.93 (3H, s), 7.23-7.35 (3H, m), 7.40 (1H, d, J = 4 Hz), 8.19 (1H, s), 8.23 (1H, s), 9.08 (1H, d, J = 4 Hz) |
| 272 | CDCl$_3$: 2.83 (3H, s), 2.88 (3H, s), 3.89 (3H, s), 7.18-7.27 (2H, m), 7.41-7.45 (2H, m), 7.98 (1H, s), 8.14 (1H, s) |

TABLE 47

| Ex | Sal | Str |
|---|---|---|
| 1 | 2HCl | 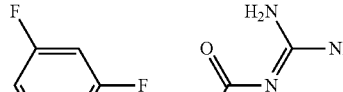 |
| 2 | Fum |  |

TABLE 47-continued

| Ex | Sal | Str |
|---|---|---|
| 3 | 2HCl | (structure) |
| 4 | 2HCl | (structure) |
| 5 | 2HCl | (structure) |
| 6 | 2HCl | (structure) |
| 7 | 2HCl | (structure) |
| 8 | 2HCl | (structure) |
| 9 | 2HCl | (structure) |
| 10 | 2HCl | (structure) |
| 11 | 2HCl | (structure) |
| 12 | 2HCl | (structure) |
| 13 | 2HCl | (structure) |

TABLE 48

| Ex | Sal | Str |
|---|---|---|
| 14 | 2HCl | (structure) |

TABLE 48-continued
| Ex | Sal | Str |
|---|---|---|
| 15 | 2HCl | 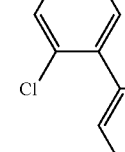 |
| 16 | 2HCl | 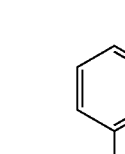 |
| 17 | 2HCl | 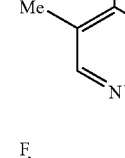 |
| 18 | 2HCl | 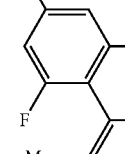 |
| 19 | 2HCl | 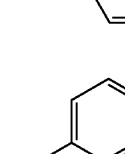 |
| 20 | 2HCl | 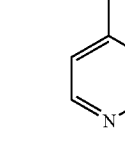 |
TABLE 48-continued
| Ex | Sal | Str |
|---|---|---|
| 21 | 2HCl | 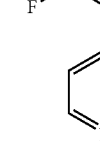 |
| 22 | 2HCl | 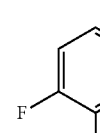 |
| 23 | 2HCl | 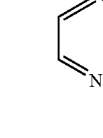 |
| 24 | 2HCl | 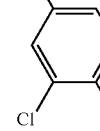 |
| 25 | HCl | 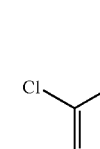 |
| 26 | 2HCl | 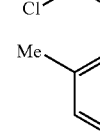 |

TABLE 48-continued

| Ex | Sal | Str |
|----|-----|-----|
| 27 | HCl | (2,4,6-trichlorophenyl quinoline carboxamide guanidine) |

TABLE 49

| Ex | Sal | Str |
|----|-----|-----|
| 28 | HCl | (3-trifluoromethyl-2-fluorophenyl quinoline carboxamide guanidine) |
| 29 | HCl | (2,4,6-trifluorophenyl quinoline N-oxide carboxamide guanidine) |
| 30 | HCl | (2,4,6-trifluorophenyl quinoline-2-carboxamide carboxamide guanidine) |
| 31 | HCl | (2,4-difluorophenyl-3-methylquinoline carboxamide guanidine) |
| 32 | 2HCl | (2,6-difluorophenyl-3-methylquinoline carboxamide guanidine) |
| 33 | 2HCl | (4-cyanophenyl quinoline carboxamide guanidine) |
| 34 | HCl | (4-trifluoromethyl-2-fluorophenyl quinoline carboxamide guanidine) |
| 35 | 2HCl | (2-methoxyphenyl quinoline carboxamide guanidine) |
| 36 | 2HCl | (4-cyano-2-methoxyphenyl quinoline carboxamide guanidine) |
| 37 | 2HCl | (3-trifluoromethyl-4-fluorophenyl quinoline carboxamide guanidine) |

TABLE 49-continued

| Ex | Sal | Str |
|---|---|---|
| 38 | 2HCl | (structure) |
| 39 | 2HCl | (structure) |

TABLE 50

| Ex | Sal | Str |
|---|---|---|
| 40 | 2HCl | (structure) |
| 41 | 2HCl | (structure) |
| 42 | 2HCl | (structure) |

TABLE 50-continued

| Ex | Sal | Str |
|---|---|---|
| 43 | 2HCl | (structure) |
| 44 | 2HCl | (structure) |
| 45 | 2HCl | (structure) |
| 46 | 2HCl | (structure) |
| 47 | 2HCl | (structure) |
| 48 | 2HCl | (structure) |

TABLE 50-continued
| Ex | Sal | Str |
|---|---|---|
| 49 | 2HCl | 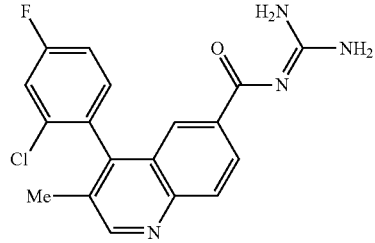 [SMILES: Cc1cnc2ccc(C(=O)N=C(N)N)cc2c1-c1ccc(F)cc1Cl] |
| 50 | 2HCl | 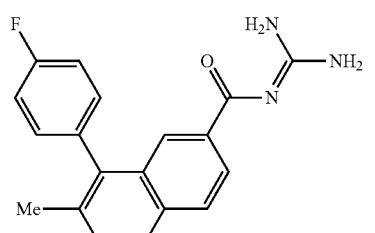 |
| 51 | 2HCl | 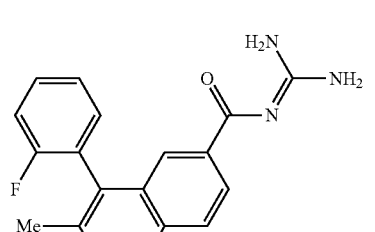 |
TABLE 51
| Ex | Sal | Str |
|---|---|---|
| 52 | 3HCl | 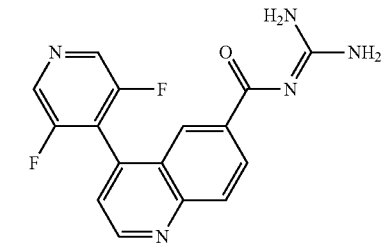 [SMILES: NC(N)=NC(=O)c1ccc2nccc(-c3c(F)cncc3F)c2c1] |
| 53 | HCl | 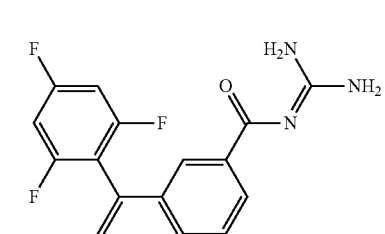 |
| 54 | 2HCl | 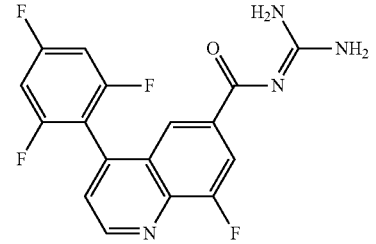 [SMILES: NC(N)=NC(=O)c1cc(F)c2nccc(-c3c(F)cc(F)cc3F)c2c1] |
| 55 | 2HCl | 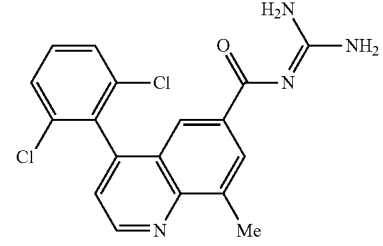 [SMILES: Cc1cc(C(=O)N=C(N)N)cc2c(-c3c(Cl)cccc3Cl)ccnc12] |
| 56 | 2HCl | 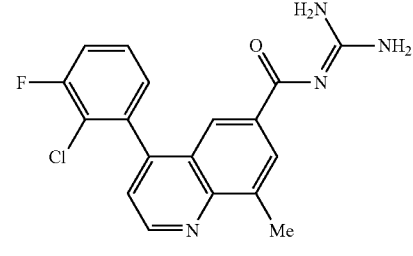 [SMILES: Cc1cc(C(=O)N=C(N)N)cc2c(-c3cccc(F)c3Cl)ccnc12] |
| 57 | 2HCl | 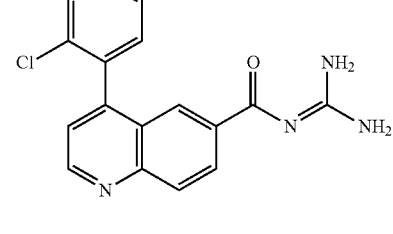 |
| 58 | 2HCl | 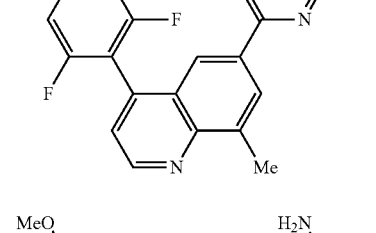 |
| 59 | 2HCl | 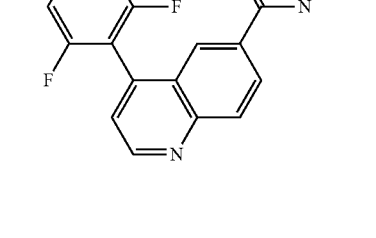 |

TABLE 51-continued
| Ex | Sal | Str |
|---|---|---|
| 60 | 2HCl | 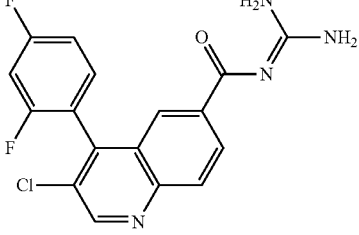 |
| 61 | 2HCl | 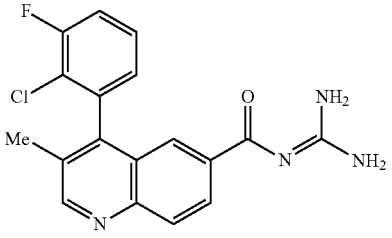 |
| 62 | 2HCl | 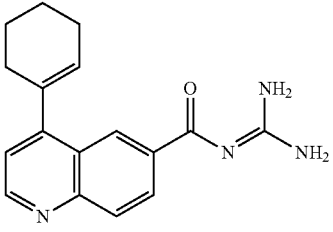 [SMILES: NC(N)=NC(=O)c1ccc2nccc(C3=CCCCC3)c2c1] |
| 63 | 2HCl | 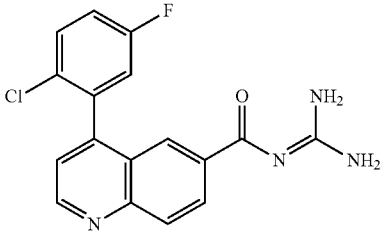 [SMILES: NC(N)=NC(=O)c1ccc2nccc(-c3cc(F)ccc3Cl)c2c1] |
| 64 | 2HCl | 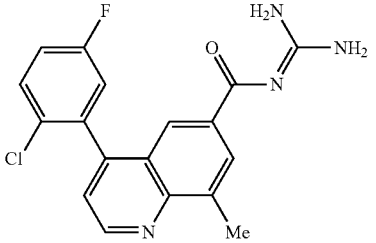 [SMILES: Cc1cc(C(=O)N=C(N)N)cc2c(-c3cc(F)ccc3Cl)ccnc12] |
TABLE 52
| Ex | Sal | Str |
|---|---|---|
| 65 | 2HCl | 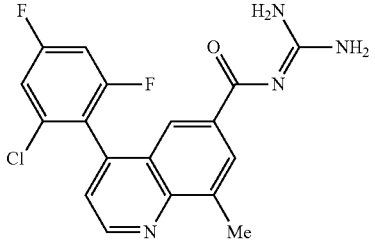 [SMILES: Cc1cc(C(=O)N=C(N)N)cc2c(-c3c(F)cc(F)cc3Cl)ccnc12] |
TABLE 52-continued
| Ex | Sal | Str |
|---|---|---|
| 66 | 2HCl | 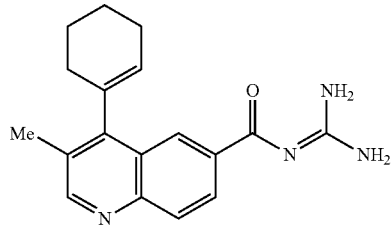 [SMILES: Cc1cnc2ccc(C(=O)N=C(N)N)cc2c1C1=CCCCC1] |
| 67 | 2HCl | 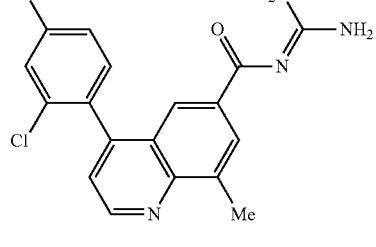 |
| 68 | 2HCl | 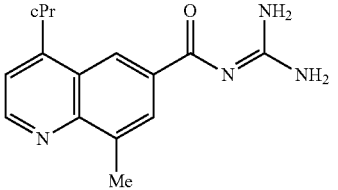 |
| 69 | 2HCl | |
| 70 | 2HCl | |
| 71 | 2HCl | |

TABLE 52-continued
| Ex | Sal | Str |
|----|-----|-----|
| 72 | — | 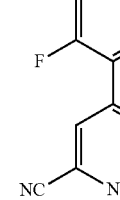 |
| 73 | 2HCl | |
| 74 | 2HCl | |
| 75 | 2HCl | |
| 76 | 2HCl | |
| 77 | 2HCl | |
TABLE 52-continued
| Ex | Sal | Str |
|----|-----|-----|
| 78 | 2HCl | 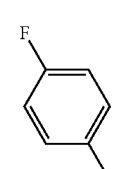 |
TABLE 53
| Ex | Sal | Str |
|----|-----|-----|
| 79 | 2HCl | 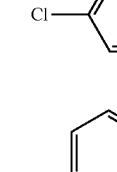 |
| 80 | 2HCl | |
| 81 | 2HCl | |
| 82 | 2HCl | |

TABLE 53-continued
| Ex | Sal | Str |
|---|---|---|
| 83 | 2HCl | 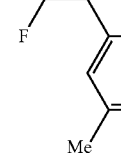 |
| 84 | 2HCl | 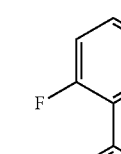 |
| 85 | 2HCl | 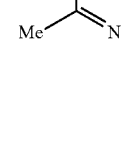 |
| 86 | 2HCl | 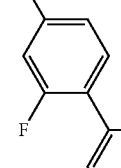 |
| 87 | 2HCl | 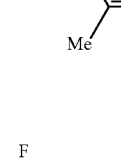 |
TABLE 53-continued
| Ex | Sal | Str |
|---|---|---|
| 88 | 2HCl | 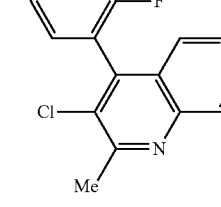 |
| 89 | 2HCl | 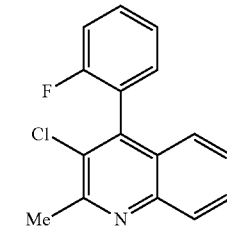 |
| 90 | Fum | 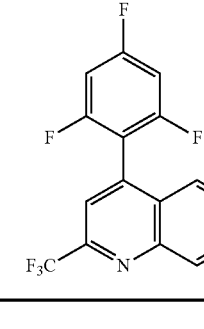 |
TABLE 54
| Ex | Sal | Str |
|---|---|---|
| 91 | HCl | 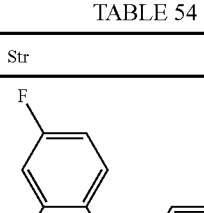 |
| 92 | Fum | 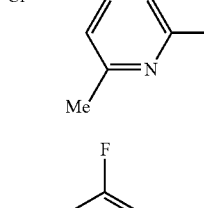 |

TABLE 54-continued

| Ex | Sal | Str |
|---|---|---|
| 93 | 2HCl | (structure) |
| 94 | 2HCl | (structure) |
| 95 | 2HCl | (structure) |
| 96 | 2HCl | (structure) |
| 97 | 2HCl | (structure) |
| 98 | 2HCl | (structure) |
| 99 | 2HCl | (structure) |
| 100 | 2HCl | (structure) |
| 101 | 2HCl | (structure) |
| 102 | 2HCl | (structure) |
| 103 | 2HCl | (structure) |

TABLE 55

| Ex | Sal | Str |
|---|---|---|
| 104 | 3HCl | (structure) |

TABLE 55-continued
| Ex | Sal | Str |
|---|---|---|
| 105 | 2HCl | 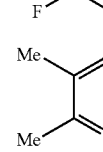 |
| 106 | 3HCl | 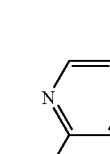 |
| 107 | 2HCl | 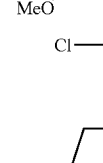 |
| 108 | 2HCl | 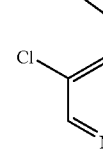 |
| 109 | 2HCl | 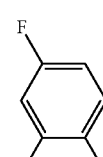 |
| 110 | 2HCl | 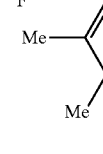 |
| 111 | 2HCl | 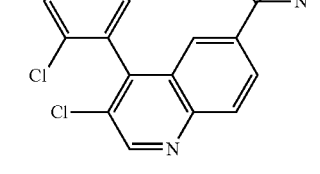 |
| 112 | 2HCl | 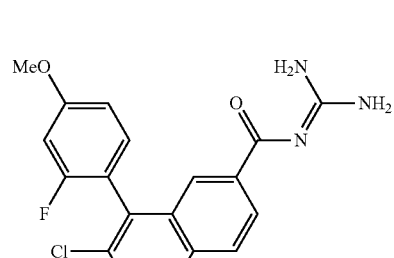 |
| 113 | 2HCl | 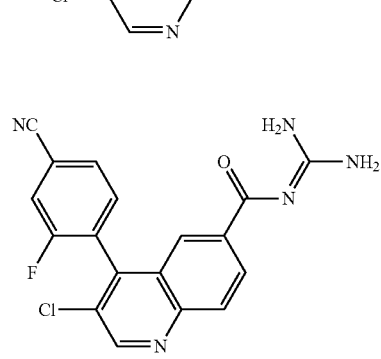 |
| 114 | 2HCl | 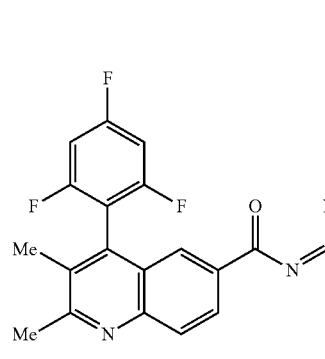 |
| 115 | 2HCl | 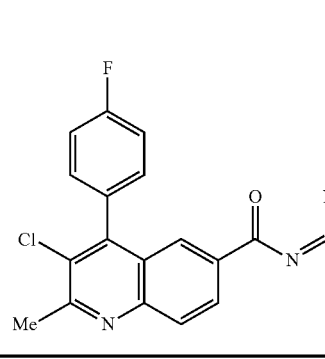 |

TABLE 56

| Ex | Sal | Str |
|---|---|---|
| 116 | 2HCl | |
| 117 | 2HCl | |
| 118 | 2HCl | |
| 119 | 2HCl | |
| 120 | 2HCl | |
| 121 | 2HCl | |

TABLE 56-continued

| Ex | Sal | Str |
|---|---|---|
| 122 | 2HCl | |
| 123 | 2HCl | |
| 124 | 2HCl | |
| 125 | 2HCl | |
| 126 | 2HCl | |
| 127 | 3HCl | |

TABLE 57
| Ex | Sal | Str |
|---|---|---|
| 128 | 2HCl | 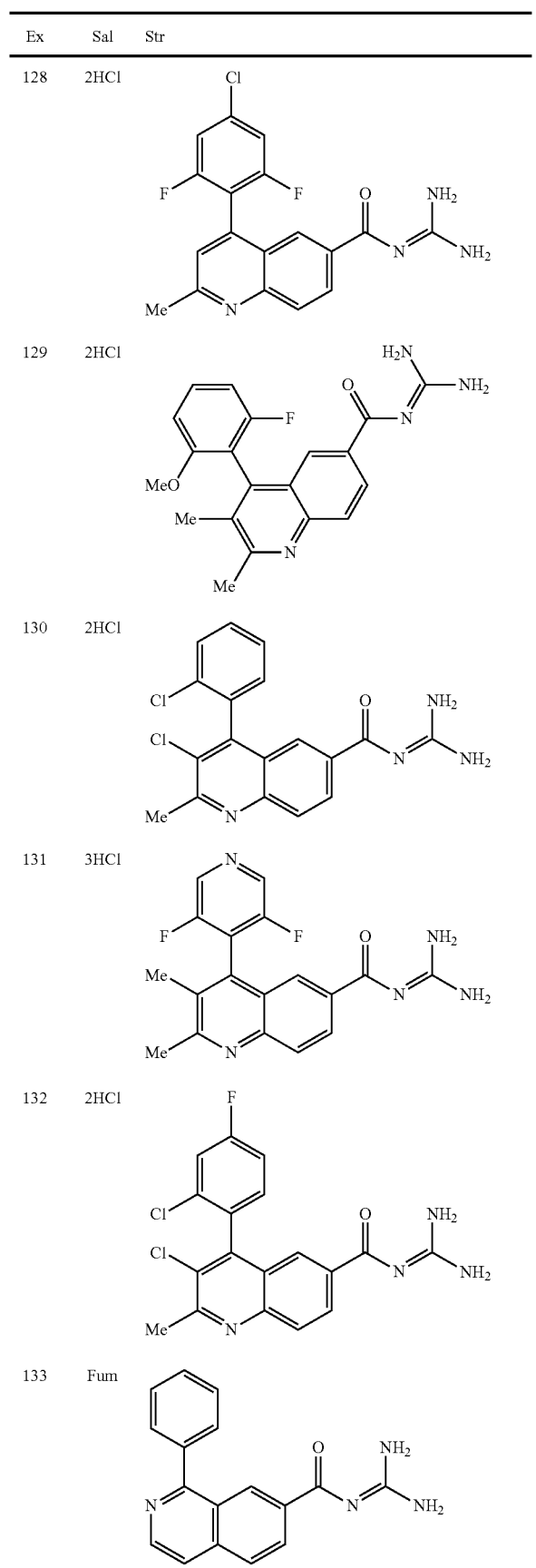 |
| 129 | 2HCl | |
| 130 | 2HCl | |
| 131 | 3HCl | |
| 132 | 2HCl | |
| 133 | Fum | |
TABLE 57-continued
| Ex | Sal | Str |
|---|---|---|
| 134 | 2HCl | 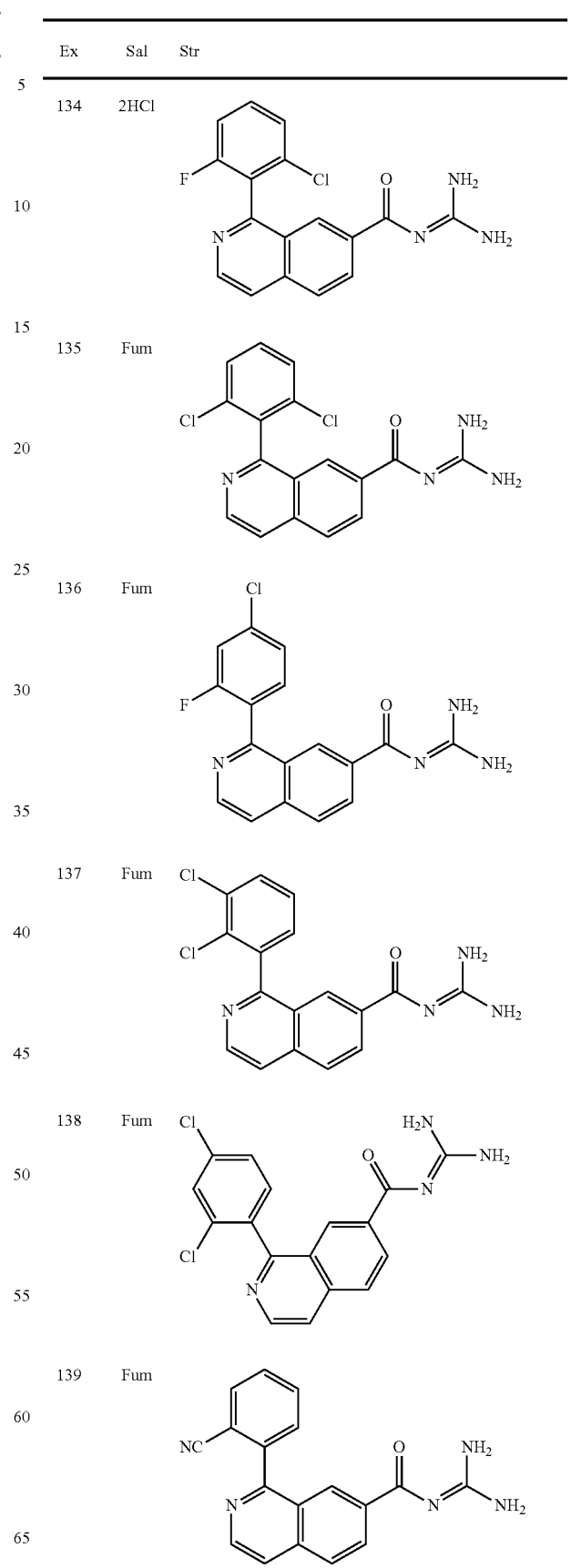 |
| 135 | Fum | |
| 136 | Fum | |
| 137 | Fum | |
| 138 | Fum | |
| 139 | Fum | |

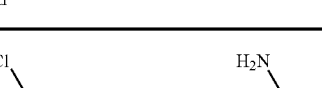

TABLE 58-continued

| Ex | Sal | Str |
|---|---|---|
| 150 | Fum | (4-cyanophenyl group at position 1, F at position 4 of isoquinoline, 7-carboxamide-N-guanidine) |
| 151 | Fum | (2-chloro-4-fluorophenyl at position 1, F at position 4 of isoquinoline, 7-carboxamide-N-guanidine) |
| 152 | Fum | (2,6-difluoro-4-fluorophenyl at position 1, Me at position 4 of isoquinoline, 7-carboxamide-N-guanidine) |

TABLE 59

| Ex | Sal | Str |
|---|---|---|
| 153 | Fum | (2,4,6-trifluorophenyl at position 1, Me at position 3 of isoquinoline, 7-carboxamide-N-guanidine) |
| 154 | Fum | (2,4,6-trifluorophenyl at position 1, Me at position 3, F at position 4 of isoquinoline, 7-carboxamide-N-guanidine) |

TABLE 59-continued

| Ex | Sal | Str |
|---|---|---|
| 155 | Fum | (2,6-difluorophenyl at position 1, Me at position 3 of isoquinoline, 7-carboxamide-N-guanidine) |
| 156 | Fum | (2,6-difluorophenyl at position 1, cPr at position 4 of isoquinoline, 7-carboxamide-N-guanidine) |
| 157 | Fum | (3,5-difluoropyridin-4-yl at position 1, F at position 4 of isoquinoline, 7-carboxamide-N-guanidine) |
| 158 | Fum | (2,6-difluorophenyl at position 1, iPr at position 4 of isoquinoline, 7-carboxamide-N-guanidine) |
| 159 | Fum | (2-fluoro-6-methoxyphenyl at position 1, F at position 4 of isoquinoline, 7-carboxamide-N-guanidine) |

TABLE 59-continued

| Ex | Sal | Str |
|---|---|---|
| 160 | Fum | |
| 161 | Fum | |
| 162 | Fum | |
| 163 | Fum | |
| 164 | Fum | |

TABLE 60

| Ex | Sal | Str |
|---|---|---|
| 165 | Fum | |
| 166 | Fum | |
| 167 | Fum | |
| 168 | Fum | |
| 169 | Fum | |

TABLE 60-continued
| Ex | Sal | Str |
|---|---|---|
| 170 | Fum | 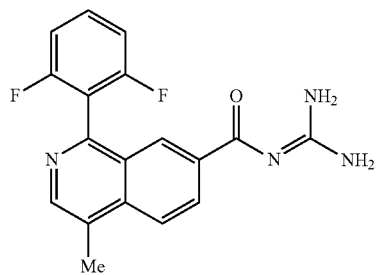 [SMILES: CC(C)c1cnc(-c2c(F)cccc2F)c2cc(C(=O)N=C(N)N)ccc12] |
| 171 | Fum | 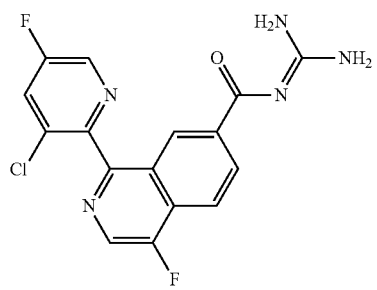 [SMILES: NC(N)=NC(=O)c1ccc2c(F)cnc(-c3ncc(F)cc3Cl)c2c1] |
| 172 | Fum | 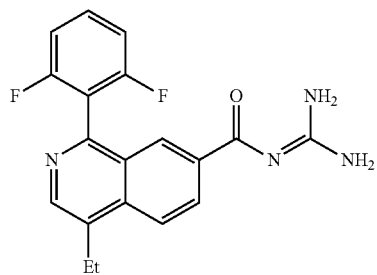 |
| 173 | Fum | 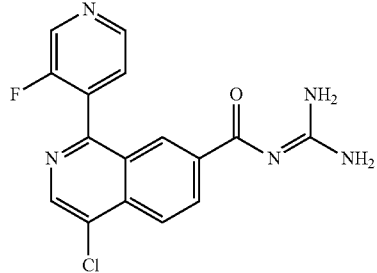 [SMILES: NC(N)=NC(=O)c1ccc2c(Cl)cnc(-c3ccncc3F)c2c1] |
| 174 | Fum | 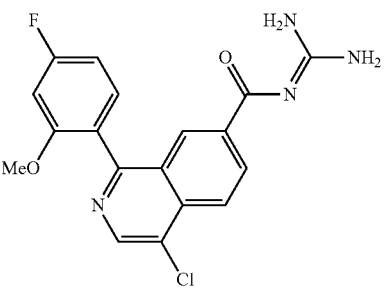 |
TABLE 60-continued
| Ex | Sal | Str |
|---|---|---|
| 175 | Fum | 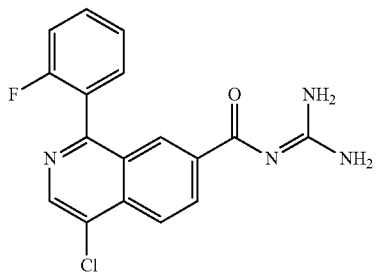 [SMILES: NC(N)=NC(=O)c1ccc2c(Cl)cnc(-c3ccccc3F)c2c1] |
| 176 | Fum | 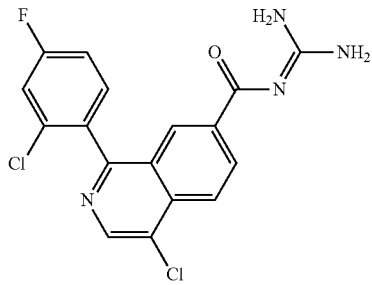 [SMILES: NC(N)=NC(=O)c1ccc2c(Cl)cnc(-c3ccc(F)cc3Cl)c2c1] |
TABLE 61
| Ex | Sal | Str |
|---|---|---|
| 177 | Fum | 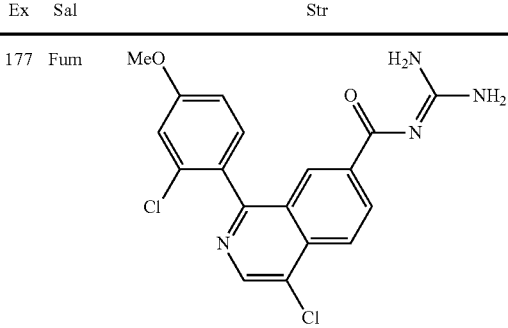 |
| 178 | Fum | 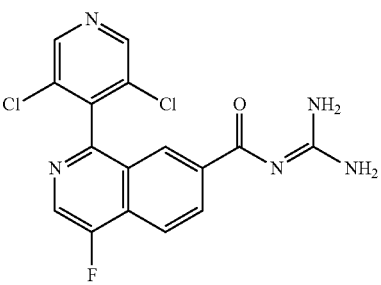 [SMILES: NC(N)=NC(=O)c1ccc2c(F)cnc(-c3c(Cl)cncc3Cl)c2c1] |
| 179 | Fum | 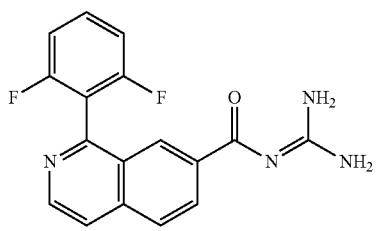 [SMILES: NC(N)=NC(=O)c1ccc2ccnc(-c3c(F)cccc3F)c2c1] |

TABLE 61-continued

| Ex | Sal | Str |
|---|---|---|
| 180 | Fum | (structure) |
| 181 | Fum | (structure) |
| 182 | Fum | (structure) |
| 183 | Fum | (structure) |
| 184 | Fum | (structure) |

TABLE 61-continued

| Ex | Sal | Str |
|---|---|---|
| 185 | Fum | (structure) |
| 186 | Fum | (structure) |
| 187 | Fum | (structure) |
| 188 | Fum | (structure) |

TABLE 62

| Ex | Sal | Str |
|---|---|---|
| 189 | Fum | (structure) |

TABLE 62-continued
| Ex | Sal | Str |
|----|-----|-----|
| 190 | Fum | 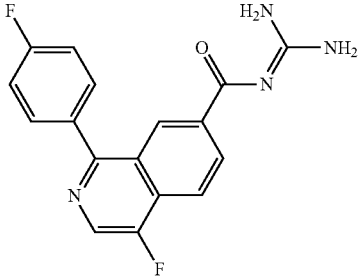 [SMILES: NC(N)=NC(=O)c1ccc2c(F)cnc(-c3ccc(F)cc3)c2c1] |
| 191 | Fum | 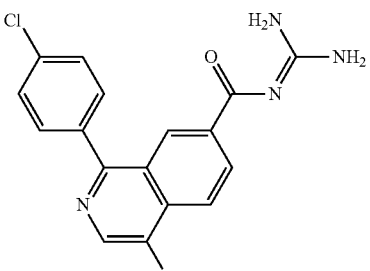 |
| 192 | Fum | 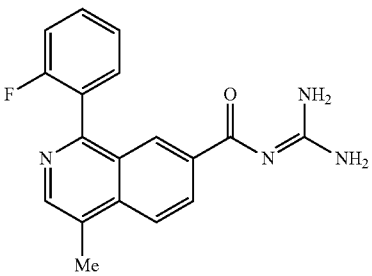 |
| 193 | Fum | 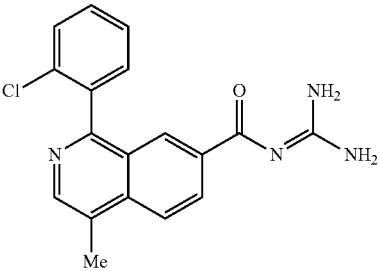 [SMILES: Cc1cnc(-c2ccccc2Cl)c2cc(C(=O)N=C(N)N)ccc12] |
| 194 | Fum | 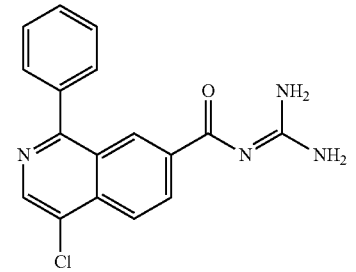 [SMILES: NC(N)=NC(=O)c1ccc2c(Cl)cnc(-c3ccccc3)c2c1] |
| 195 | Fum | 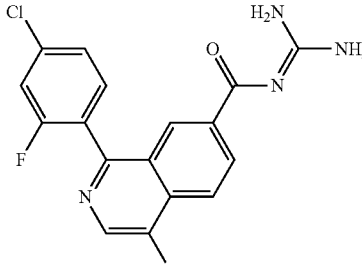 |
| 196 | Fum | 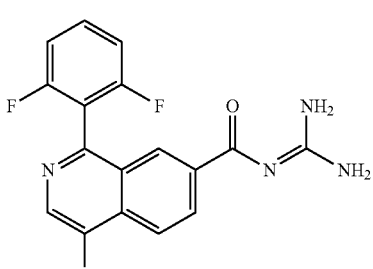 |
| 197 | HCl | 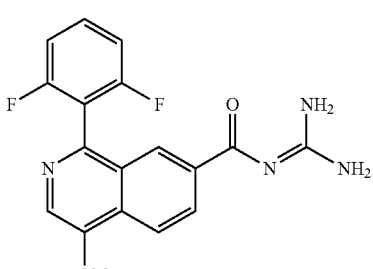 |
| 198 | Fum | 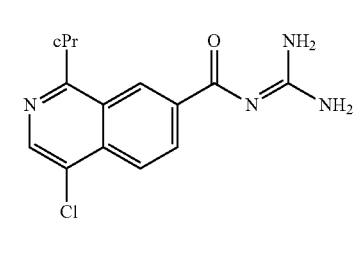 |
| 199 | Fum | 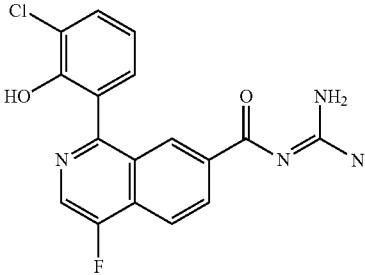 |

TABLE 62-continued
| Ex | Sal | Str |
|---|---|---|
| 200 | Fum | 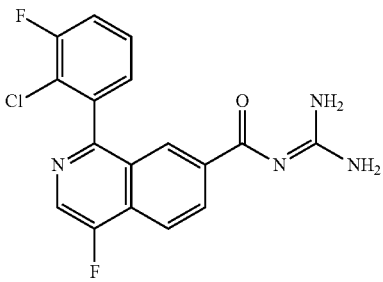 [SMILES: NC(N)=NC(=O)c1ccc2c(F)cnc(-c3cccc(F)c3Cl)c2c1] |
TABLE 63
| Ex | Sal | Str |
|---|---|---|
| 201 | Fum | 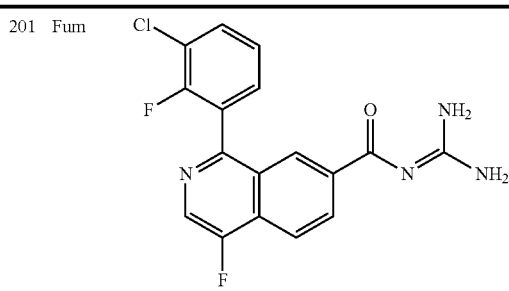 |
| 202 | Fum | 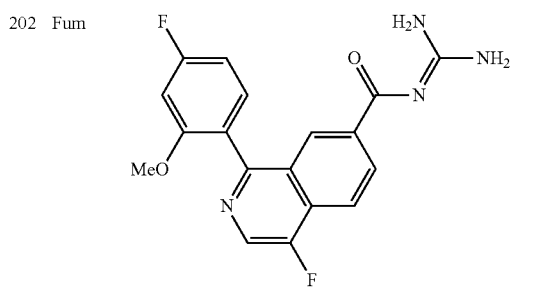 |
| 203 | Fum | 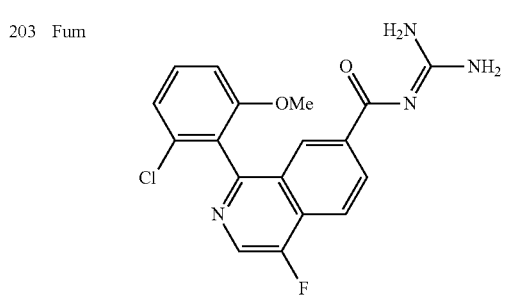 |
| 204 | Fum | 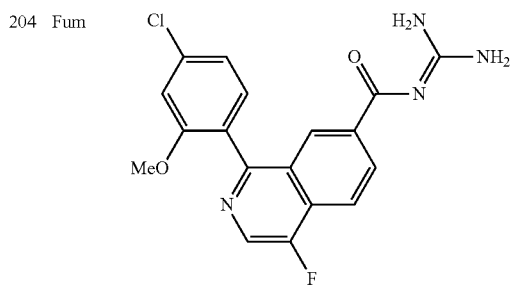 |
TABLE 63-continued
| Ex | Sal | Str |
|---|---|---|
| 205 | Fum | 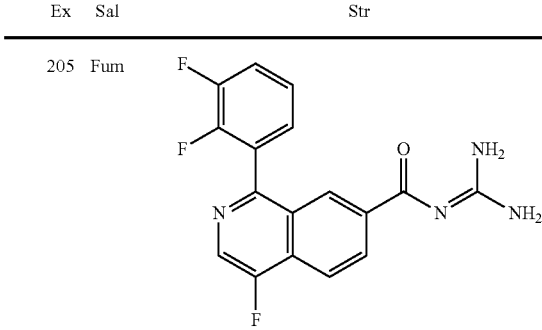 |
| 206 | Fum | 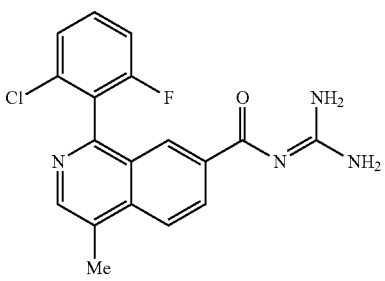 [SMILES: Cc1cnc(-c2c(F)cccc2Cl)c2cc(C(=O)N=C(N)N)ccc12] |
| 207 | Fum | 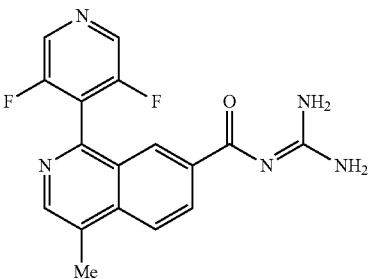 [SMILES: Cc1cnc(-c2c(F)cncc2F)c2cc(C(=O)N=C(N)N)ccc12] |
| 208 | Fum | 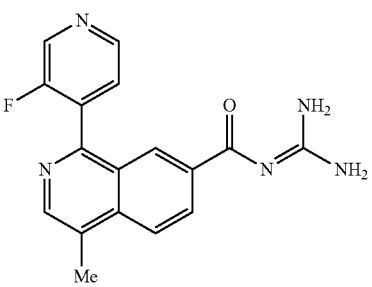 |
| 209 | 2HCl | 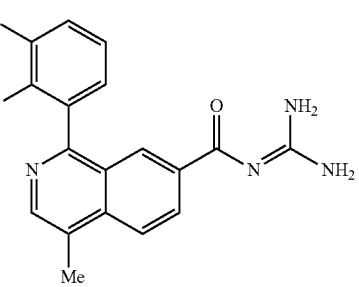 |

TABLE 63-continued
| Ex | Sal | Str |
|---|---|---|
| 210 | Fum | 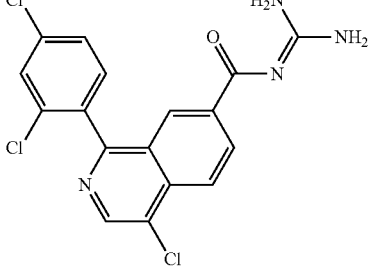 |
| 211 | Fum | 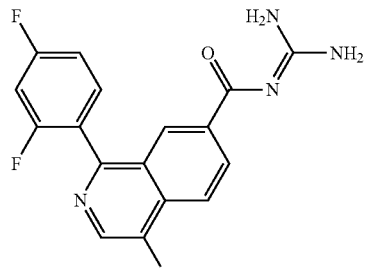 |
| 212 | Fum | 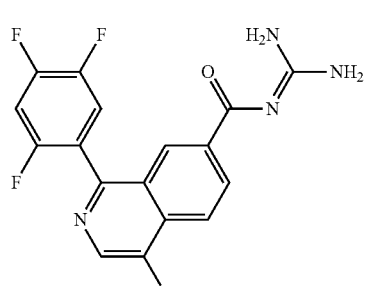 |
TABLE 64
| Ex | Sal | Str |
|---|---|---|
| 213 | Fum | 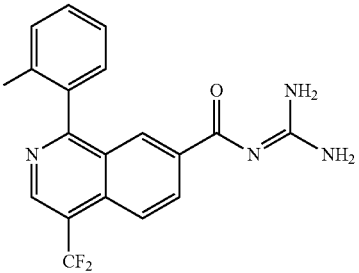 |
| 214 | Fum | 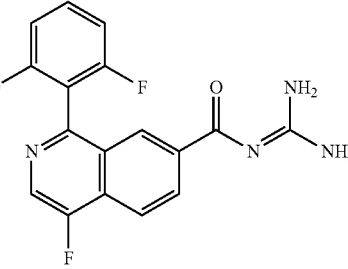 |
TABLE 64-continued
| Ex | Sal | Str |
|---|---|---|
| 215 | Fum | 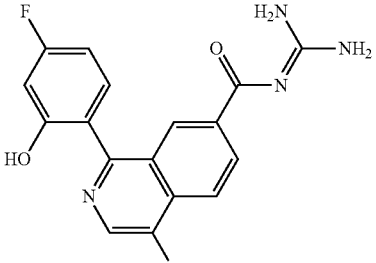 |
| 216 | Fum | 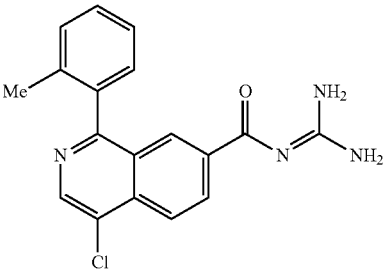 [SMILES: Cc1ccccc1-c1ncc(Cl)c2ccc(C(=O)N=C(N)N)cc12] |
| 217 | Fum | 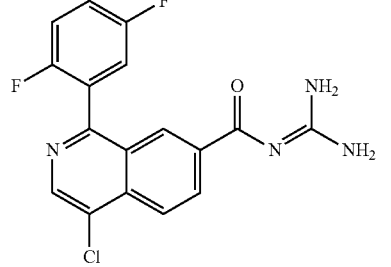 |
| 218 | Fum | 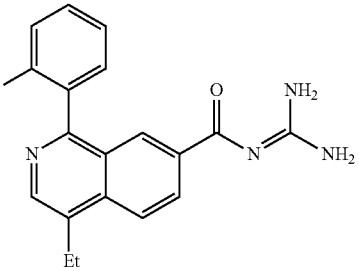 |
| 219 | Fum |  |

TABLE 64-continued
| Ex | Sal | Str |
|---|---|---|
| 220 | Fum | 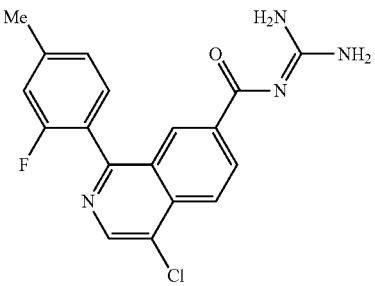 [SMILES: Cc1ccc(-c2ncc(Cl)c3ccc(C(=O)N=C(N)N)cc23)c(F)c1] |
| 221 | Fum | 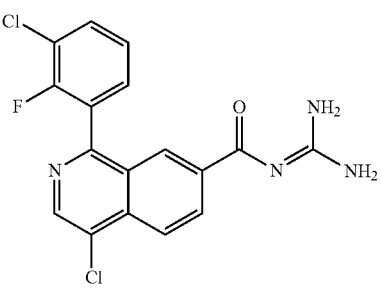 [SMILES: NC(N)=NC(=O)c1ccc2c(Cl)cnc(-c3cccc(Cl)c3F)c2c1] |
| 222 | Fum | 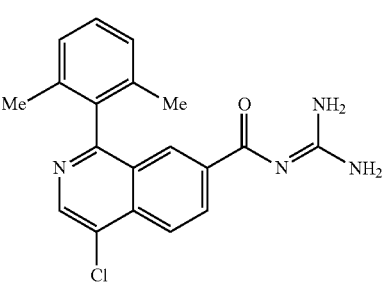 [SMILES: Cc1cccc(C)c1-c1ncc(Cl)c2ccc(C(=O)N=C(N)N)cc12] |
| 223 | Fum | 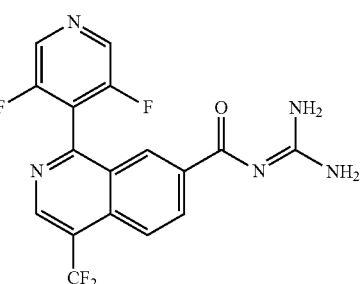 |
| 224 | Fum | 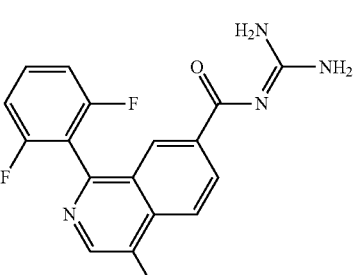 |
TABLE 65
| Ex | Sal | Str |
|---|---|---|
| 225 | HCl | 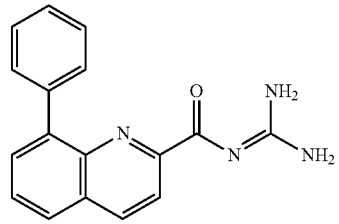 [SMILES: NC(N)=NC(=O)c1ccc2cccc(-c3ccccc3)c2n1] |
| 226 | HCl | 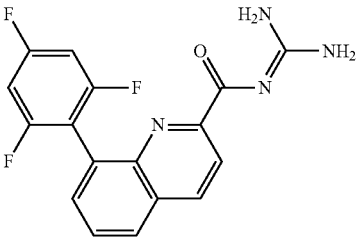 [SMILES: NC(N)=NC(=O)c1ccc2cccc(-c3c(F)cc(F)cc3F)c2n1] |
| 227 | 2HCl | 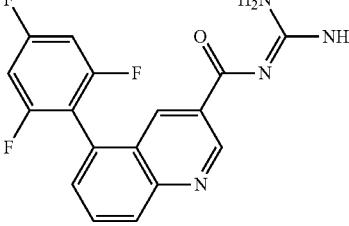 |
| 228 | Fum | 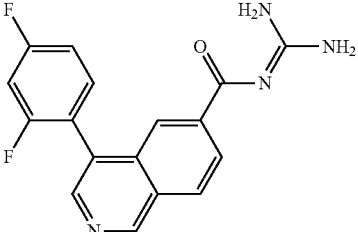 |
TABLE 66
| Ex | Dat |
|---|---|
| 1 | ESI+: 345 |
| 2 | ESI+: 375 |
| 3 | ESI+: 359 |
| 4 | ESI+: 291 |
| 5 | ESI+: 345 |
| 6 | ESI+: 359 |
| 7 | ESI+: 357 |
| 8 | ESI+: 361 |
| 9 | ESI+: 359 |
| 10 | ESI+: 359 |
| 11 | ESI+: 343 |
| 12 | ESI+: 316 |
| 13 | ESI+: 361 |
| 14 | ESI+: 343 |
| 15 | ESI+: 343 |
| 16 | ESI+: 305 |
| 17 | ESI+: 359 |
| 18 | ESI+: 359 |
| 19 | ESI+: 359 |
| 20 | ESI+: 361 |
| 21 | ESI+: 343 |
| 22 | ESI+: 343 |
| 23 | ESI+: 375 |

TABLE 66-continued

| Ex | Dat |
|---|---|
| 24 | ESI+: 373 |
| 25 | ESI+: 377 |
| 26 | ESI+: 427 |
| 27 | ESI+: 393 |
| 28 | ESI+: 377 |
| 29 | ESI+: 361 |
| 30 | ESI+: 388 |
| 31 | ESI+: 341 |
| 32 | ESI+: 341 |
| 33 | ESI+: 316 |
| 34 | ESI+: 377 |
| 35 | ESI+: 321 |
| 36 | ESI+: 346 |
| 37 | ESI+: 377 |
| 38 | ESI+: 377 |
| 39 | ESI+: 359 |
| 40 | ESI+: 357 |
| 41 | ESI+: 357 |
| 42 | ESI+: 341 |
| 43 | ESI+: 379 |
| 44 | ESI+: 341 |
| 45 | ESI+: 373, 375 |
| 46 | ESI+: 373 |
| 47 | ESI+: 373 |
| 48 | ESI+: 357 |
| 49 | ESI+: 357 |
| 50 | ESI+: 323 |
| 51 | ESI+: 323 |
| 52 | ESI+: 328 |
| 53 | ESI+: 413 |
| 54 | ESI+: 363 |
| 55 | ESI+: 373 |
| 56 | ESI+: 357 |
| 57 | ESI+: 343 |
| 58 | ESI+: 371 |
| 59 | ESI+: 357 |
| 60 | ESI+: 361 |
| 61 | ESI+: 357 |
| 62 | ESI+: 295 |
| 63 | ESI+: 343 |
| 64 | ESI+: 357 |
| 65 | ESI+: 375 |
| 66 | ESI+: 309 |
| 67 | ESI+: 357 |
| 68 | ESI+: 337 |
| 69 | ESI+: 343 |
| 70 | ESI+: 369 |
| 71 | ESI+: 269 |
| 72 | ESI+: 370 |
| 73 | ESI+: 343, 345 |
| 74 | ESI+: 325, 327 |
| 75 | ESI+: 295 |
| 76 | ESI+: 289 |
| 77 | ESI+: 369, 371 |
| 78 | ESI+: 371 |
| 79 | ESI+: 341 |
| 80 | A/E+: 341 |
| 81 | ESI+: 385 |
| 82 | A/E+: 323 |
| 83 | ESI+: 373 |
| 84 | ESI+: 355 |
| 85 | ESI+: 355 |
| 86 | ESI+: 395 |
| 87 | ESI+: 373 |
| 88 | ESI+: 375, 377 |
| 89 | ESI+: 357 |
| 90 | ESI+: 413 |
| 91 | ESI+: 371, 373 |
| 92 | ESI+: 395 |
| 93 | ESI+: 355, 357 |
| 94 | A/E+: 371 |
| 95 | ESI+: 359, 361 |
| 96 | A/E+: 389, 391 |
| 97 | ESI+: 380, 382 |
| 98 | ESI+: 350, 352 |
| 99 | ESI+: 375, 377 |
| 100 | ESI+: 393, 395 |
| 101 | ESI+: 357, 359 |
| 102 | ESI+: 329, 331 |
| 103 | ESI+: 303, 305 |
| 104 | ESI+: 344, 346 |
| 105 | ESI+: 337 |
| 106 | ESI+: 356, 358 |
| 107 | ESI+: 315, 317 |
| 108 | ESI+: 355 |
| 109 | ESI+: 357, 359 |
| 110 | ESI+: 357, 359 |
| 111 | ESI+: 389, 391 |

TABLE 67

| Ex | Dat |
|---|---|
| 112 | ESI+: 373, 375 |
| 113 | ESI+: 368 |
| 114 | ESI+: 373 |
| 115 | ESI+: 357 |
| 116 | ESI+: 318 |
| 117 | ESI+: 355 |
| 118 | ESI+: 337 |
| 119 | ESI+: 385 |
| 120 | ESI+: 374 |
| 121 | ESI+: 371, 373 |
| 122 | ESI+: 353, 355 |
| 123 | ESI+: 359 |
| 124 | ESI+: 375, 377 |
| 125 | ESI+: 341 |
| 126 | ESI+: 371, 373 |
| 127 | ESI+: 354, 356 |
| 128 | ESI+: 375, 377 |
| 129 | ESI+: 367 |
| 130 | ESI+: 373, 375 |
| 131 | ESI+: 356 |
| 132 | ESI+: 391, 393 |
| 133 | FAB+: 291 |
| 134 | ESI+: 343 |
| 135 | ESI+: 359 |
| 136 | ESI+: 343 |
| 137 | ESI+: 359 |
| 138 | ESI+: 359 |
| 139 | ESI+: 316 |
| 140 | ESI+: 350 |
| 141 | ESI+: 334 |
| 142 | ESI+: 379 |
| 143 | ESI+: 370 |
| 144 | ESI+: 363 |
| 145 | ESI+: 345 |
| 146 | ESI+: 361 |
| 147 | ESI+: 361 |
| 148 | ESI+: 345 |
| 149 | ESI+: 362 |
| 150 | ESI+: 334 |
| 151 | ESI+: 361 |
| 152 | ESI+: 359 |
| 153 | A/E+: 359 |
| 154 | ESI+: 377 |
| 155 | ESI+: 341 |
| 156 | ESI+: 367 |
| 157 | ESI+: 346 |
| 158 | ESI+: 369 |
| 159 | ESI+: 357 |
| 160 | ESI+: 327 |
| 161 | ESI+: 343 |
| 162 | ESI+: 361 |
| 163 | ESI+: 344 |
| 164 | ESI+: 362 |
| 165 | ESI+: 328 |
| 166 | ESI+: 373 |
| 167 | ESI+: 359, 361 |
| 168 | ESI+: 377, 379 |
| 169 | ESI+: 360, 362 |
| 170 | ESI+: 341 |
| 171 | ESI+: 362 |

TABLE 67-continued

| Ex | Dat |
|---|---|
| 172 | ESI+: 355 |
| 173 | ESI+: 344, 346 |
| 174 | ESI+: 373, 375 |
| 175 | ESI+: 343, 345 |
| 176 | ESI+: 377, 379 |
| 177 | ESI+: 389, 391 |
| 178 | ESI+: 378 |
| 179 | ESI+: 327 |
| 180 | ESI+: 377 |
| 181 | ESI+: 377 |
| 182 | ESI+: 377 |
| 183 | ESI+: 377, 379 |
| 184 | ESI+: 380, 382 |
| 185 | ESI+: 357, 359 |
| 186 | ESI+: 389, 391 |
| 187 | ESI+: 377 |
| 188 | ESI+: 309 |
| 189 | ESI+: 323 |
| 190 | ESI+: 327 |
| 191 | ESI+: 343 |
| 192 | ESI+: 323 |
| 193 | ESI+: 339, 341 |
| 194 | ESI+: 325 |
| 195 | ESI+: 377, 379 |
| 196 | ESI+: 395 |
| 197 | ESI+: 357 |
| 198 | ESI+: 289, 291 |
| 199 | ESI+: 359 |
| 200 | ESI+: 361 |
| 201 | ESI+: 361 |
| 202 | ESI+: 357 |
| 203 | ESI+: 373 |
| 204 | ESI+: 373 |
| 205 | ESI+: 345 |
| 206 | ESI+: 357, 359 |
| 207 | ESI+: 342 |
| 208 | ESI+: 324 |
| 209 | ESI+: 361, 363 |
| 210 | ESI+: 393, 395 |
| 211 | ESI+: 361, 363 |
| 212 | ESI+: 379, 381 |
| 213 | ESI+: 339, 341 |
| 214 | ESI+: 361, 363 |
| 215 | ESI+: 359 |
| 216 | ESI+: 343 |
| 217 | ESI+: 343 |
| 218 | ESI+: 359 |
| 219 | ESI+: 337 |
| 220 | ESI+: 357, 359 |
| 221 | ESI+: 377, 379 |
| 222 | ESI+: 353 |

TABLE 68

| Ex | Dat |
|---|---|
| 223 | ESI+: 378 |
| 224 | ESI+: 357 |
| 225 | ESI+: 291 |
| 226 | ESI+: 345 |
| 227 | ESI+: 345 |
| 228 | ESI+: 327 |

TABLE 69

| Ex | Dat (NMR-DMSO-d$^6$) |
|---|---|
| 2 | 5.03 (2H, s), 5.51 (1H, brs), 6.62 (2H, s), 7.45-7.51 (2H, m), 8.25 (1H, d, J = 8.8 Hz), 8.32 (1H, s), 8.51 (1H, dd, J = 8.8, 1.6 Hz), 8.66 (1H, s) |
| 6 | 2.80 (3H, s), 7.44-7.52 (2H, m), 7.73 (1H, s), 8.24 (1H, d, J = 8.9 Hz), 8.37 (1H, brs), 8.47 (1H, dd, J = 8.8, 2.0 Hz), 8.54 (2H, brs), 8.74 (2H, brs) |
| 17 | 1.99 (3H, s), 7.50 (2H, t, J = 7.8 Hz), 8.23 (1H, s), 8.28 (1H, d, J = 8.8 Hz), 8.42-8.46 (1H, m), 8.57 (2H, brs), 8.78 (2H, brs), 9.15 (1H, s) |
| 31 | 2.28 (3H, s), 7.31-7.40 (1H, m), 7.50-7.59 (2H, m), 8.09 (1H, s), 8.24 (1H, d, J = 8.8 Hz), 8.41-8.47 (1H, m), 8.55 (2H, brs), 8.70 (2H, brs), 9.09 (1H, s) |
| 60 | 7.36-7.40 (1H, m), 7.56-7.67 (2H, m), 8.15 (1H, s), 8.33 (1H, d, J = 8 Hz), 8.51 (1H, d, J = 8 Hz), 8.56 (2H, brs), 8.68 (2H, brs), 9.23 (1H, s), 12.33 (1H, brs) |
| 73 | 7.45-7.50 (1H, m), 7.55-7.58 (2H, m), 8.12 (1H, s), 8.30 (1H, d, J = 8 Hz), 8.51 (1H, d, J = 8 Hz), 8.56 (2H, brs), 8.66 (2H, brs), 9.19 (1H, s), 12.22 (1H, brs) |
| 74 | 7.47-7.49 (2H, m), 7.60-7.64 (2H, m), 8.12 (1H, s), 8.30 (1H, d, J = 8 Hz), 8.55 (2H, d, J = 8 Hz), 8.58 (2H, brs), 8.67 (2H, brs), 9.18 (1H, s), 12.23 (1H, brs) |
| 95 | 7.51-7.54 (1H, m), 7.59-7.69 (3H, m), 7.75-7.77 (1H, m), 7.94 (1H, s), 8.31-8.34 (1H, m), 8.58-8.60 (3H, m), 8.69 (2H, brs), 9.24 (1H, s) |
| 108 | 2.23 (3H, s), 2.87 (3H, s), 7.35-7.40 (1H, m), 7.48-7.60 (2H, m), 8.05 (1H, s), 8.30 (1H, d, J = 8 Hz), 8.52 (1H, d, J = 8 Hz), 8.58 (2H, brs), 8.73 (2H, brs), 12.34 (1H, brs) |
| 109 | 1.96 (3H, s), 7.26-7.39 (3H, m), 7.95 (1H, s), 8.31 (1H, d, J = 10 Hz), 8.59 (1H, d, J = 10 Hz), 8.64 (2H, brs), 8.78 (2H, brs), 9.20 (1H, s) |
| 114 | 2.26 (3H, s), 2.87 (3H, s), 7.50-7.54 (2H, m), 8.20 (1H, s), 8.29 (1H, d, J = 9.0 Hz), 8.51 (1H, d, J = 9.0 Hz), 8.62 (2H, brs), 8.83 (2H, brs), 9.12 (1H, s) |
| 115 | 2.86 (3H, s), 7.44-7.53 (4H, m), 7.99 (1H, s), 8.21 (1H, d, J = 8 Hz), 8.41 (1H, d, J = 8 Hz), 8.53 (4H, brs), 11.98 (1H, brs) |
| 117 | 2.25 (3H, s), 2.85 (3H, s), 7.40-7.44 (2H, m), 7.74-7.78 (1H, m), 8.02 (1H, s), 8.26 (1H, d, J = 10 Hz), 8.54 (1H, d, J = 10 Hz), 8.61 (2H, brs), 8.74 (2H, brs), 9.12 (1H, s) |
| 126 | 2.17 (3H, s), 2.86 (3H, s), 7.48-7.51 (2H, m), 7.78 (1H, dd, J = 8.2, 2.1 Hz), 7.90 (1H, d, J = 1.8 Hz), 8.28 (1H, d, J = 8.8 Hz), 8.51 (1H, d, J = 8.9 Hz), 8.56 (2H, brs), 8.72 (2H, brs) |
| 141 | 6.62 (2H, s), 7.82-7.86 (1H, m), 7.94 (1H, d, J = 7.9 Hz), 8.00 (1H, d, J = 5.6 Hz), 8.09 (1H, d, J = 8.6 Hz), 8.13 (1H, d, J = 9.6 Hz), 8.36 (1H, s), 8.49 (1H, d, J = 8.6 Hz), 8.67 (1H, d, J = 5.7 Hz) |
| 144 | 6.63 (2H, s), 7.50 (2H, t, J = 8.2 Hz), 8.24 (1H, d, J = 8.7 Hz), 8.35 (1H, s), 8.63 (1H, d, J = 8.7 Hz), 8.72 (1H, s) |

TABLE 70

| Ex | Dat (NMR-DMSO-d⁶) |
|---|---|
| 147 | 6.63 (2H, s), 7.51 (1H, t, J = 8.4 Hz), 7.61 (1H, d, J = 8.0 Hz), 7.65-7.74 (1H, m), 8.19 (1H, s), 8.24 (1H, d, J = 8.7 Hz), 8.60-8.66 (1H, m), 8.71 (1H, s) |
| 148 | 6.63 (2H, s), 7.38 (2H, t, J = 8.0 Hz), 7.67-7.80 (1H, m), 8.24 (1H, d, J = 8.7 Hz), 8.32 (1H, brs), 8.60-8.64 (1H, m), 8.71 (1H, d, J = 1.7 Hz) |
| 149 | 6.63 (2H, s), 8.34 (1H, s), 8.35 (1H, d, J = 8.9 Hz), 8.69 (1H, d, J = 8.9 Hz), 8.87 (2H, s), 8.91 (1H, s) |
| 151 | 6.63 (2H, s), 7.42-7.49 (1H, m), 7.59-7.65 (1H, m), 7.68-7.73 (1H, m), 8.21 (1H, d, J = 8.7 Hz), 8.24 (1H, s), 8.59 (1H, d, J = 8.7 Hz), 8.64 (1H, s) |
| 152 | 2.69 (3H, s), 6.63 (2H, s), 7.45-7.49 (2H, m), 8.16 (1H, d, J = 8.8 Hz), 8.30 (1H, s), 8.53 (1H, d, J = 8.8 Hz), 8.54 (1H, s) |
| 156 | 0.89-0.94 (2H, m), 1.12-1.17 (2H, m), 2.42-2.48 (1H, m), 6.62 (2H, s), 7.32-7.38 (2H, m), 7.66-7.73 (1H, m), 8.28 (1H, s), 8.43 (1H, s), 8.47 (1H, d, J = 8.8 Hz), 8.53-8.56 (1H, m) |
| 157 | 6.63 (2H, s), 8.29 (1H, d, J = 8.7 Hz), 8.33 (1H, brs), 8.62-8.67 (1H, m), 8.79 (1H, d, J = 1.8 Hz), 8.87 (2H, s) |
| 158 | 1.46 (6H, d, J = 7.2 Hz), 3.75-3.85 (1H, m), 6.62 (2H, s), 7.32-7.38 (2H, m), 7.66-7.73 (1H, m), 8.28-8.31 (2H, m), 8.50-8.53 (1H, m), 8.62 (1H, s) |
| 159 | 3.67 (3H, s), 6.63 (2H, s), 7.03 (1H, t, J = 8.5 Hz), 7.11 (1H, d, J = 8.5 Hz), 7.56-7.64 (1H, m), 8.18 (1H, d, J = 8.7 Hz), 8.23 (1H, s), 8.57-8.61 (1H, m), 8.63 (1H, d, J = 1.9 Hz) |
| 160 | 6.63 (2H, s), 7.41-7.50 (2H, m), 7.56-7.70 (2H, m), 8.21 (1H, d, J = 8.7 Hz), 8.42 (1H, brs), 8.58-8.64 (1H, m), 8.66 (1H, d, J = 1.9 Hz) |
| 161 | 6.63 (2H, s), 7.51-7.65 (3H, m), 7.68-7.72 (1H, m), 8.20 (1H, d, J = 8.8 Hz), 8.23 (1H, s), 8.57-8.62 (1H, m), 8.64 (1H, d, J = 1.9 Hz) |
| 162 | 6.63 (2H, s), 7.38-7.42 (2H, m), 7.72-7.74 (1H, m), 8.30-8.34 (2H, m), 8.66-8.67 (1H, m), 8.88 (1H, s) |
| 164 | 6.63 (2H, s), 8.20 (1H, s), 8.28 (1H, d, J = 8.7 Hz), 8.62-8.67 (1H, m), 8.78 (1H, d, J = 1.8 Hz), 8.89 (1H, s), 8.92 (1H, s) |
| 169 | 6.63 (2H, s), 7.69 (1H, d, J = 5.2 Hz), 8.22 (1H, s), 8.31 (1H, d, J = 8.8 Hz), 8.66 (1H, d, J = 8.8 Hz), 8.78 (1H, d, J = 5.2 Hz), 8.84 (1H, s), 8.92 (1H, s) |
| 170 | 2.69 (3H, s), 6.62 (2H, s), 7.32-7.39 (2H, m), 7.66-7.73 (1H, m), 8.15 (1H, d, J = 8.8 Hz), 8.28 (1H, brs), 8.41-8.54 (2H, m) |
| 171 | 6.62 (2H, s), 8.20 (1H, s), 8.28 (1H, d, J = 8.7 Hz), 8.62-8.67 (1H, m), 8.78 (1H, d, J = 1.8 Hz), 8.89 (1H, s), 8.92 (1H, s) |

TABLE 71

| Ex | Dat (NMR-DMSO-d⁶) |
|---|---|
| 172 | 1.39 (3H, t, J = 7.6 Hz), 3.15 (2H, q, J = 7.6 Hz), 6.63 (2H, s), 7.32-7.39 (2H, m), 7.66-7.74 (1H, m), 8.22 (1H, d, J = 8.8 Hz), 8.29 (1H, s), 8.50-8.56 (2H, m) |
| 174 | 3.68 (3H, s), 6.63 (2H, s), 6.96-7.01 (1H, m), 7.16-7.19 (1H, m), 7.40-7.44 (1H, m), 8.21 (1H, d, J = 8 Hz), 8.35 (1H, brs), 8.59 (1H, d, J = 8 Hz), 8.72 (1H, s) |
| 176 | 6.62 (2H, s), 7.44-7.49 (1H, m), 7.63-7.67 (1H, m), 7.71-7.74 (1H, m), 8.25-8.28 (2H, m), 8.63-8.65 (1H, m), 8.78 (1H, s) |
| 187 | 6.63 (2H, s), 7.38-7.44 (2H, m), 7.70 (1H, t, J = 54 Hz), 7.72-7.79 (1H, m), 8.32 (1H, d, J = 8.8 Hz), 8.39 (1H, s), 8.62-8.65 (1H, m), 8.92 (1H, s) |
| 192 | 2.67 (3H, s), 6.62 (2H, s), 7.40-7.45 (2H, m), 7.54-7.66 (2H, m), 8.12 (1H, d, J = 8.8 Hz), 8.40 (1H, brs), 8.49-8.52 (2H, m) |
| 193 | 2.67 (3H, s), 6.62 (2H, s), 7.48-7.61 (3H, m), 7.65-7.68 (1H, m), 8.11 (1H, d, J = 8.8 Hz), 8.21 (1H, d, J = 1.5 Hz), 8.47-8.52 (2H, m) |
| 206 | 2.69 (3H, s), 6.62 (2H, s), 7.45-7.50 (1H, m), 7.58 (1H, d, J = 8.0 Hz), 7.64-7.70 (1H, m), 8.13-8.16 (2H, m), 8.51-8.54 (2H, m) |
| 207 | 2.72 (3H, s), 6.62 (2H, s), 8.20 (1H, d, J = 8.8 Hz), 8.27 (1H, brs), 8.54-8.56 (1H, m), 8.59 (1H, brs), 8.84 (2H, s) |
| 208 | 2.70 (3H, s), 6.62 (2H, s), 7.67-7.70 (2H, m), 8.17 (1H, d, J = 8.8 Hz), 8.38 (1H, brs), 8.51-8.56 (2H, m), 8.66-8.68 (1H, m), 8.83 (1H, brs) |
| 215 | 6.62 (2H, s), 7.44-7.81 (5H, m), 8.29 (1H, d, J = 8.7 Hz), 8.49 (1H, brs), 8.59-8.62 (1H,m), 8.87 (1H, s) |
| 219 | 1.37 (3H, t, J = 7.5 Hz), 3.13 (2H, q, J = 7.5 Hz), 6.62 (2H, s), 7.40-7.45 (2H, m), 7.55-7.65 (2H, m), 8.18 (1H, d, J = 8.8 Hz), 8.40 (1H, brs), 8.48-8.52 (2H, m) |
| 223 | 6.63 (2H, s), 7.73 (1H, t, J = 54 Hz), 8.35-8.39 (2H, m), 8.66 (1H, dd, J = 8.8, 1.6 Hz), 8.89 (2H, s), 8.97 (1H, s) |
| 224 | 5.03 (2H, s), 5.49 (1H, brs), 6.62 (2H, s), 7.33-7.39 (2H, m), 7.67-7.74 (1H, m), 8.24 (1H, d, J = 8.8 Hz), 8.29 (1H, brs), 8.50-8.53 (1H, m), 8.65 (1H, s) |

TABLE 72
| PEx | Str |
|---|---|
| 521 | 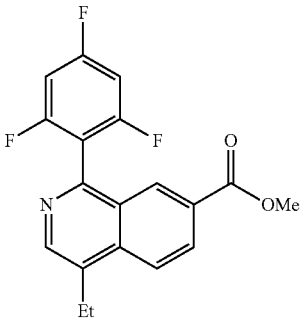 [SMILES: CCc1cnc(-c2c(F)cc(F)cc2F)c2cc(C(=O)OC)ccc12] |
| 522 | 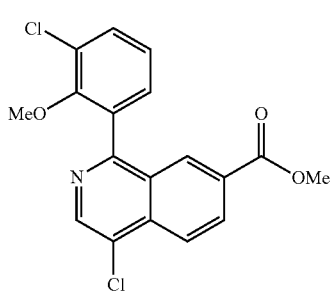 [SMILES: COC(=O)c1ccc2c(Cl)cnc(-c3cccc(Cl)c3OC)c2c1] |
| 523 | 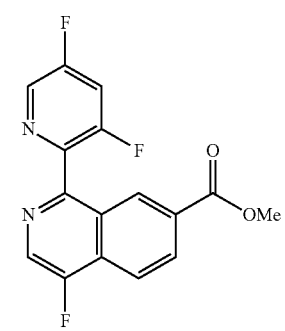 [SMILES: COC(=O)c1ccc2c(F)cnc(-c3ncc(F)cc3F)c2c1] |
| 524 | 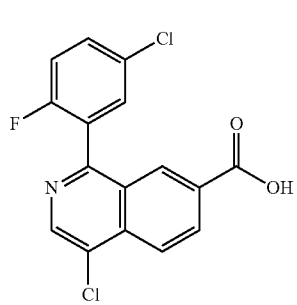 |
| 525 | 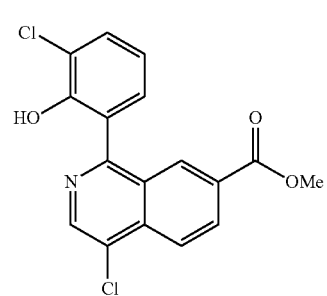 [SMILES: COC(=O)c1ccc2c(Cl)cnc(-c3cccc(F)c3O)c2c1] |
TABLE 72-continued
| PEx | Str |
|---|---|
| 526 | 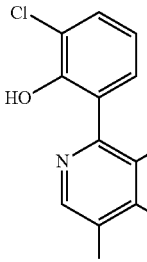 |
| 527 | 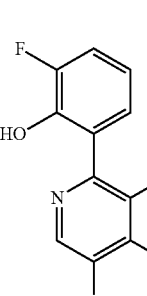 |
| 528 |  |
| 529 | 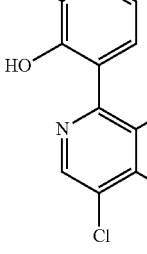 |
| 530 |  |

TABLE 73
| PEx | Str |
|---|---|
| 531 | 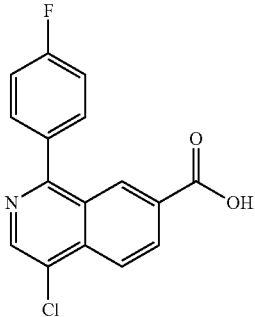 [SMILES: O=C(O)c1ccc2c(Cl)cnc(-c3ccc(F)cc3)c2c1] |
| 532 | 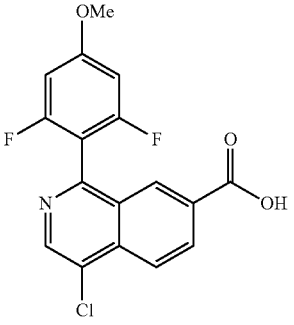 [SMILES: COc1cc(F)c(-c2ncc(Cl)c3ccc(C(=O)O)cc23)c(F)c1] |
| 533 | 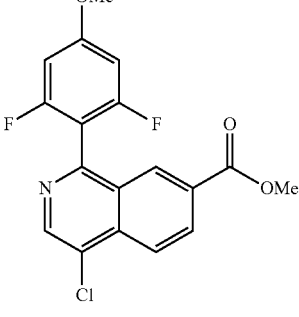 |
| 534 | 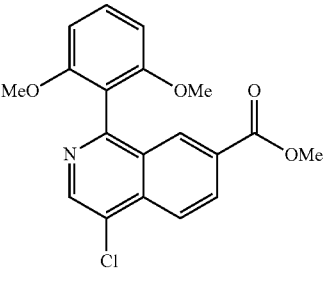 [SMILES: COC(=O)c1ccc2c(Cl)cnc(-c3c(OC)cccc3OC)c2c1] |
| 535 | 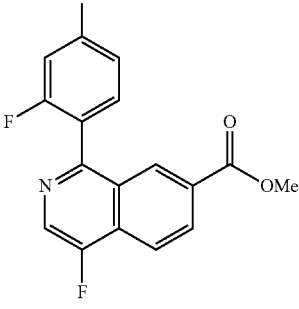 |
TABLE 73-continued
| PEx | Str |
|---|---|
| 536 | 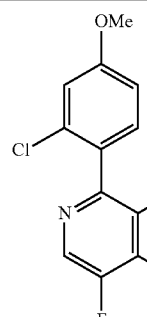 |
| 537 | 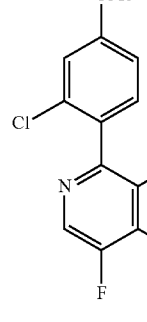 |
| 538 | 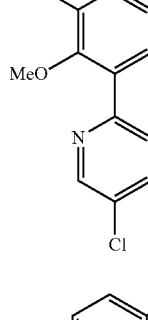 |
| 539 | 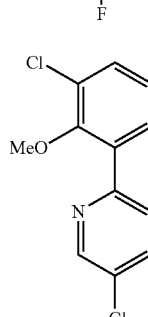 |
| 540 | 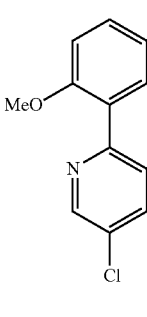 |

TABLE 74

| PEx | Str |
|---|---|
| 541 | (chemical structure) |
| 542 | (chemical structure) |
| 543 | (chemical structure) |
| 544 | (chemical structure) |
| 545 | (chemical structure) |

TABLE 74-continued

| PEx | Str |
|---|---|
| 546 | (chemical structure) |
| 547 | (chemical structure) |
| 548 | (chemical structure) |
| 549 | (chemical structure) |
| 550 | (chemical structure) |

TABLE 75

| PEx | Str |
|---|---|
| 551 | 4-chloro-1-(5-fluoro-2-methoxyphenyl)isoquinoline-7-carboxylic acid |
| 552 | 4-chloro-1-(2-fluoro-3-methylphenyl)isoquinoline-7-carboxylic acid |
| 553 | methyl 4-chloro-1-(3-fluoro-2-methylphenyl)isoquinoline-7-carboxylate |
| 554 | 4-chloro-1-(3-fluoro-2-methylphenyl)isoquinoline-7-carboxylic acid |
| 555 | methyl 4-fluoro-1-(3,5-difluoro-4-(trimethylsilyl)pyridin-2-yl)isoquinoline-7-carboxylate |

TABLE 75-continued

| PEx | Str |
|---|---|
| 556 | methyl 4-chloro-1-(5-chloro-2-fluorophenyl)isoquinoline-7-carboxylate |
| 557 | 4-fluoro-1-(3,5-difluoropyridin-2-yl)isoquinoline-7-carboxylic acid |
| 558 | methyl 4-chloro-1-(4-fluorophenyl)isoquinoline-7-carboxylate |
| 559 | methyl 4-bromo-1-(2,4-difluorophenyl)isoquinoline-7-carboxylate |
| 560 | 4-bromo-1-(2,4,6-trifluorophenyl)isoquinoline-7-carboxylic acid |

TABLE 76

| PEx | Str |
|---|---|
| 561 | 1-(2,4,6-trifluorophenyl)-4-ethyl-isoquinoline-7-carboxylic acid |
| 562 | 1-(2,4-difluorophenyl)-4-ethyl-isoquinoline-7-carboxylic acid methyl ester |
| 563 | 1-(2,4-difluorophenyl)-4-ethyl-isoquinoline-7-carboxylic acid |
| 564 | 1-(2-chloro-6-fluorophenyl)-4-ethyl-isoquinoline-7-carboxylic acid methyl ester |
| 565 | 1-(2-chloro-6-fluorophenyl)-4-ethyl-isoquinoline-7-carboxylic acid |

TABLE 77

| PEx | Syn | Dat |
|---|---|---|
| 521 | 521 | A/E+: 346 |
| 522 | 522 | ESI+: 362, 364 |
| 523 | 523 | ESI+: 319 |
| 524 | 2 | ESI+: 336 |
| 525 | 4 | ESI+: 348, 350 |
| 526 | 2 | ESI+: 334, 336 |
| 527 | 4 | ESI+: 332, 334 |
| 528 | 2 | ESI+: 318, 320 |
| 529 | 4 | ESI+: 346, 348 |
| 530 | 2 | ESI+: 332, 334 |
| 531 | 2 | ESI+: 302, 304 |
| 532 | 2 | ESI+: 350, 352 |
| 533 | 4 | ESI+: 364, 366 |
| 534 | 4 | A/E+: 358, 360 |
| 535 | 4 | ESI+: 330 |
| 536 | 4 | ESI+: 346 |
| 537 | 2 | ESI+: 348, 350 |
| 538 | 4 | A/E+: 346, 348 |
| 539 | 12 | ESI+: 318 |
| 540 | 12 | ESI+: 302 |
| 541 | 2 | ESI+: 316 |
| 542 | 2 | ESI+: 332 |
| 543 | 4 | ESI+: 364 |
| 544 | 6 | ESI+: 356 |
| 545 | 2 | NMR-DMSO-$d_6$: 3.60 (1H, s), 6.88 (2H, d, J = 8 Hz), 7.53 (1H, t, J = 8 Hz), 8.16 (1H, brs), 8.31 (1H, d, J = 8 Hz), 8.37 (1H, d, J = 8 Hz), 8.82 (1H, s) |
| 546 | 2 | ESI+: 342 |

TABLE 78

| Ex | Syn | Dat |
|---|---|---|
| 547 | 17 | ESI+: 329 |
| 548 | 2 | ESI+: 315 |
| 549 | 2 | A/E+: 350, 352 |
| 550 | 4 | NMR-DMSO-$d_6$: 2.37 (3H, brs), 3,89 (3H, s), 7.34 (1H, t, J = 8 Hz), 7.42 (1H, t, J = 8 Hz), 7.56 (1H, t, J = 8 Hz), 8.36-8.46 (3H, m), 8.91 (1H, s) |
| 551 | 2 | A/E+: 332, 334 |
| 552 | 2 | A/E+: 316 |
| 553 | 4 | ESI+: 330 |
| 554 | 2 | A/E+: 316 |
| 555 | 9 | ESI+: 391 |
| 556 | 4 | A/E+: 350, 352 |
| 557 | 2 | ESI+: 305 |
| 558 | 4 | ESI+: 316, 318 |
| 559 | 4 | A/E+: 378, 380 |
| 560 | 2 | A/E+: 382, 384 |
| 561 | 2 | A/E+: 332 |
| 562 | 521 | ESI+: 328 |
| 563 | 2 | ESI+: 314 |
| 564 | 521 | ESI+: 344, 346 |
| 565 | 2 | A/E+: 330, 332 |

TABLE 79

| Ex | Sal | Str |
|---|---|---|
| 229 | Fum | 1-(5-chloro-2-fluorophenyl)-4-chloro-isoquinoline-7-carboxylic acid N-(diaminomethylene) amide |

TABLE 79-continued
| Ex | Sal | Str |
|---|---|---|
| 230 | Fum | 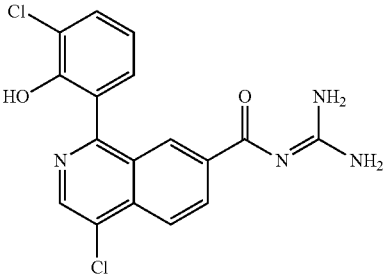 |
| 231 | Fum | 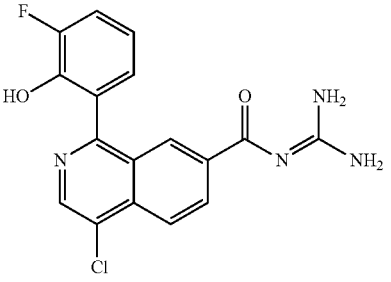 [SMILES: NC(N)=NC(=O)c1ccc2c(Cl)cnc(-c3cccc(F)c3O)c2c1] |
| 232 | Fum | 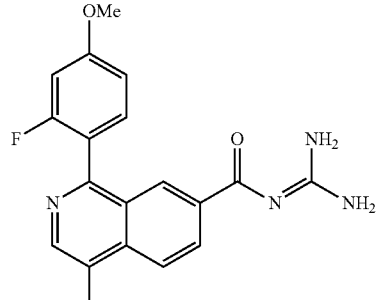 |
| 233 | Fum | 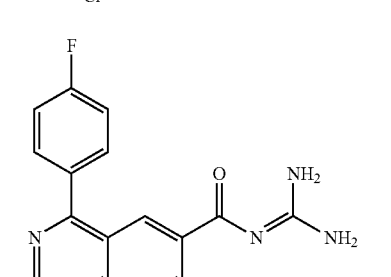 |
| 234 | Fum | 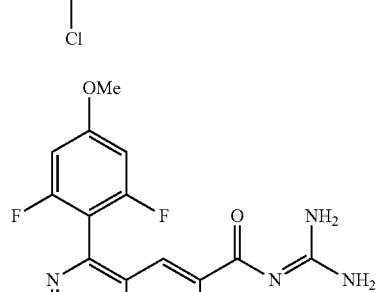 |
TABLE 79-continued
| Ex | Sal | Str |
|---|---|---|
| 235 | Fum | 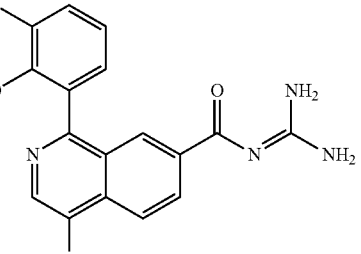 |
| 236 | Fum | 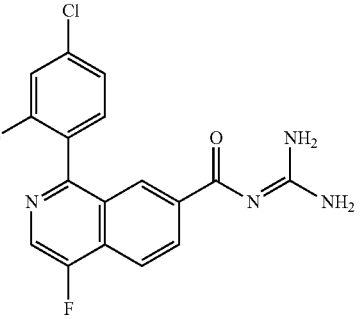 |
| 237 | Fum | 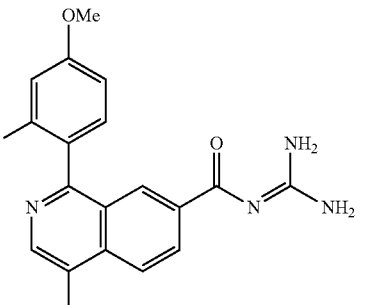 |
| 238 | Fum | 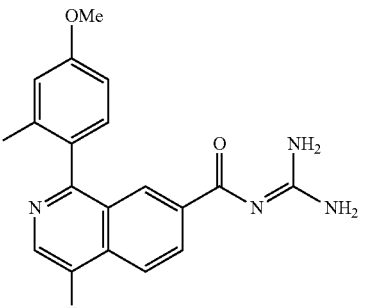 |

TABLE 80
| Ex | Sal | Str |
|---|---|---|
| 239 | Fum | 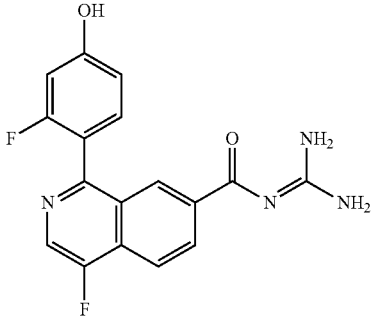 [SMILES: NC(N)=NC(=O)c1ccc2c(F)cnc(-c3ccc(O)cc3F)c2c1] |
| 240 | Fum | 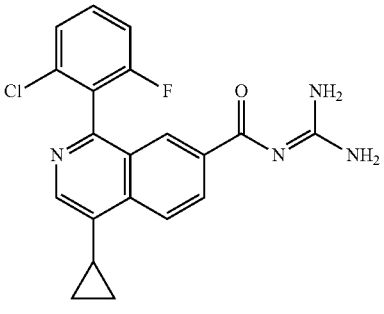 [SMILES: NC(N)=NC(=O)c1ccc2c(C3CC3)cnc(-c3c(F)cccc3Cl)c2c1] |
| 241 | Fum | 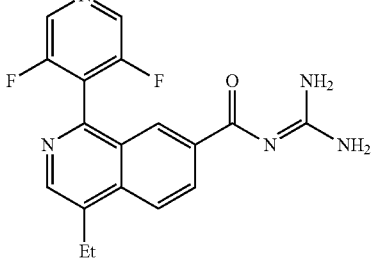 |
| 242 | Fum | 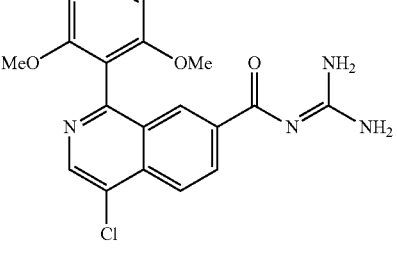 |
| 243 | Fum | 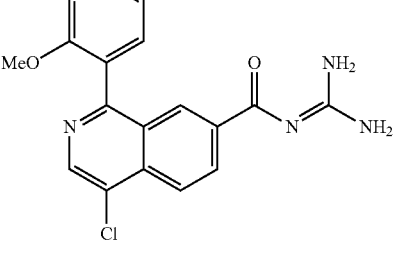 |
TABLE 80-continued
| Ex | Sal | Str |
|---|---|---|
| 244 | Fum | 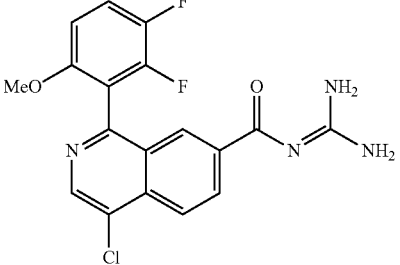 [SMILES: COc1cccc(OC)c1-c1ncc(Cl)c2ccc(C(=O)N=C(N)N)cc12] |
| 245 | Fum | 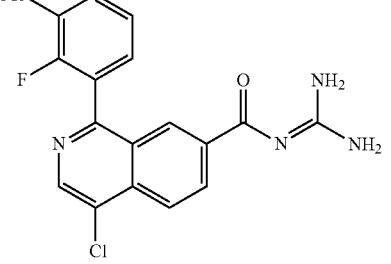 |
| 246 | Fum | 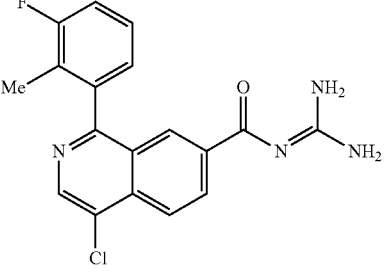 |
| 247 | Fum | 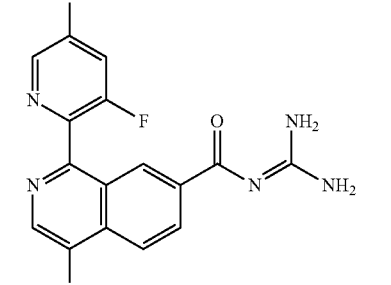 |
| 248 | Fum | 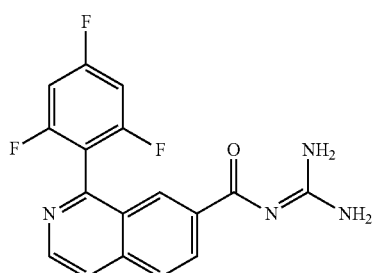 |

TABLE 81

| Ex | Sal | Str |
|---|---|---|
| 249 | Fum | 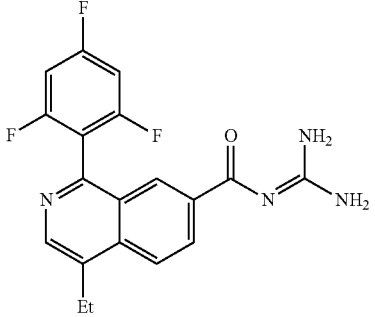 [SMILES: CCc1cnc(-c2c(F)cc(F)cc2F)c2cc(C(=O)N=C(N)N)ccc12] |
| 250 | Fum | 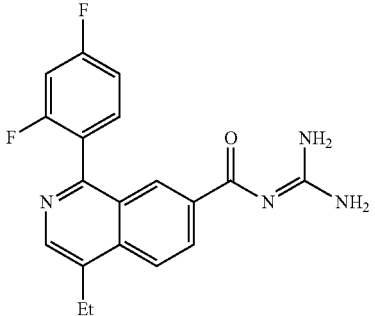 [SMILES: CCc1cnc(-c2ccc(F)cc2F)c2cc(C(=O)N=C(N)N)ccc12] |
| 251 | Fum | 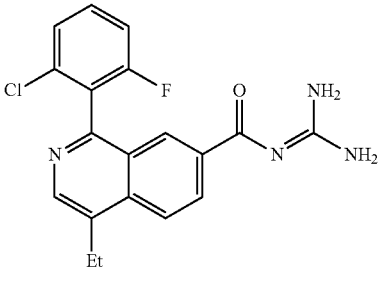 [SMILES: CCc1cnc(-c2c(F)cccc2Cl)c2cc(C(=O)N=C(N)N)ccc12] |

TABLE 82

| Ex | Dat |
|---|---|
| 229 | ESI+: 377, 379 |
| 230 | ESI+: 375, 377 |
| 231 | ESI+: 359, 361 |
| 232 | ESI+: 373, 375 |
| 233 | ESI+: 343, 345 |
| 234 | ESI+: 391, 393 |
| 235 | ESI+: 389, 391 |
| 236 | ESI+: 359 |
| 237 | ESI+: 357 |
| 238 | ESI+: 373 |
| 239 | ESI+: 343 |
| 240 | ESI+: 383 |
| 241 | ESI+: 356 |
| 242 | ESI+: 385 |
| 243 | ESI+: 373 |
| 244 | ESI+: 391 |
| 245 | ESI+: 357 |
| 246 | ESI+: 357, 359 |
| 247 | ESI+: 346 |
| 248 | ESI+: 423, 425 |
| 249 | ESI+: 373 |
| 250 | ESI+: 355 |
| 251 | ESI+: 371, 373 |

TEST EXAMPLES

Pharmacological activities of compound of formula (I) were confirmed by the following tests.

Test Example 1

Acquisition of HEK293 Cells for Forced Expressions of a Human 5-$HT_{5A}$ Receptor The ORF (open reading frame; protein coding region) of a human 5-$HT_{5A}$ receptor (Genbank AF498985) was cloned from a human hippocampus cDNA library, and then inserted into a pCR2.1 vector (Invitrogen), and *Escherichia coli* containing the plasmid was cultured in a large amount. Next, the full-length cDNA sequence of the human 5-$HT_{5A}$ receptor was analyzed, and recombined into a pCDNA3.1 vector (Invitrogen) as an expression vector and cultured in a large amount. HEK293 established cells (ATCC) derived from the human fetal kidney were seeded, the expression plasmid (1 μg) obtained above were added thereto with LIPOFECTAMINE 2000 (Invitrogen; 2 μl), the gene was transfected into HEK293 cells, and the expression cells were screened with a drug-resistant marker, Geneticin (G418 sulfate 500 μg/ml; Kanto Chemical Co., Inc.). Thus prepared recombinant cells which expressed the gene were cultured in a medium containing D-MEM (Dulbecco's modified eagle medium, Sigma), 10% FCS (Fetal calf serum: fetal bovine serum), 1% Pc./Sm (Penicillin/Streptomycin, Invitrogen), and 500 μg/ml G418 for 3 days. These experimental operations followed a manual for gene operation experiment and an instruction appended in a reagent, and the like, such as a known method (Sambrook, J. et al, Molecular Cloning-A Laboratory Manual", Cold Spring Harabor laboratory, NY, 1989).

Test Example 2

Test on a Human 5-$HT_{5A}$ Receptor Binding Inhibition (1) Preparation of a Membrane from HEK293 Cells for Forced Expressions of a Human 5-$HT_{5A}$ Receptor HEK293 cells for forced expressions of a human 5-$HT_{5A}$ receptor were cultured in a F500 plate, and scraped with a scraper. After centrifugation, the precipitate was collected, and an incubation buffer (50 mM Tris (HCl) (pH 7.4), 10 mM $MgSO_4$, and 0.5 mM EDTA (ethylenediamine tetraacetic acid)) was added thereto. After homogenization, it was further centrifuged, and the incubation buffer was added to the precipitate, followed by thoroughly suspending. The operation was repeated, and protein concentration was measured, thereby completing preparation of the membrane.

(2) Test on a Human 5-$HT_{5A}$ Receptor Binding Inhibition

A solution of the compound to be tested and 100 μM 5-CT (5-carboxamidetriptamine) in DMSO was added to a 96-well plate at 2 μl/well, suspended in an incubation buffer, and a membrane from HEK293 cells for forced expressions of a human 5-$HT_{5A}$ receptor prepared at 200 μg/ml was added at 100 μl/well. After incubation at room temperature for 15 minutes, a [$^3$H]5-CT solution (2 nM [$^3$H]5-CT, incubation buffer) was added thereto at 100 μl/well.

Separately, 100 μl of the solution was distributed into a liquid scintillation vial, and 2 ml of Aquasol II (registered trademark) was added thereto, followed by stirring. Then, radioactivity was measured by a liquid scintillation counter. It was incubated at 37° C. for 60 minutes. The reaction mixture was sucked into 96-well GF/C filter plate that had been pre-treated with 0.2% polyethyleneimine, and washed six times with an ice-cooled, 50 mM Tris (pH 7.5) buffer. The GF/C filter plate was dried.

Microscint TMPS (registered trademark) was added thereto at 40 μl/well. Radioactivity remaining on the GF/C filter plate was measured by a top counter.

The [$^3$H]5-CT binding inhibiting activity by the compound to be tested in each experiment was determined as an $IC_{50}$ value with a radioactivity upon addition of DMSO alone being 0% inhibition, and a radioactivity upon addition of 1 μM 5-CT being 100% inhibition. Separately, Ki values were calculated from the Kd value of the [$^3$H]5-CT determined from Scatchard analysis, by the following equation.

$$Ki=IC_{50}(1+\text{Concentraion of ligand added}/Kd(4.95 \text{ nM}))$$

As a result of this test, it was demonstrated that compound of formula (I) has a potent human 5-HT$_{5A}$ receptor binding inhibiting activity.

The compounds of Examples 1, 3, 5, 8 to 11, 13, 15 to 17, 19, 23, 24, 27, 31, 32, 39 to 42, 44, 46 to 51, 55 to 58, 61, 62, 65 to 67, 69, 70, 73, 74, 77, 83 to 85, 88, 89, 91, 93 to 99, 101, 102, 104, 107 to 117, 121, 123, 126, 130, 132, 134 to 138, 141, 142, 144 to 154, 157, 159 to 161, 164, 166 to 172, 175 to 190, 192 to 195, 197, 198, 200, 201, 203, 206 to 211, 213, 214, 216 to 222, and 226 showed Ki values ranging between 1 nM and 10 nM, respectively; the compounds of Examples 2, 4, 6, 7, 14, 18, 20 to 22, 25, 28 to 30, 33 to 36, 43, 45, 52, 54, 59, 63, 64, 68, 71, 75, 76, 78 to 82, 86, 87, 90, 100, 103, 105, 106, 118 to 120, 122, 124, 125, 127 to 129, 131, 133, 140, 143, 155, 156, 158, 163, 165, 173, 174, 191, 196, 199, 202, 204, 205, 212, 215, 224, 227, and 228 showed Ki values ranging between 10 nM and 100 nM, respectively; and the compounds of Examples 12, 37, 92, 139, and 225 showed Ki values ranging between 100 nM and 300 nM, respectively.

The Ki values of several compounds of Examples are shown in Tables below.

TABLE 83

| Ex | Ki [nM] |
| --- | --- |
| 6 | 13 |
| 60 | 1.3 |
| 147 | 1.6 |
| 148 | 1.4 |
| 151 | 4.1 |
| 152 | 1.3 |
| 114 | 3.7 |
| 157 | 5.3 |
| 159 | 7.1 |
| 160 | 3.3 |
| 161 | 3.4 |
| 162 | 1.2 |
| 164 | 4.7 |
| 170 | 1.9 |
| 171 | 6.2 |
| 187 | 4.6 |
| 192 | 1.8 |
| 211 | 2.3 |

As described above, it was confirmed that compound of formula (I) has 5-HT$_{5A}$ receptor affinity.

Test Example 3

Evaluation of Various Drugs Towards the Drugs (Methamphetamine, MK-801) which Increase Quantity of Motion in Mice (Method for Measuring Quantity of Motion by IR Irradiation)

The improvement effect of compound of formula (I) on schizophrenia was evaluated by measuring the quantity of motion inhibited by administration of the compound in a model in which the symptoms were induced by methamphetamine (hereinafter abbreviated as MAP) and MK-801.

(1) Animal
Species: Male ICR mouse
(2) Operation Procedure

The animal was taken out of a breeding cage, orally administered with a test compound, and then placed into a cage for breeding. After 30 minutes, the animal was put into a cage for measurement, and the quantity of motion with the test compound alone was measured. Further, after 30 to 90 minutes, the animal was taken out, and subcutaneously or intraperitoneally administered with a drug for increasing the quantity of motion (MAP; 1.5 mg/kg or MK-801; 0.3 mg/kg, dissolved in physiological saline, respectively). Then, the quantity of motion for a certain period of time (60 minutes) was measured using a device for measuring the quantity of motion (CompACT AMS manufactured by Muromachi Kikai Co., Ltd.) by means of an infrared sensor.

(3) Analysis

For a normal mouse (a mouse administered with physiological saline) and a mouse administered with a drug for increasing the quantity of motion, a Student's T test was performed for evaluation for each interval. For a group administered with the test compound, an assay was performed using a solvent (vehicle) group and a Dunnett's T test. For the evaluation, if there was a significant difference (P<0.05), it was considered that there is an effect.

As a result of this test, compound of formula (I) inhibited the increase in the quantity of motion of the mouse. For example, the compounds of Examples 73, 148, 157, 160, 187, and 192 significantly inhibited the hyperactivity induced by MK-801 at doses of 0.1 mg/kg, 0.03 mg/kg, 0.03 mg/kg, 0.01 mg/kg, 0.01 mg/kg, and 0.01 mg/kg, respectively. Further, the compound of Example 148 significantly inhibited the hyperactivity induced by MAP at a dose of 0.1 mg/kg.

As described above, it was confirmed that compound of formula (I) has an improvement effect for the increase of the quantity of motion (hyperactivity) which is a symptom of schizophrenia.

Test Example 4

Improvement Effect on Spontaneous Alternation Behavior Induced by Scoporamine or MK-801 in Mice The improvement effect of compound of formula (I) on cognitive impairment of dementia and schizophrenia was evaluated by a known test method as a model with short-term learning disorder.

(1) Animal
Species: Male ddY mouse
(2) Measurement Method

After 10 to 30 minutes from oral administration of the test compound, 0.5 mg/kg of Scoporamine or 0.15 mg/kg of MK-801 (in the case of a normal group, physiological saline was administered) was intraperitoneally administered. After 20 minutes, the test was conducted. In addition, solvent (vehicle) was orally administered to the normal group (to which physiological saline was administered) and to the control group (to which 0.5 mg/kg of Scoporamine or 0.15 mg/kg of MK-801 was administered), when the test compound was administered.

A mouse was placed at the end of one arm of a Y-maze having arms with the same length in three directions, and then allowed to explore freely and the number of arm entries was counted for 8 minutes. Further, spontaneous alternation behavior was defined as entries into all three different arms on consecutive occasions, and the ratio of the number of instances of this behavior to the total number of the entries was calculated as an alternation rate by the following formula:

Alternation rate(%)=Number of spontaneous alternation behaviors/(Total number of entries−2)×100.

(3) Data Analysis

If a significant difference between the normal group and the control group (Student's T test) was approved in the alternation rate (%), it was considered to have learning disorder by the administration of Scoporamine or MK-801. By carrying out a Dunnett's test on the group administered with the test compound with respect to the control group, the presence or absence of effect of the test compound on learning disorder was evaluated. For each assay, it was considered that there was a tendency when p<0.10 and there was a significant difference when p<0.05.

As a result of this test, compound of formula (I) inhibited the spontaneous alternation behavior in the mouse, induced by Scoporamine and MK-801. For example, the compound of Example 148 significantly inhibited spontaneous alternation behavior induced by Scoporamine at a dose of 0.01 mg/kg; the compound of Example 192 significantly inhibited spontaneous alternation behavior induced by Scoporamine at a dose of 0.003 mg/kg; the compounds of Examples 157 and 160 significantly inhibited spontaneous alternation behavior induced by Scoporamine at a dose of 0.001 mg/kg; and the compound of Example 187 significantly inhibited spontaneous alternation behavior induced by Scoporamine at a dose of 0.0003 mg/kg.

As a result of this test, it was confirmed that compound of formula (I) shows improvement effect on cognitive impairment of dementia and schizophrenia.

Test Example 5

Improvement Effect on Disorder of PCP-Induced Prepulse Inhibition (PPI) in Rats

When a sound stimulus is given to a human, a startled reaction occurs, but for a normal human, this startled reaction is inhibited when the sound stimulus is preceded by a weak sound stimulus. This inhibiting action is similarly lowered in a patient with schizophrenia. It is known that when a rat is administered with PCP (phencyclidine), a similar symptom to human schizophrenia occurs. Using this model, the improvement effect of compound of formula (I) on information processing disorder included in cognitive impairment of schizophrenia was evaluated.

The improvement effect of compound of formula (I) on schizophrenia was evaluated using a known model with PCP-induced prepulse inhibition disorder as a model with the condition of a disease. Specifically, it followed the method as described in "Neuropsychopharmacology, 1989; 2: 61-66, Mansbach, R. S. and Geyer, M. A. and Brain Research, 1998; 781: 227-235".

As a result of this test, it was confirmed that compound of formula (I) also has an effect on information processing disorder included in cognitive impairment of schizophrenia.

Test Example 6

Evaluation of Drug on Water Maze Learning Disorder in Old Rats

The improvement effect of compound of formula (I) on dementia was evaluated using a known model with water maze learning disorder as a model with the condition of the disease. Specifically, it followed the method described in J Pharmacol Exp Ther, 1996; 279: 1157-73, Yamazaki M. et al.

As a result of this test, it was confirmed that compound of formula (I) has effect on dementia.

Test Example 7

Evaluation of Drug in Forced Swimming Test in DBA/2 Mouse

The improvement effect of compound of formula (I) on depression can be evaluated by a known forced swimming test as an evaluation model. Specifically, it follows the method described in "Behav Brain Res. 2005; 156(1): 153-162, Ducottet C. et al.)".

From the test results of Test Examples 1 to 7, it was confirmed that compound of formula (I) can be used as an agent for treating or preventing $5-HT_{5A}$-related diseases, in particular, treating or preventing dementia, schizophrenia (including symptoms such as positive symptoms, negative symptoms, cognitive impairment, mood disorders, and the like), bipolar disorder, attention deficit hyperactivity disorder, psychological disorders (anxiety disorder, panic disorder, obsessive disorder, and the like), autism, mood disorders (anxiety disorder and depression disorder), somnipathy, neurodegenerative diseases, and cerebral infarction.

A pharmaceutical preparation containing one or two or more kinds of compound of formula (I) or a salt thereof as an active ingredient can be prepared by using pharmaceutical carriers, excipients, and the like that are each usually used in the art, by a method that is usually used.

Administration may be made in any form for either oral administration by tablets, pills, capsules, granules, powders, and solutions, or parenteral administration by injections for intraarticular injection, intravenous injection, and intramuscular injection, suppositories, ophthalmic solutions, ophthalmic oinments, percutaneous liquids, oinments, percutaneous patches, transmucosal liquids, transmucosal patches, and inhalations.

Regarding the solid composition for oral administration according to the present invention, tablets, powders, granules, or the like are used. In such a solid composition, one, or two or more active ingredients are mixed with at least one inactive excipient such as lactose, mannitol, glucose, hydroxypropyl cellulose, microcrystalline cellulose, starch, polyvinyl pyrrolidone, and/or magnesium meta-silicate alminate. According to a conventional method, the composition may contain inactive additives; for example, a lubricant such as magnesium stearate, a disintegrator such as carboxymethylstarch sodium, a stabilizing agent, and a dissolution promotor. As occasion demands, tablets or pills may be coated with a sugar, or a film of a gastric or enteric material.

The liquid composition for oral administration includes pharmaceutically acceptable emulsions, solutions, suspensions, syrups, elixirs, and the like, and contains an inert diluent that is commonly used, such as purified water or ethanol. In addition to the inert diluent, this liquid composition may contain an auxiliary agent such as a solubilizing agent, a moistening agent, and a suspending agent, a sweetener, a flavor, an aroma, and an antiseptic.

Injections for parenteral administration include aqueous or non-aqueous sterile solutions, suspensions, and emulsions. Examples of the aqueous solvent include distilled water for injection, and physiological saline. Examples of the non-aqueous solvent include propylene glycol, polyethylene glycol, vegetable oils such as olive oil, alcohols such as ethanol, and Polysorbate 80 (Pharmacopeia). Such a composition may further contain a tonicity agent, an antiseptic, a moistening agent, an emulsifying agent, a dispersing agent, a stabilizing agent, and a dissolution promotor. These are sterilized, for example, by filtration through a bacterium-retaining filter, blending of bactericides, or irradiation. In addition, these can also be used by producing a sterile solid composition, and dissolving or suspending it in sterile water or a sterile solvent for injection prior to its use.

Examples of the drug for external use include ointments, plasters, creams, jellies, cataplasms, sprays, lotions, ophthalmic solutions, and ophthalmic ointments. The drug contains commonly used ointment bases, lotion bases, aqueous or non-aqueous solutions, suspensions, emulsions, and the like. Examples of the ointment bases or lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, and sorbitan sesquioleate.

A transmucosal agent such as an inhalations and a transnasal agent can be used in a solid, liquid or semi-solid state, and may be produced in accordance with a conventionally known method. For example, a known excipient, and also a pH adjusting agent, an antiseptic, a surfactant, a lubricant, a stabilizer, a viscosity-increasing agent, and the like may be appropriately added thereto. For their administration, an appropriate device for inhalation or blowing may be used. For example, a compound may be administered alone or as a powder of a formulated mixture, or as a solution or suspension by combining it with a pharmaceutically acceptable carrier, using a conventionally known device or sprayer, such as a measured administration inhalation device. The dry powder inhaler or the like may be for single or multiple administration use, and a dry powder or a powder-containing capsule may be used. Alternatively, this may be in a form such as a high pressure aerosol spray which uses an appropriate propellant, for example, a suitable gas such as chlorofluoroalkane, hydrofluoroalkane, or carbon dioxide.

It is suitable that the daily dose is usually from about 0.0001 to 100 mg/kg per body weight in the case of oral administration, preferably 0.0001 to 10 mg/kg, and even more preferably 0.0001 to 1 mg/kg, and the preparation is administered in one portion or dividing it into 2 to 4 portions. Also, in the case of intravenous administration, the daily dose is administered suitably in a range from about 0.00001 to 1 mg/kg per body weight, and the preparation is administered once a day or two or more times a day. In the case of drugs for external use or transmucosal administration, the drug is administered usually in a range from about 0.0001 to 10 mg/kg per body weight, once a day or two or more times a day. The dose is appropriately decided, depending on individual cases by taking into consideration the symptom, age, sex and the like. The content of the active ingredients in the preparation is from 0.0001 to 50%, and more preferably 0.001 to 50%.

Compound of formula (I) can be used in combination with various therapeutic agents or prophylactic agents for the diseases, in which compound of formula (I) is considered effective, as described above. The combined preparation may be administered simultaneously; or separately, and continuously or at a desired time interval. The preparations to be co-administered may be a blend, or prepared individually.

Industrial Applicability

Compounds of formula (I) have potent $5\text{-HT}_{5A}$ receptor modulating action, and excellent pharmacological action based on said $5\text{-HT}_{5A}$ receptor modulating action. Pharmaceutical compositions of the present invention are useful for treatment or prevention of $5\text{-HT}_{5A}$ receptor-related diseases, and in particular, for treatment or prevention of dementia, schizophrenia, bipolar disorder, or attention deficit hyperactivity disorder.

The invention claimed is:

1. A compound of formula (I) or a pharmaceutically acceptable salt thereof:

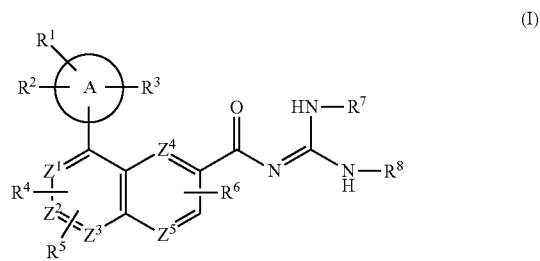

(wherein the symbols have the following meanings:

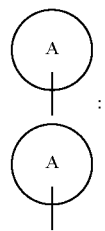

: aryl, cycloalkyl, cycloalkenyl or monocyclic nitrogen-containing heterocyclic group, $Z^1, Z^2, Z^3, Z^4$ and $Z^5$: one of any of them is a nitrogen atom, and the others are carbon atoms, in which the nitrogen atom is optionally oxidized to form an N-oxide, $R^1$, $R^2$ and $R^3$: each independently represents H, lower alkyl, halogen, halogeno-lower alkyl, —CN, —NO$_2$, —OR$^a$, —S-lower alkyl, —O-halogeno-lower alkyl, —CO$_2$R$^a$, —C(O)NR$^b$R$^c$, —SO$_2$-lower alkyl, or -lower alkylene-OR$^a$, $R^4$, $R^5$ and $R^6$: each independently represents H, lower alkyl, cycloalkyl, halogen, halogeno-lower alkyl, —CN, —NO$_2$, —OR$^a$, —SO$_2$-lower alkyl, —O-halogeno-lower alkyl, —CO$_2$R$^a$, —C(O)NR$^b$R$^c$, —SO$_2$-lower alkyl, or lower alkylene-OR$^a$, $R^a$, $R^b$ and $R^c$: each independently represents H or lower alkyl, and R⁷ and R⁸: each independently represents H or lower alkyl).

2. The compound or a pharmaceutically acceptable salt thereof according to claim 1, wherein $Z^1$ is a nitrogen atom, $Z^2, Z^3, Z^4$ and $Z^5$ are carbon atoms, the ring group A is phenyl, pyridyl, cyclopropyl, cyclohexenyl, cyclopentenyl, or pyrrolidinyl group, $R^1, R^2$ and $R^3$ are each H, lower alkyl, halogen, halogeno-lower alkyl, —CN, or —OR$^a$, $R^4, R^5$ and $R^6$ are each H, lower alkyl, cyclopropyl, halogen, halogeno-lower alkyl, —CN, or —C(O)NR$^b$R$^c$, and $R^7$ and $R^8$ are both H.

3. The compound or a pharmaceutically acceptable salt thereof according to claim 1, wherein $Z^3$ is a nitrogen atom, $Z^1, Z^2, Z^4$ and $Z^5$ are carbon atoms, the ring group A is phenyl, pyridyl, cyclopropyl, cyclohexenyl, cyclopentenyl, or pyrrolidinyl group, $R^1, R^2$ and $R^3$ are each H, lower alkyl, halogen, halogeno-lower alkyl, —CN, or —OR$^a$, $R^4, R^5$ and $R^6$ are each H, lower alkyl, cyclopropyl, halogen, halogeno-lower alkyl, —CN, or —C(O)NR$^b$R$^c$, and $R^7$ and $R^8$ are both H.

4. The compound or a pharmaceutically acceptable salt thereof according to claim 1, wherein $Z^1$ is a nitrogen atom, $Z^2, Z^3, Z^4$ and $Z^5$ are carbon atoms, the ring group A is phenyl or pyridyl group, $R^1, R^2$ and $R^3$ are each H, F, Cl, or —OR$^a$ group, $R^4, R^5$ and $R^6$ are each H, lower alkyl, F, Cl, or halogeno-lower alkyl group, and $R^7$ and $R^8$ are both H.

5. The compound or a pharmaceutically acceptable salt thereof according to claim 1, wherein $Z^3$ is a nitrogen atom, $Z^1, Z^2, Z^4$ and $Z^5$ are carbon atoms, the ring group A is phenyl or pyridyl group, $R^1, R^2$ and $R^3$ are each H, F, Cl, or —OR$^a$ group, $R^4, R^5$ and $R^6$ are each H, lower alkyl, F, Cl, or halogeno-lower alkyl group, and $R^7$ and $R^8$ are both H.

6. A compound or a pharmaceutically acceptable salt thereof, which is selected from the group consisting of:
   N-(diaminomethylene)-2-methyl-4-(2,4,6-trifluorophenyl)quinoline-6-carboxamide,
   1-(2-chloro-6-fluorophenyl)-N-(diaminomethylene)-4-fluoroisoquinoline-7-carboxamide,
   N-(diaminomethylene)-1-(2,6-difluorophenyl)-4-fluoroisoquinoline-7-carboxamide,
   1-(2-chloro-4-fluorophenyl)-N-(diaminomethylene)-4-fluoroisoquinoline-7-carboxamide,
   N-(diaminomethylene)-4-methyl-1-(2,4,6-trifluorophenyl)isoquinoline-7-carboxamide,
   N-(diaminomethylene)-2,3-dimethyl-4-(2,4,6-trifluorophenyl)quinoline-6-carboxamide,
   N-(diaminomethylene)-1-(3,5-difluoropyridin-4-yl)-4-fluoroisoquinoline-7-carboxamide,
   N-(diaminomethylene-4-fluoro-1-(2-fluoro-6-methoxyphenyl)isoquinoline-7-carboxamide,
   N-(diaminomethylene)-4-fluoro-1-(2-fluorophenyl)isoquinoline-7-carboxamide,
   1-(2-chlorophenyl)-N-(diaminomethylene)-4-fluoroisoquinoline-7-carboxamide,
   4-chloro-N-(diaminomethylene)-1-(2,6-difluorophenyl)isoquinoline-7-carboxamide,
   1-(3-chloro-5-fluoropyridin-4-yl)-N-(diaminomethylene)-4-fluoroisoquinoline-7-carboxamide,
   N-(diaminomethylene)-1-(2,6-difluorophenyl)-4-methylisoquinoline-7-carboxamide,
   1-(3-chloro-5-fluoropyridin-2-yl)-N-(diaminomethylene)-4-fluoroisoquinoline-7-carboxamide,
   N-(diaminomethylene)-4-(difluoromethyl)-1-(2,6-difluorophenyl)isoquinoline-7-carboxamide,
   N-(diaminomethylene)-1-(2-fluorophenyl)-4-methylisoquinoline-7-carboxamide, and
   4-chloro-N-(diaminomethylene)-1-(2,4-difluorophenyl)isoquinoline-7-carboxamide.

7. A pharmaceutical composition comprising the compound or a pharmaceutically acceptable salt thereof according to claim 1, and a pharmaceutically acceptable carrier.

8. The pharmaceutical composition according to claim 7 which is a $5\text{-HT}_{5A}$ receptor inhibitor.

9. The pharmaceutical composition according to claim 8 which is an agent for or treating dementia, schizophrenia, bipolar disorder, or attention deficit hyperactivity disorder.

10. A method for treating dementia, schizophrenia, bipolar disorder, or attention deficit hyperactivity disorder, comprising administering a therapeutically effective amount of the compound or a pharmaceutically acceptable salt thereof according to claim 1 to a patient.

11. The compound or a salt thereof according to claim 6, which is N-(diaminomethylene)-2-methyl-4-(2,4,6-trifluorophenyl)quinoline-6-carboxamide.

12. The compound or a salt thereof according to claim 6, which is N-(diaminomethylene)-1-(3,5-difluoropyridin-4-yl)-4-fluoroisoquinoline-7-carboxamide.

* * * * *